US008521558B2

(12) United States Patent
Malave et al.

(10) Patent No.: US 8,521,558 B2
(45) **Date of Patent: *Aug. 27, 2013**

(54) COMMUNICATION STATION AND SOFTWARE FOR INTERFACING WITH AN INFUSION PUMP, ANALYTE MONITOR, ANALYTE METER, OR THE LIKE

(75) Inventors: Luis J. Malave, Valencia, CA (US); Mark C. Estes, Simi Valley, CA (US); Jay Yonemoto, Diamond Bar, CA (US); J. Jeffrey Barlow, Valencia, CA (US); Todd M. Gross, Saugus, CA (US); John Shin, Glendale, CA (US); Paul S. Cheney, II, Winnetka, CA (US); Mike Dobbles, Burbank, CA (US); Clifford W. Hague, Sherman Oaks, CA (US); Deborah Ruppert, Los Angeles, CA (US); Kevin C. Wells, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/253,289

(22) Filed: Oct. 5, 2011

(65) Prior Publication Data

US 2012/0029941 A1 Feb. 2, 2012

Related U.S. Application Data

(60) Continuation of application No. 12/140,157, filed on Jun. 16, 2008, now abandoned, which is a continuation of application No. 10/180,732, filed on Jun. 26, 2002, now Pat. No. 7,647,237, which is a division of application No. 09/409,014, filed on Sep. 29, 1999, now abandoned, which is a continuation-in-part of application No. 29/087,251, filed on Apr. 29, 1998, now Pat. No. Des. 434,142.

(60) Provisional application No. 60/102,469, filed on Sep. 30, 1998, provisional application No. 60/121,565, filed on Feb. 25, 1999, provisional application No. 60/134,981, filed on May 20, 1999.

(51) Int. Cl.
*G06Q 10/00* (2012.01)

(52) U.S. Cl.
USPC .............................................. 705/2; 364/413

(58) Field of Classification Search
USPC .............................................................. 705/2
See application file for complete search history.

(56) References Cited

U.S. PATENT DOCUMENTS

| | | | |
|---|---|---|---|
| 4,270,532 | A | 6/1981 | Franetzki et al. |
| 4,679,562 | A | 7/1987 | Luksha |

(Continued)

FOREIGN PATENT DOCUMENTS

| | | |
|---|---|---|
| DE | 2807367 | 8/1979 |
| EP | 0777123 | 6/1997 |

(Continued)

OTHER PUBLICATIONS

"MiniMed™ 507 Insulin Pump User's Guide," (May 1996), pp. 1-127.

(Continued)

*Primary Examiner* — Hiep V Nguyen
(74) *Attorney, Agent, or Firm* — Medtronic MiniMed, Inc.

(57) ABSTRACT

A communication station is for use with a medical device (such as an infusion pump) and a processing device (such as a computer). The communication station includes a housing, a medical device interface coupled to the housing, a processing device interface coupled to the housing and a processor coupled to the housing. The device interface interfaces with the medical device, and the processing device interface interfaces with the processing device. The processor provides a communication path between the medical device and the processing device such that programming and instructions may be communicated from the processing device to the medical device and data may be transferred from the medical device to the processing device. The communication station may be combined with a system that is capable of generating reports either locally or remotely. In addition, the medical device interface may be a cradle that is configurable to attach to different shaped medical devices.

11 Claims, 35 Drawing Sheets

(56) References Cited

U.S. PATENT DOCUMENTS

| | | | | |
|---|---|---|---|---|
| 4,731,726 | A | 3/1988 | Allen, III | |
| 4,852,570 | A | 8/1989 | Levine | |
| D328,277 | S | 7/1992 | Leman et al. | |
| 5,225,763 | A | 7/1993 | Krohn et al. | |
| 5,251,126 | A * | 10/1993 | Kahn et al. | 600/309 |
| 5,311,449 | A | 5/1994 | Adams | |
| 5,374,620 | A | 12/1994 | Clark et al. | |
| 5,376,070 | A | 12/1994 | Purvis et al. | |
| 5,497,772 | A * | 3/1996 | Schulman et al. | 600/347 |
| 5,582,593 | A | 12/1996 | Hultman | |
| 5,665,065 | A | 9/1997 | Colman et al. | |
| 5,681,285 | A | 10/1997 | Ford et al. | |
| 5,771,890 | A | 6/1998 | Tamada | |
| 5,781,442 | A | 7/1998 | Engleson et al. | |
| 5,800,420 | A | 9/1998 | Gross et al. | |
| 5,807,375 | A | 9/1998 | Gross et al. | |
| 5,832,448 | A | 11/1998 | Brown | |
| 5,871,465 | A | 2/1999 | Vasko | |
| D408,783 | S | 4/1999 | Lucaci et al. | |
| 5,899,855 | A | 5/1999 | Brown | |
| 5,913,310 | A | 6/1999 | Brown | |
| 5,925,021 | A | 7/1999 | Castellano et al. | |
| 6,024,539 | A | 2/2000 | Blomquist | |
| D434,142 | S | 11/2000 | Cheney, II et al. | |
| 6,368,272 | B1 | 4/2002 | Porumbescu | |
| 6,558,321 | B1 | 5/2003 | Burd et al. | |
| 6,579,690 | B1 * | 6/2003 | Bonnecaze et al. | 435/14 |
| 7,647,237 | B2 | 1/2010 | Malave et al. | |

FOREIGN PATENT DOCUMENTS

| | | |
|---|---|---|
| WO | 9405355 | 3/1994 |
| WO | 9636923 | 11/1996 |

OTHER PUBLICATIONS

"MiniMed™ 507C Insulin Pump User's Guide," (Mar. 1998), pp. 1-132.

Alberto Riva, Riccardo Bellazzi, Mario Stefanelli, "A web-based system for the intelligent management of diabetic patients," Nov. 1997, IRCCS Policlinico San Matteo, Pavia, Italy, Department of Computer Sciences, University of Pavia, Italy, M.D. Computing, 14(5): 360-364.

Insulin Treatment: A Non-Stop Revolution, J. Mirouze, Diabetologia, Springer-Verlag, 1983, issue 25, pp. 209-221.

Continuous infusion of glucose with model assessment, J.P. Hosker, D.R. Matthews, A.S. Rudenski, M.A. Burnett, P. Darling, E.G. Bown and R.C. Turner, Diabetes Research Laboratories, Oxford, UK, Diabetologia, Springer-Verlag 1985, issue 28, pp. 401-411.

Scholar google search results, Mar. 5, 2008.

Does fall in tissue glucosing precede fall in blood glucose?, F. Sternberg, C. Meyerhoff, F.J. Mannell, H. Mayer, F. Bischof, E.F. Pfeiffer, Institute of Diabetes Technology, Univers Bity of Ulm, Germany, Diabetologia, Springer-Verlag, 1996, issue 39, pp. 609-612.

* cited by examiner

Log Book

Martin Marimba

| Date Time | Item | Value |
|---|---|---|
| 28-May-99 11:43:00 AM | Suspend On | |
| 28-May-99 11:43:00 AM | Download | 507C |
| 28-May-99 11:43:00 AM | Download | Accu-Chek Complete |
| 28-May-99 11:43:00 AM | Bolus | N 0.6U |
| 28-May-99 11:43:00 AM | Bolus | N 1.5U |
| 28-May-99 11:43:00 AM | Meter | 201.0 |
| 28-May-99 11:43:00 AM | Bolus | N 1.2U |
| 28-May-99 11:43:00 AM | Meter | 110.0 |
| 27-May-99 11:43:00 AM | Meter | 46.0 |
| 27-May-99 11:41:00 PM | Bolus | N 1.0U |
| 27-May-99 11:27:00 PM | Bolus | N 2.0U |
| 27-May-99 09:53:00 PM | Meter | 111.0 |
| 27-May-99 09:15:00 PM | Temp Basal | 0.1 U 02:00 |
| 27-May-99 09:05:00 PM | Meter | 87.0 |
| 27-May-99 08:07:00 PM | Meter | 100.0 |
| 27-May-99 07:38:00 PM | Meter | 174.0 |
| 27-May-99 07:15:00 PM | Bolus | D/S 2.0U 01:00 |
| | Bolus | D/N 3.5J |
| | Bolus | N 1.9U |
| | Bolus | N 2.4U |
| | Meter | 216.0 |
| | Download | Accu-Chek Complete |
| | Suspend Off | |
| 27-May-99 04:17:00 PM | | |
| 27-May-99 04:15:00 PM | Suspend On | |

Pump
- ☑ Bolus History
- ☑ Daily Totals
- ☑ Primes
- ☑ Alarms
- ☑ Events
- ☑ Profile Changes
- ☑ All Download Dates

Meter
- ● Glucose Meter Readings
- ○ Glucose Excursions +
- ○ Glucose Excursions −

Sensor
- ☐ Sensor Summary
- ☐ Sensor Events
- ○ Glucose Excursions +
- ○ Glucose Excursions −

1. SELECT ITEMS TO BE DISPLAYED FROM THE LIST ON THE LEFT. SOME SELECTIONS ARE MUTUALLY EXCLUSIVE WITH OTHER SELECTIONS.

2. SELECT REDISPLAY TO DISPLAY YOUR SELECTION.

TABLE OF SELECTED DATA ITEMS IN CHRONOLOGICAL ORDER.

GLUCOSE MEASUREMENTS OUT OF RANGE WILL BE DISPLAYED IN COLOR:
RED:HIGH
YELLOW:LOW

TO QUICKLY CLEAR ALL SELECTIONS CLICK HERE

[Redisplay] [Clear Selections] [Close]

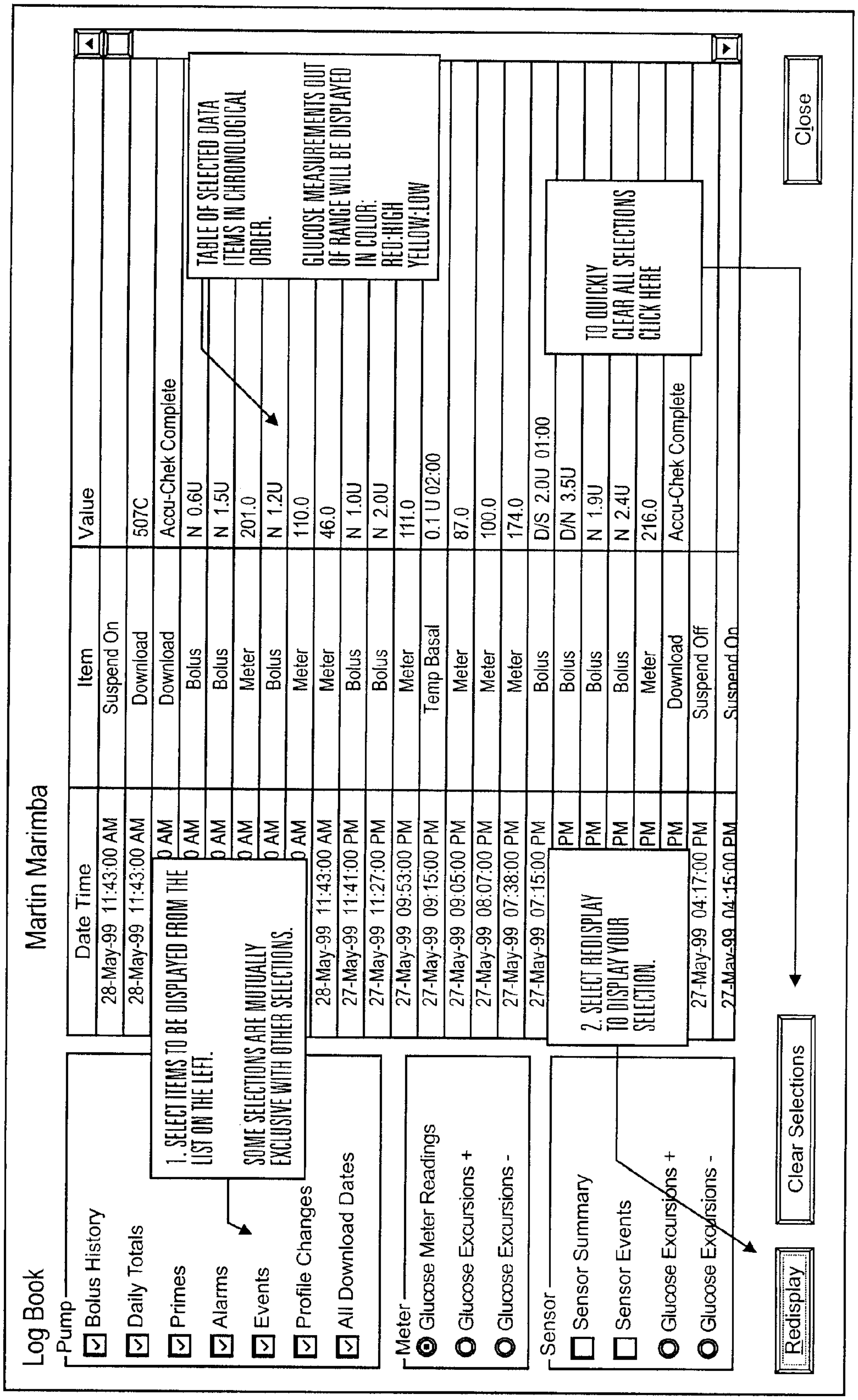

FIG. 16

| Daily Summary | | Martin Marimba | | | | | |
|---|---|---|---|---|---|---|---|
| Date | 27-May-99 | 26-May-99 | 25-May-99 | 24-May-99 | 23-May-99 | 22-May-99 | 21-May-99 |
| Glucose Data Status | | | | | | N | |
| Meter Readings/Day | 8 | 2 | 2 | 4 | N | N/A | 5 |
| Avg. Glucose | 146. | 192. | 209. | 186. | N/A | | 123. |
| Range | | | | | | | |
| Insulin Data Status | | | | | | | |
| Total Insulin | 43.0 | 42.0 | 39.0 | 44.0 | 48.0 | 45.0 | 44.0 |
| | 49% | 54% | 59% | 55% | 46% | 50% | 53% |
| # of Boluses | 9 | 9 | 7 | 9 | 5 | 5 | 8 |
| Prime Volume | 2.6 | | | | 2.3% | | |
| % Time Temp Basal | 8.3% | 8.3% | 6.3% | 0.0% | 0.0% | 8.3% | 0.0% |
| % Time Suspended | 0.5% | 0.0% | 0.0% | 0.0% | 0.0% | 0.0% | 0.0% |

Insulin/Glucose Data Status

| | |
|---|---|
| (Blank) | Data Acquired with no discrepancies/time changes |
| INC | Incomplete Data |
| N | No Data |
| T | Time change has occurred w/o overlap |
| O | Time change has occurred with overlap |

FIG. 23A

Daily Insulin Graph

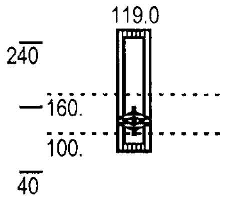

| | |
|---|---|
| 119.0 | Average Weekly Glucose Value |
| -------- | Red: High BG Target |
| -------- | Orange: Low BG Target |

| | |
|---|---|
| | Glucose Range |
| | Average Glucose Value |
| | Standard Deviation |

FIG. 23B

Daily Total Insulin Delivery

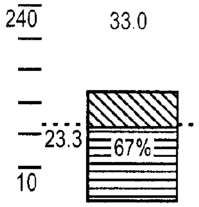

| | |
|---|---|
| 33.0 | Average Daily Total Insulin Delivery |
| -------- | Average Daily Insulin for Previous 91 Days |
| | Green: Average Daily Bolus Delivery |
| | Blue: Average Daily Basal Delivery |

| | |
|---|---|
| 67% | Average Daily Percent of Total Delivered as Basal |
| | Dark Blue: 100% of Daily Total Delivered as Basal (No Bolus Data) |

FIG. 23C

Weekly Insulin Delivery

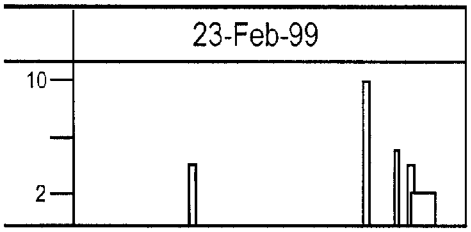

| | |
|---|---|
| | Normal Bolus |
| | Square Wave Bolus |
| | Dual Wave Bolus |
| | Prime |

FIG. 23D

Color Code: Daily Details

Insulin Color Codes

| | |
|---|---|
| | Basal Rate (Dark Blue) |
| | Normal Bolus |
| | Square Wave Bolus |
| | Dual Wave Bolus |
| | Prime |
| | Alarm |
| | Temporary Basal Rate |
| | Suspend |

| | |
|---|---|
| Left Axis | Bolus Delivery Scale |
| Right Axis | Basal Delivery Scale |

Daily Details Pie Chart Color Code

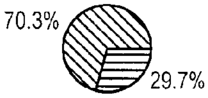

Basal:Bolus

Basal (blue) and Bolus (green) delivery percentages for daily delivery.

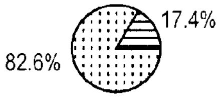

Bolus Type

Daily Bolus Type By Volume: Normal (purple) vs. Square (blue). Dual boluses are split into normal and square components.

FIG. 23E

Color Code: Modal Day

| | |
|---|---|
| — — — | Average Glucose Value for pervious 14 days |
| ......... | Hyperglycemic Level |
| ......... | Hypoglycemic Level |
| Δ | Meter values above 240 mg/dl |
| ☆ | Metered value (colors will vary) |

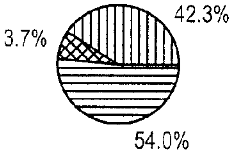

Glucose Goals

Glucose Goals: % readings above (red), below (orange), and within range (aqua) of High and Low GB Targets for date range.

FIG. 23F

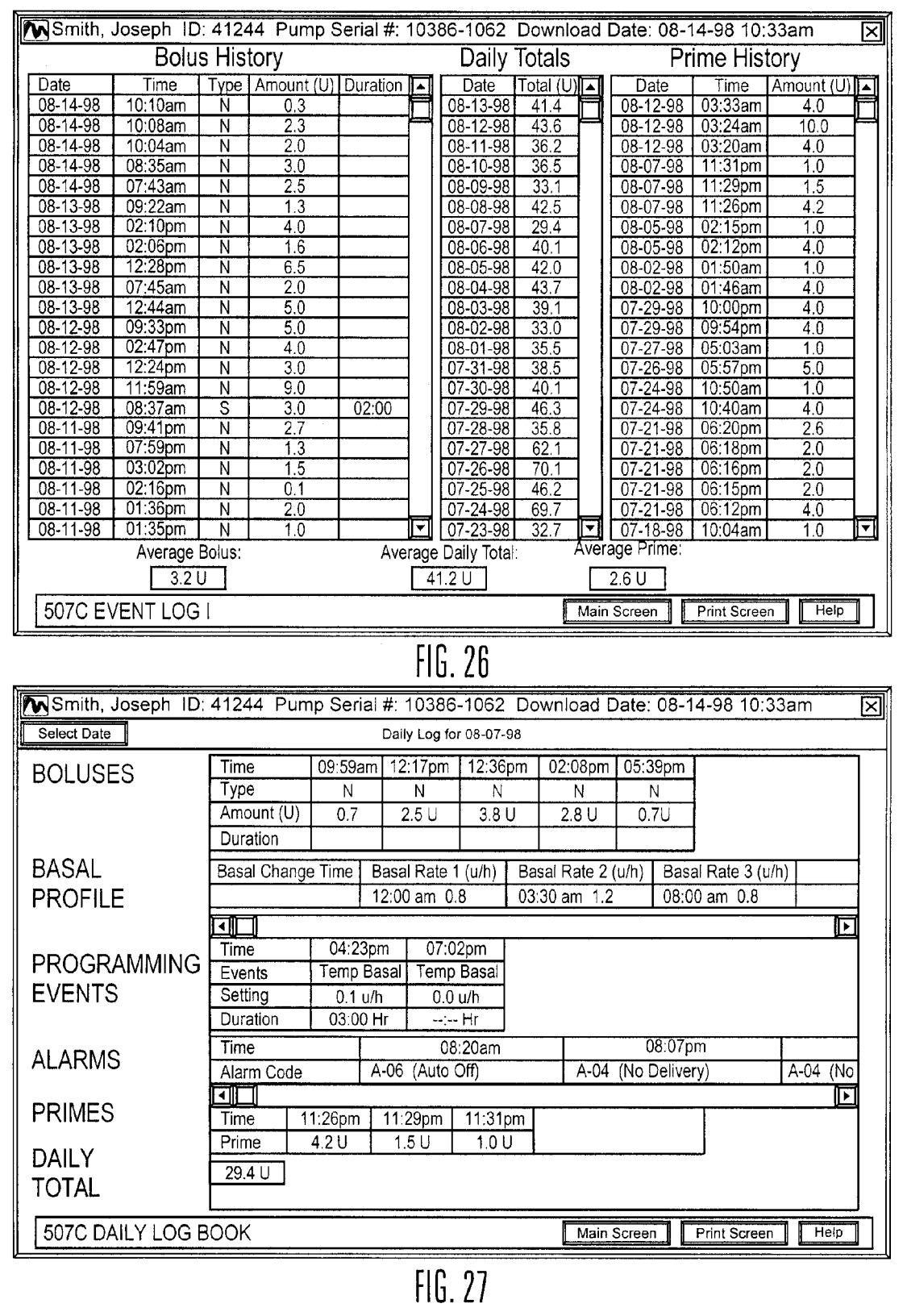

Smith, Joseph ID: 41244 Pump Serial #: 10386-1062 Download Date: 08-14-98 10:33am

Bolus History

| Date | Time | Type | Amount (U) | Duration |
|---|---|---|---|---|
| 08-14-98 | 10:10am | N | 0.3 | |
| 08-14-98 | 10:08am | N | 2.3 | |
| 08-14-98 | 10:04am | N | 2.0 | |
| 08-14-98 | 08:35am | N | 3.0 | |
| 08-14-98 | 07:43am | N | 2.5 | |
| 08-13-98 | 09:22am | N | 1.3 | |
| 08-13-98 | 02:10pm | N | 4.0 | |
| 08-13-98 | 02:06pm | N | 1.6 | |
| 08-13-98 | 12:28pm | N | 6.5 | |
| 08-13-98 | 07:45am | N | 2.0 | |
| 08-13-98 | 12:44am | N | 5.0 | |
| 08-12-98 | 09:33pm | N | 5.0 | |
| 08-12-98 | 02:47pm | N | 4.0 | |
| 08-12-98 | 12:24pm | N | 3.0 | |
| 08-12-98 | 11:59am | N | 9.0 | |
| 08-12-98 | 08:37am | S | 3.0 | 02:00 |
| 08-11-98 | 09:41pm | N | 2.7 | |
| 08-11-98 | 07:59pm | N | 1.3 | |
| 08-11-98 | 03:02pm | N | 1.5 | |
| 08-11-98 | 02:16pm | N | 0.1 | |
| 08-11-98 | 01:36pm | N | 2.0 | |
| 08-11-98 | 01:35pm | N | 1.0 | |

Average Bolus: 3.2 U

Daily Totals

| Date | Total (U) |
|---|---|
| 08-13-98 | 41.4 |
| 08-12-98 | 43.6 |
| 08-11-98 | 36.2 |
| 08-10-98 | 36.5 |
| 08-09-98 | 33.1 |
| 08-08-98 | 42.5 |
| 08-07-98 | 29.4 |
| 08-06-98 | 40.1 |
| 08-05-98 | 42.0 |
| 08-04-98 | 43.7 |
| 08-03-98 | 39.1 |
| 08-02-98 | 33.0 |
| 08-01-98 | 35.5 |
| 07-31-98 | 38.5 |
| 07-30-98 | 40.1 |
| 07-29-98 | 46.3 |
| 07-28-98 | 35.8 |
| 07-27-98 | 62.1 |
| 07-26-98 | 70.1 |
| 07-25-98 | 46.2 |
| 07-24-98 | 69.7 |
| 07-23-98 | 32.7 |

Average Daily Total: 41.2 U

Prime History

| Date | Time | Amount (U) |
|---|---|---|
| 08-12-98 | 03:33am | 4.0 |
| 08-12-98 | 03:24am | 10.0 |
| 08-12-98 | 03:20am | 4.0 |
| 08-07-98 | 11:31pm | 1.0 |
| 08-07-98 | 11:29pm | 1.5 |
| 08-07-98 | 11:26pm | 4.2 |
| 08-05-98 | 02:15pm | 1.0 |
| 08-05-98 | 02:12pm | 4.0 |
| 08-02-98 | 01:50am | 1.0 |
| 08-02-98 | 01:46am | 4.0 |
| 07-29-98 | 10:00pm | 4.0 |
| 07-29-98 | 09:54pm | 4.0 |
| 07-27-98 | 05:03am | 1.0 |
| 07-26-98 | 05:57pm | 5.0 |
| 07-24-98 | 10:50am | 1.0 |
| 07-24-98 | 10:40am | 4.0 |
| 07-21-98 | 06:20pm | 2.6 |
| 07-21-98 | 06:18pm | 2.0 |
| 07-21-98 | 06:16pm | 2.0 |
| 07-21-98 | 06:15pm | 2.0 |
| 07-21-98 | 06:12pm | 4.0 |
| 07-18-98 | 10:04am | 1.0 |

Average Prime: 2.6 U

507C EVENT LOG I — Main Screen | Print Screen | Help

FIG. 26

Smith, Joseph ID: 41244 Pump Serial #: 10386-1062 Download Date: 08-14-98 10:33am Select Date — Daily Log for 08-07-98

BOLUSES

| Time | 09:59am | 12:17pm | 12:36pm | 02:08pm | 05:39pm |
|---|---|---|---|---|---|
| Type | N | N | N | N | N |
| Amount (U) | 0.7 | 2.5 U | 3.8 U | 2.8 U | 0.7U |
| Duration | | | | | |

BASAL PROFILE

| Basal Change Time | Basal Rate 1 (u/h) | Basal Rate 2 (u/h) | Basal Rate 3 (u/h) |
|---|---|---|---|
| | 12:00 am 0.8 | 03:30 am 1.2 | 08:00 am 0.8 |

PROGRAMMING EVENTS

| Time | 04:23pm | 07:02pm |
|---|---|---|
| Events | Temp Basal | Temp Basal |
| Setting | 0.1 u/h | 0.0 u/h |
| Duration | 03:00 Hr | --:-- Hr |

ALARMS

| Time | 08:20am | 08:07pm | |
|---|---|---|---|
| Alarm Code | A-06 (Auto Off) | A-04 (No Delivery) | A-04 (No |

PRIMES

| Time | 11:26pm | 11:29pm | 11:31pm |
|---|---|---|---|
| Prime | 4.2 U | 1.5 U | 1.0 U |

DAILY TOTAL

29.4 U

507C DAILY LOG BOOK — Main Screen | Print Screen | Help

FIG. 27

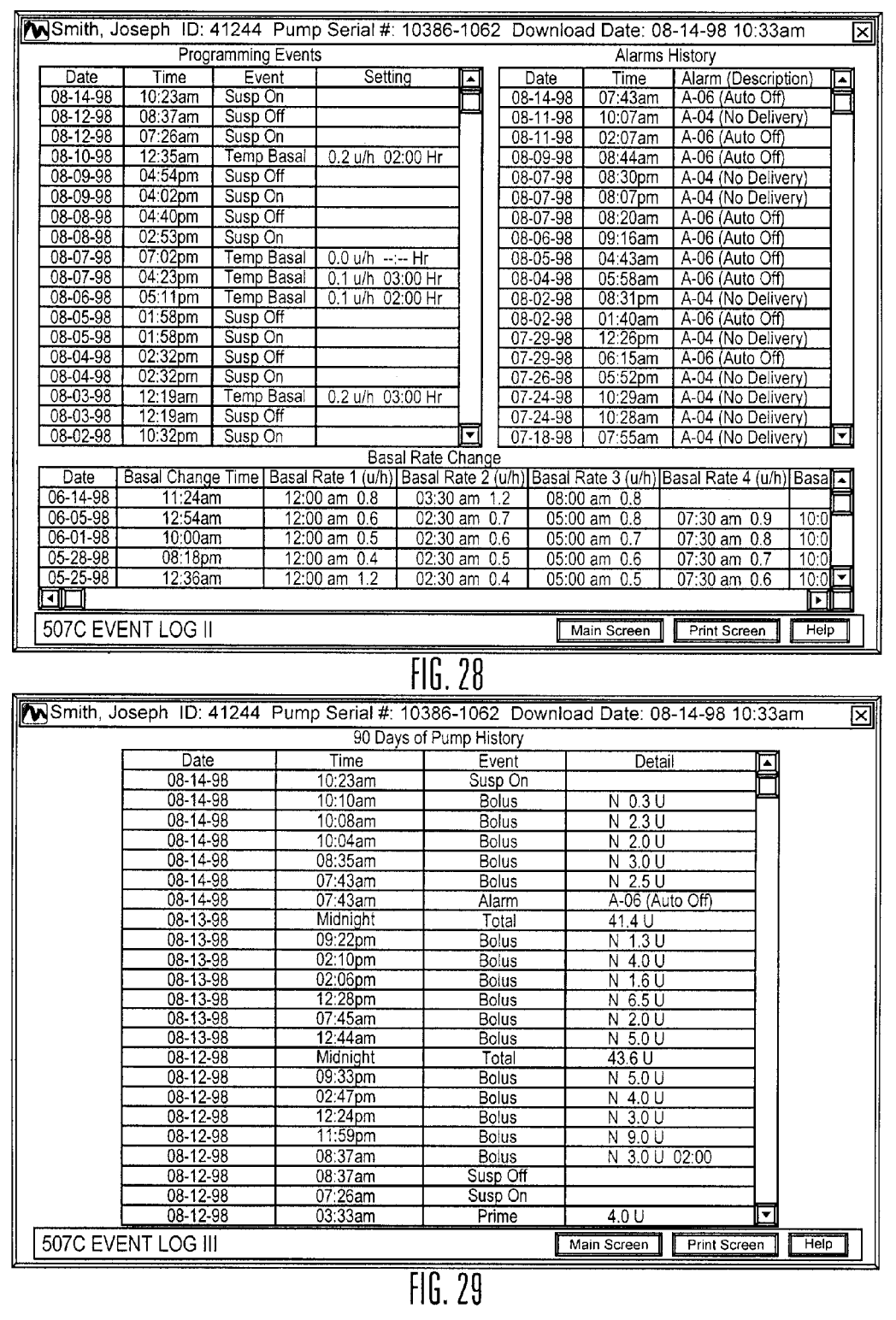

Smith, Joseph ID: 41244 Pump Serial #: 10386-1062 Download Date: 08-14-98 10:33am Programming Events

| Date | Time | Event | Setting |
|---|---|---|---|
| 08-14-98 | 10:23am | Susp On | |
| 08-12-98 | 08:37am | Susp Off | |
| 08-12-98 | 07:26am | Susp On | |
| 08-10-98 | 12:35am | Temp Basal | 0.2 u/h 02:00 Hr |
| 08-09-98 | 04:54pm | Susp Off | |
| 08-09-98 | 04:02pm | Susp On | |
| 08-08-98 | 04:40pm | Susp Off | |
| 08-08-98 | 02:53pm | Susp On | |
| 08-07-98 | 07:02pm | Temp Basal | 0.0 u/h --:-- Hr |
| 08-07-98 | 04:23pm | Temp Basal | 0.1 u/h 03:00 Hr |
| 08-06-98 | 05:11pm | Temp Basal | 0.1 u/h 02:00 Hr |
| 08-05-98 | 01:58pm | Susp Off | |
| 08-05-98 | 01:58pm | Susp On | |
| 08-04-98 | 02:32pm | Susp Off | |
| 08-04-98 | 02:32pm | Susp On | |
| 08-03-98 | 12:19am | Temp Basal | 0.2 u/h 03:00 Hr |
| 08-03-98 | 12:19am | Susp Off | |
| 08-02-98 | 10:32pm | Susp On | |

Alarms History

| Date | Time | Alarm (Description) |
|---|---|---|
| 08-14-98 | 07:43am | A-06 (Auto Off) |
| 08-11-98 | 10:07am | A-04 (No Delivery) |
| 08-11-98 | 02:07am | A-06 (Auto Off) |
| 08-09-98 | 08:44am | A-06 (Auto Off) |
| 08-07-98 | 08:30pm | A-04 (No Delivery) |
| 08-07-98 | 08:07pm | A-04 (No Delivery) |
| 08-07-98 | 08:20am | A-06 (Auto Off) |
| 08-06-98 | 09:16am | A-06 (Auto Off) |
| 08-05-98 | 04:43am | A-06 (Auto Off) |
| 08-04-98 | 05:58am | A-06 (Auto Off) |
| 08-02-98 | 08:31pm | A-04 (No Delivery) |
| 08-02-98 | 01:40am | A-06 (Auto Off) |
| 07-29-98 | 12:26pm | A-04 (No Delivery) |
| 07-29-98 | 06:15am | A-06 (Auto Off) |
| 07-26-98 | 05:52pm | A-04 (No Delivery) |
| 07-24-98 | 10:29am | A-04 (No Delivery) |
| 07-24-98 | 10:28am | A-04 (No Delivery) |
| 07-18-98 | 07:55am | A-04 (No Delivery) |

Basal Rate Change

| Date | Basal Change Time | Basal Rate 1 (u/h) | Basal Rate 2 (u/h) | Basal Rate 3 (u/h) | Basal Rate 4 (u/h) | Basa |
|---|---|---|---|---|---|---|
| 06-14-98 | 11:24am | 12:00 am 0.8 | 03:30 am 1.2 | 08:00 am 0.8 | | |
| 06-05-98 | 12:54am | 12:00 am 0.6 | 02:30 am 0.7 | 05:00 am 0.8 | 07:30 am 0.9 | 10:0 |
| 06-01-98 | 10:00am | 12:00 am 0.5 | 02:30 am 0.6 | 05:00 am 0.7 | 07:30 am 0.8 | 10:0 |
| 05-28-98 | 08:18pm | 12:00 am 0.4 | 02:30 am 0.5 | 05:00 am 0.6 | 07:30 am 0.7 | 10:0 |
| 05-25-98 | 12:36am | 12:00 am 1.2 | 02:30 am 0.4 | 05:00 am 0.5 | 07:30 am 0.6 | 10:0 |

507C EVENT LOG II    Main Screen    Print Screen    Help

FIG. 28

Smith, Joseph ID: 41244 Pump Serial #: 10386-1062 Download Date: 08-14-98 10:33am 90 Days of Pump History

| Date | Time | Event | Detail |
|---|---|---|---|
| 08-14-98 | 10:23am | Susp On | |
| 08-14-98 | 10:10am | Bolus | N 0.3 U |
| 08-14-98 | 10:08am | Bolus | N 2.3 U |
| 08-14-98 | 10:04am | Bolus | N 2.0 U |
| 08-14-98 | 08:35am | Bolus | N 3.0 U |
| 08-14-98 | 07:43am | Bolus | N 2.5 U |
| 08-14-98 | 07:43am | Alarm | A-06 (Auto Off) |
| 08-13-98 | Midnight | Total | 41.4 U |
| 08-13-98 | 09:22pm | Bolus | N 1.3 U |
| 08-13-98 | 02:10pm | Bolus | N 4.0 U |
| 08-13-98 | 02:06pm | Bolus | N 1.6 U |
| 08-13-98 | 12:28pm | Bolus | N 6.5 U |
| 08-13-98 | 07:45am | Bolus | N 2.0 U |
| 08-13-98 | 12:44am | Bolus | N 5.0 U |
| 08-12-98 | Midnight | Total | 43.6 U |
| 08-12-98 | 09:33pm | Bolus | N 5.0 U |
| 08-12-98 | 02:47pm | Bolus | N 4.0 U |
| 08-12-98 | 12:24pm | Bolus | N 3.0 U |
| 08-12-98 | 11:59pm | Bolus | N 9.0 U |
| 08-12-98 | 08:37am | Bolus | N 3.0 U 02:00 |
| 08-12-98 | 08:37am | Susp Off | |
| 08-12-98 | 07:26am | Susp On | |
| 08-12-98 | 03:33am | Prime | 4.0 U |

507C EVENT LOG III    Main Screen    Print Screen    Help

FIG. 29

COMMUNICATION STATION AND SOFTWARE FOR INTERFACING WITH AN INFUSION PUMP, ANALYTE MONITOR, ANALYTE METER, OR THE LIKE

RELATED APPLICATIONS

This is a continuation of U.S. patent application Ser. No. 12/140,157 filed on Jun. 16, 2008, which is a continuation application of U.S. patent application Ser. No. 10/180,732 filed on Jun. 26, 2002, now U.S. Pat. No. 7,647,237 issued Jan. 12, 2010, which is a divisional application of U.S. patent application Ser. No. 09/409,014 filed on Sep. 29, 1999 now abandoned, which claims the benefit of U.S. patent application Ser. No. 60/102,469 filed on Sep. 28, 1998, U.S. patent application Ser. No. 60/121,565 filed Feb. 25, 1999, U.S. Patent Application Ser. No. 60/134,981 filed May 20, 1999, and which is a continuation-in-part of U.S. patent application Ser. No. 29/087,251 filed Apr. 29, 1998, now U.S. Pat. No. D434,142 issued Nov. 21, 2000, all of which are specifically incorporated by reference herein.

FIELD OF THE INVENTION

This invention relates to communication stations for medical devices and, in particular embodiments, to a communication station for use with infusion pumps, analyte monitors/meters such as glucose monitors, glucose meters, or the like.

BACKGROUND OF THE INVENTION

Traditionally, many modern programmable infusion pumps include internal memory for generating and storing data representing actual pump operation over a period of time. The stored data may be reviewed on a periodic basis by medical personnel, so that the patient's condition and treatment regimen can be closely monitored, and the pump reprogrammed as needed. Unfortunately, data retrieval from the infusion pump and/or physician-dictated modification of the basic infusion pump program have required regular patient visits to a medical treatment facility.

To overcome this drawback, raw data has been transferred from an infusion pump to another data storage and/or processing device. An example of a data transfer system for an infusion pump is disclosed in U.S. Pat. No. 5,376,070 issued Dec. 27, 1994 to Purvis et al. and is entitled "Data Transfer System for an Infusion Pump," which is herein incorporated by reference. This device relates to a relatively simple and effective data transfer system that is designed for retrieving data from, and sending program data to, a medication infusion pump. The data transfer system is particularly suited for remote data transfer and/or reprogramming of the infusion pump.

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. In addition, all of these systems are designed to provide data at discrete points and do not provide continuous data to show the variations in the characteristic between testing times. The data representing the results of the test are often stored in a memory of a glucose meter. The data is then downloaded into a computer for later review. However, none of these systems coordinate infusion pump data with the glucose meter data.

Also, these systems generally only download raw data and do not provide for analysis and presentation of the data in a useful format.

SUMMARY OF THE DISCLOSURE

It is an object of an embodiment of the present invention to provide an improved communication station for medical devices, which obviates for practical purposes, the above mentioned limitations.

According to an embodiment of the invention, a communication station is for use with a medical device and a processing device. The communication station includes a housing, a medical device interface coupled to the housing, a processing device interface coupled to the housing and a processor coupled to the housing. The medical device interface interfaces with the medical device, and the processing device interface interfaces with the processing device. The processor provides a communication path between the medical device and the processing device such that programming and instructions may be communicated from the processing device to the medical device and data may be transferred from the medical device to the processing device. In preferred embodiments, the medical device is an infusion pump, analyte monitor, continuous glucose monitor, glucose meter, or the like, and the processing device is a computer. Also, in some embodiments, the medical device interface is a cradle that is configurable to attach to different shaped diabetes related medical devices.

According to an embodiment of the invention, a communication system includes at least one diabetes related medical device, a processing device, and a communication station. The communication station includes a housing, a medical device interface, a processing device interface and a processor. The medical device interface is coupled to the housing and interfaces with the at least one diabetes related medical device. The processing device interface is coupled to the housing and interfaces with the processing device. The processor is coupled to the housing, the medical device interface and the processing device interface to provide a communication path between the at least one diabetes related medical device and the processing device so that programming and instructions may be communicated from the processing device to the at least one diabetes related medical device and data may be transferred from the at least one diabetes medical device to the processing device. In preferred embodiments, the at least one diabetes related medical device is an infusion pump, analyte monitor, continuous glucose monitor, glucose meter, or the like, and the processing device is a computer. Also, in some embodiments, the medical device interface is a cradle that is configurable to attach to different shaped diabetes related medical devices.

In particular embodiments, the processing device uses the data transferred from the at least one diabetes related medical device to generate at least one report based on the transferred data. The at least one report includes infusion pump history and settings, glucose meter history and settings, or both. In further embodiments, the at least one report further includes glucose meter with infusion pump history and glucose monitor history. The at least one report can include tabular and graphical data, as well as statistical analysis, exception reporting, and clinical recommendations based on expert system analysis.

In other embodiments, the processing device interface includes a communication circuit for communicating with the processing device, and the processing device is a remotely located computer. In some embodiments, the remotely controlled computer runs software for a network data management service that utilizes the data transferred from the at least one diabetes related medical device.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIGS. 11(*e*)-11(*s*) show views of icons used as an alternative to the menus shown in FIGS. 11(*a*)-11(*d*).

FIG. 16 is a view of a Log Book display screen used by software in accordance with an embodiment of the present invention.

FIGS. 23(*a*)-(*f*) are views of legends and symbols used in the reports generated by software in accordance with an embodiment of the present invention.

FIG. 26 is a view of an Event Log I display screen used by software in accordance with an embodiment of the present invention.

FIG. 27 is a view of a Daily Log Book display screen used by software in accordance with an embodiment of the present invention.

FIG. 28 is a view of an Event Log II display screen used by software in accordance with an embodiment of the present invention.

FIG. 29 is a view of an Event Log III display screen used by software in accordance with an embodiment of the present invention.

DETAILED DESCRIPTION OF THE PREFERRED EMBODIMENTS

Figure 1:
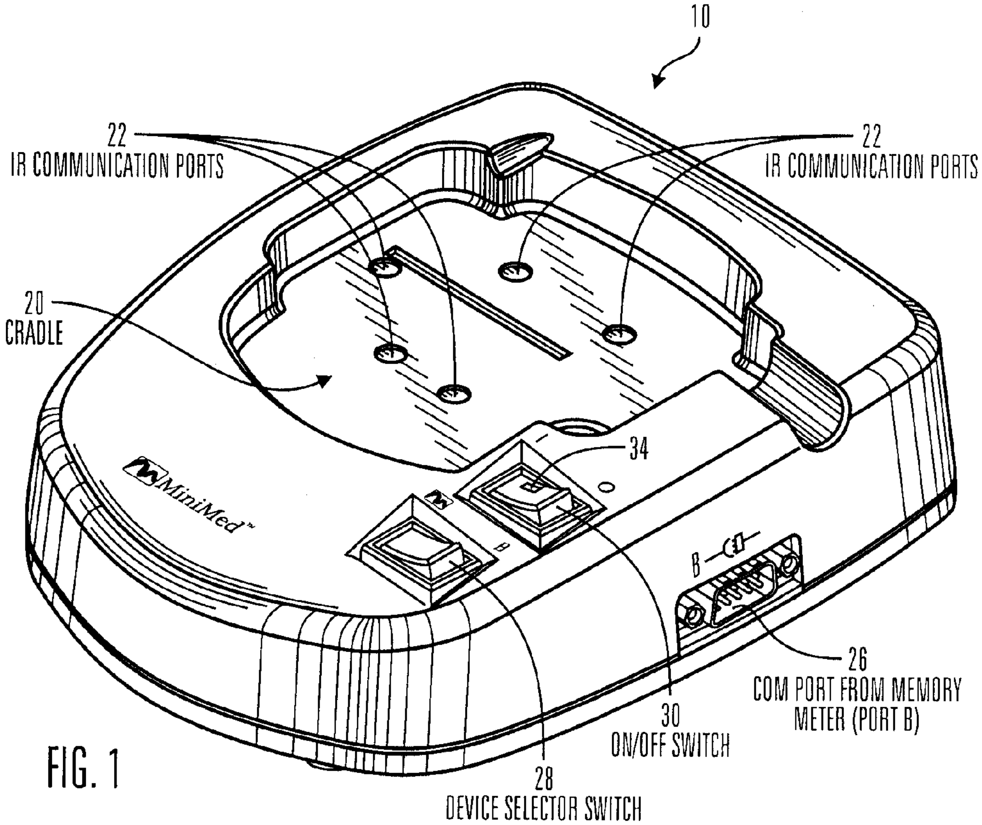
FIG. 1 is a front perspective view of a communication station in accordance with an embodiment of the present invention.

As shown in the drawings for purposes of illustration, the invention is embodied in a communication station for use with an infusion device for infusion of a liquid, such as medication, chemicals, enzymes, antigens, hormones, vitamins or the like, into a body of a user; and a computer, such as a personal computer (PC), laptop, computer, processing device, remote computer, other medical device or the like. In preferred embodiments of the present invention, the infusion device is an external infusion pump; however, it will be recognized that further embodiments of the invention may be used with programmer or data transfer devices for use with external infusion pumps, implantable administration devices, implantable infusion pumps, or the like, or systems that use a combination of implantable and external components. Particular embodiments are directed towards the use in humans; however, in alternative embodiments, the infusion devices may be used in animals. The invention is also embodied in a communication station for use with a glucose monitor system that is coupled to a sensor set to provide continuous, near continuous, or intermittent data recording of the sensor readings for a period of time. In preferred embodiments of the present invention, a glucose sensor and a glucose monitor are used for determining glucose levels in the blood and/or bodily fluids of the user. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the glucose monitor may also include the capability to be programmed to take data at specified time intervals or calibrated using an initial data input received from an external device. The glucose monitor and glucose sensor are primarily adapted for use in subcutaneous human tissue. However, still further embodiments may be placed in other types tissue, such as peritoneal, inter-peritoneal, intraperitoneal, dermal, sub-dermal, subdural, intrathecal, intraventricular, muscle, lymph, organ tissue, veins, arteries or the like, and used in animal tissue. Embodiments may record sensor readings on an intermittent or continuous basis.

As illustrated in FIGS. 1-3 and 32, a communication station 10 is used with an infusion pump 12 to transfer data and information to and from a personal computer (PC) 14. In preferred embodiments, the communication station 10 is connected to the PC 14 through a wired connection to a communication port 16. However, in alternative embodiments, the personal computer may be connected by a wireless connection, a computer network, by modem, or the like. In addition, the PC 14 may be a laptop computer, another medical device with processing capabilities, or the like. In addition, the communication station 10 may work with devices other than an infusion pump 12, such as sensor devices (e.g., a glucose monitor 18), glucose meter 24 or other electronic medical devices. In addition, the communication station may be able to work with different infusion pumps 12 and/or multiple devices at the same time using one or more of the other ports or additional ports.

In preferred embodiments, the infusion pump 12 is connected to the communication station 10 through a cradle holder 20 on the communication station 10 that maintains the position and orientation of the infusion pump 12. This permits the infusion pump 12 to interface with the communication station 10 using an optical communication connection having optical elements 22. In alternative embodiments, the infusion pump 12 may be connected using other methods, such as wired connections, radio connection, contact connections, or the like. In further embodiments, the portion of the communication station 10 that includes the cradle 20 may be replaceable to permit the cradle 20 to be reconfigured to work with other medical devices, such as a glucose meter, RF programmer or data transfer device. In still further alternative embodiments, the optical elements may also be reconfiguarble to work with different devices.

Figure 2:
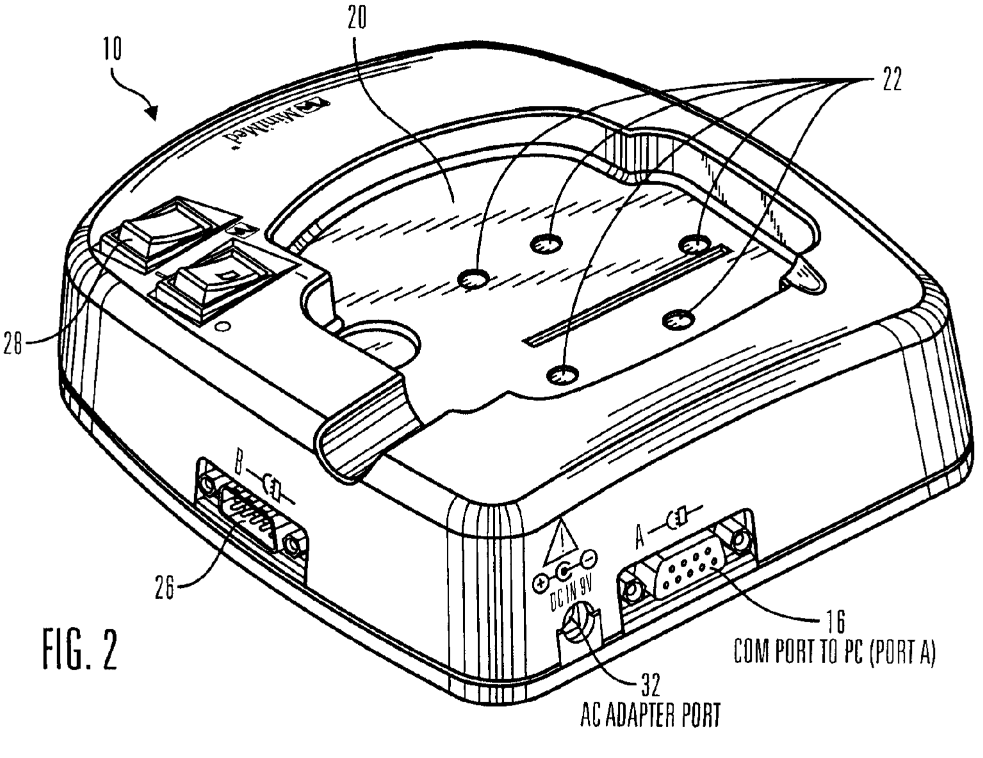
FIG. 2 is a rear perspective view of the communication station shown in FIG. 1.
Figure 3:
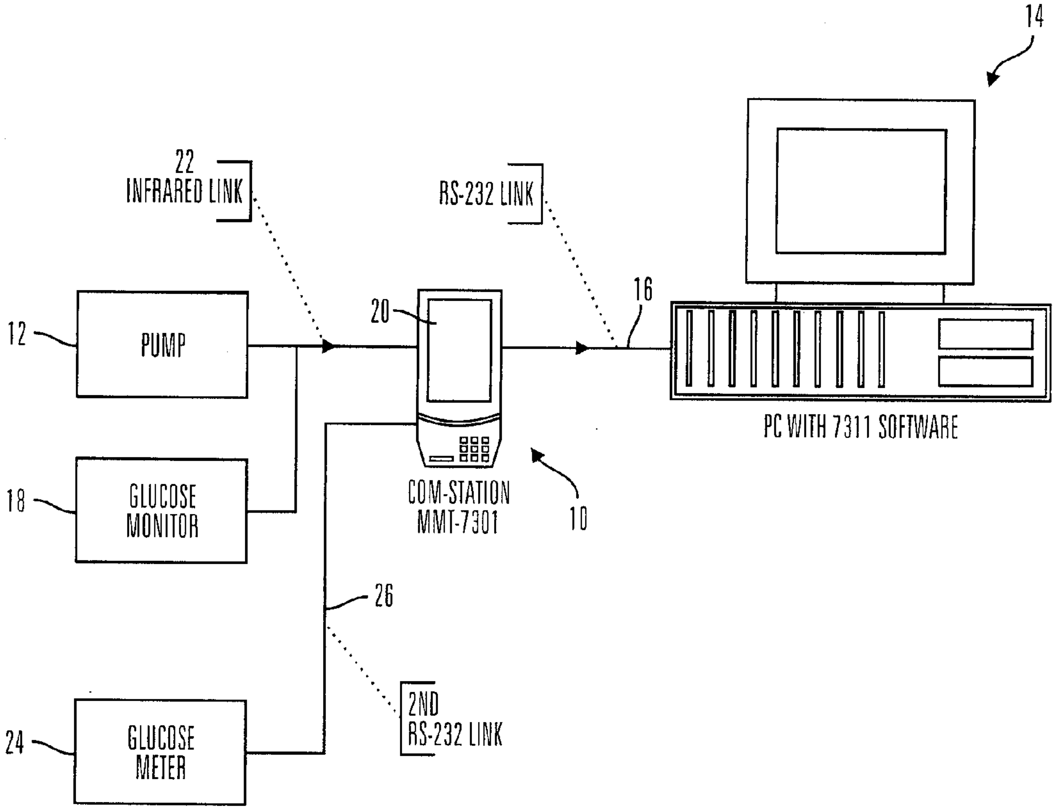
FIG. 3 is a simplified block diagram of a communication station for use with an infusion device, glucose monitor, glucose meter and a personal computer in accordance with an embodiment of the present invention.

As shown in FIGS. 1-3, preferred embodiments of the communication station 10 are designed to work with the MiniMed® model 507, 507C, 508 infusion pumps and future generation infusion pumps by allowing communication between the infusion pumps 12 and a PC 14, laptop, remote computer, data processor, or the like. The software, provided on diskettes or CDs with the communication station 10, will retrieve stored infusion data from the infusion pumps 12 and provide several reports. The reports include text, graphics and key statistics useful for data analysis and interpretation. The user can also download glucose measurement and event data from the MiniMed continuous glucose monitor 18 model MMT-7101 and 7102, and glucose meters 24 such as the Lifescan: One Touch Profile and One Touch II, and the Roche Diagnostics: Accu-chek complete, Accu-chek advantage, and Accu-chek easy. However, in alternative embodiments, the communication station 10 may be used with other infusion pumps, such as those produced or proposed by Disetronic, Animas, or the like, continuous glucose monitors proposed by Therasense, SpectRX, or the like, and glucose meters, such as those made or proposed by Bayer Corporation (such as Glucometer DEX, Glucometer Elite, or the like), Abbot Medisense (such as the Precision QID, or the like), Mercury Diagnostics, or the like. The communication station 10 allows access to the internal memories of the devices specified above. In preferred embodiments, the communication station 10 and software communicates with only one device at a time. However, in alternative embodiments, the communication station 10 and software may communicate with more than one device at a time.

Figure 32:
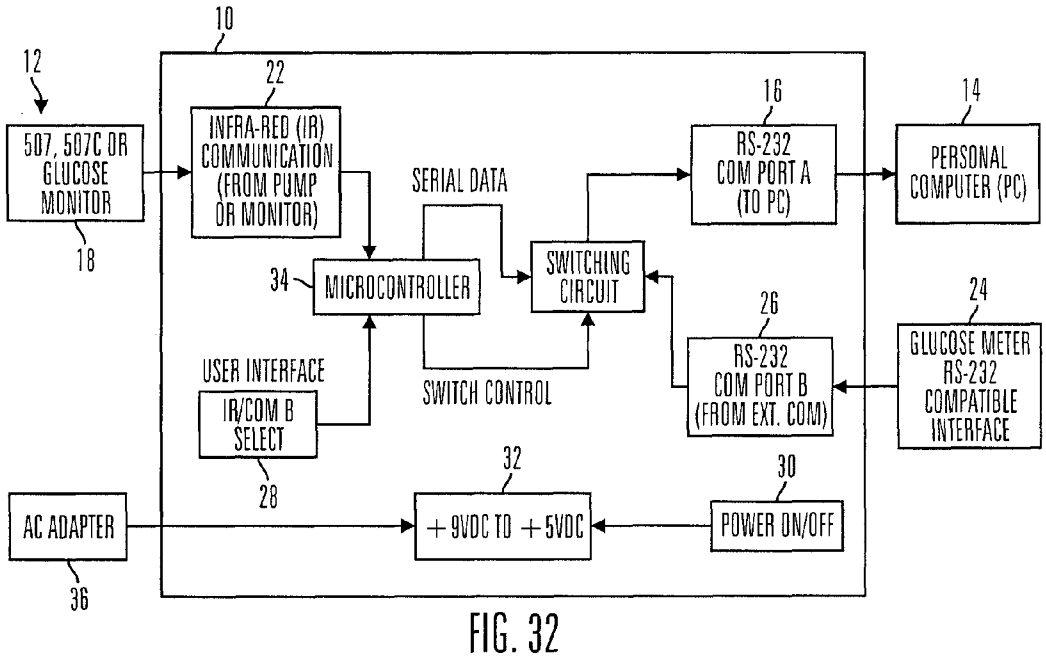
FIG. 32 is a simplified block diagram of a communication station for use with an infusion device, glucose monitor, glucose meter and a personal computer in accordance with another embodiment of the present invention.

As shown in FIGS. 3 and 32, to communicate with the infusion pump 12 (or glucose monitor 18 or meter 24), the communication station and software uses a combination of RS-232 and infrared links. An RS-232 cable through port 16 connects the PC 14 to the communication station 10 and the communication station 10 uses an infrared communication link 22 to the infusion pump 12 (or glucose monitor 18). The device (infusion pump 12, or glucose monitor 18) must be placed on the communication station 10 in order for the software to communicate with the device. To communicate with most glucose meters 24, the communication station 10 and software uses two RS-232 links 16 and 26. The glucose meter 24 is connected to an additional RS-232 port 26 on the communication station 10 and the communication station 10 merely functions as a ‘pass through’ connection between the PC 14 and glucose meter 24. A manually operated switch on the communication station makes this connection. In alternative embodiments, the switch may be automatically activated, such as by detection of a connection with an appropriate device or by a command generated in the PC software. The communication station 10 will enhance communication between a patient and a doctor by allowing the doctor to retrieve glucose monitor data and data regarding the patient’s infusion pump usage.

As shown in FIGS. 1-3 and 32, the communication station 10 includes the following components (see FIGS. 1 and 2). an On/Off Switch 30—The switch is marked by two symbols “O” indicating the device is OFF and “I” indicating the device is ON. A green light 34 illuminates when the communication station is ON. An infusion pump “Cradle” 20—A depression in the communication station where the infusion pump 12 (and/or glucose monitor 18) is placed to download data stored in its memory. The cradle 20 contains infrared (IR) ports 22, which provide a communication link between the infusion pump 12 or glucose monitor 18 and a PC 14 and allow a data download to occur. An AC Adapter Port 32—provides the power supply connection to the communication station. Communication Ports (Com Ports) A and B 16 and 26—using a computer cable, provide a data link between the communication station 10 and a PC 14 (Port A—16) or a memory glucose meter 24 (Port B—26). A Device Selector Switch 28—selects a data download from either a MiniMed infusion pump 12 or a memory glucose meter 24 (B). A push-button or rocker selector 28 switch will select between IR communication 22 (COM Port A connected to IR) and COM Port B 26 (COM Port A connected COM Port B). Preferably, the PC software will not control the selection of using either the IR port 22 or second RS-232 port 26. However, alternative embodiments may include a remote setting switch that allows for remote selection of whether the IR port 22 or the second RS-232 port 26.

The communication station 10 shall be designed to ensure that the IR ports 22 are insensitive to ambient light so that the presence of ambient light will not cause a device malfunction by interference with the IR communication transceivers 22. When infusion pump 12 is placed in the communication station 10 cradle 20, two (2) infrared (IR) ports (not shown) on the back side of the infusion pump 12 align with two (2) ports on the communication station 10. Data is then transferred from the infusion pump 12 using these IR ports 22. Preferably, the communication station 10 uses at least two Infra-Red (IR) communication transceiver sets 22 on each communication station 10. One IR transceiver set 22 is positioned to communicate with the infusion pumps 12 described above, and the other one IR transceiver set 22 is positioned to communicate with the glucose monitor 18.

The communication station 10 will also have two RS-232 compatible serial communication ports 16 and 26; one female DB9 (To PC) 16, which is identified as COM Port A, and one female DB9 (pass-through) 26, which is identified as COM Port B. In preferred embodiments, a serial cable to connect the communication station to the PC 14 will be provided with the communication station 10. The cable will have a female DB9 end to connect to the PC 14 and a male DB9 end to connect to the communication station 10 (COM Port A—16). In alternative embodiments, the male and female connectors of the communication station and the cable may be interchanged.

The communication station 10 will use a microcontroller 34 to support the communication between the infusion pump 12 or glucose monitor 18 and the PC 14. Preferred embodiments of the communication station 10 software will include circuitry, modems or the like, that supports communication at baud rates from 1024, 1200 up to 19200 Baud. However, in alternative embodiments, lower rates to 100 Baud and higher rates to several MegaBaud may be used, with the selection being dependent on the type, the amount of data, and the location that the data is downloaded to.

There will be firmware (embedded software) used in the communication station 10. This firmware will contain the means to support communications with the infusion pump 12 or glucose monitor 18 and of translating to serial information. In preferred embodiments, communication protocols necessary to communicate with the infusion pump 12 or glucose monitor 18 will be contained in the communication station 10 firmware. However, in alternative embodiments, the communication protocols may be loaded into a RAM, other suitable memory device, a CD, or the like.

Preferably, the communications link with the infusion pump 12 or glucose monitor 18 will not be initiated by the communication station 10 firmware until communications with the PC software has been established and the appropriate command has been received. Preferably, the software to communicate to the communication station 10 will reside in the host PC 10. However, in alternative embodiments, the software may reside in the communication station 10, infusion pump 12, glucose monitor 18 and/or glucose meter 24. The PC software will establish the communication link with the communication station 10. The PC software will send the commands to initiate the downloading of the appropriate data to a text file which will be stored on the PC 14. It will also create reports and graphs. In alternative embodiments, a remote computer may be utilized to establish a communication link and may request user confirmation at the communication station to confirm the establishment of the communication link. The PC software will be Windows 95-compatible. However, alternative embodiments may be compatible with future versions of Windows, UNIX, LINUX, DOS, Mac OS, OS2, or the like.

Preferably, the communication station shall not require any calibration. In addition, other than periodic cleaning of the device, no maintenance shall be required particularly in the area of the infra-red components. It is critical to the operation of the communication station 10 that the infra-red clear lenses protecting the receiving and transmitting elements 22 be maintained in an optically clear condition. The communication station 10 shall be designed to allow cleaning with a soft cloth or paper towel and commonly used household and clinical cleansing agents. Cleaning requirements and chemical resistance will conform to AAMI TIR No. 12-1994 Annex A.

As shown in FIGS. 3 and 32, to use the communication station 10, connect the communication interface cable, which is supplied with the communication station 10, into either the "COM 1" or "COM 2" connector of the PC 14. Connect the other end of the Communication Interface Cable to the "COM A" port 16 of the communication station 10. Connect the power cable with AC Adapter 36 into to the communication station 10 and connect the other end to a power source. Depress the power switch 30 so that it points to "I". A green light 34 on this switch 30 will glow when the communication station 10 is receiving power and is turned ON. With the connections established and power supplied, the communication station 10 is now ready to download the data stored in the infusion pump 12 or glucose monitor 18. Alternative embodiments may utilize other PC communication architectures including, but not limited to, SCSI, network, IR links, or the like.

Figure 5:
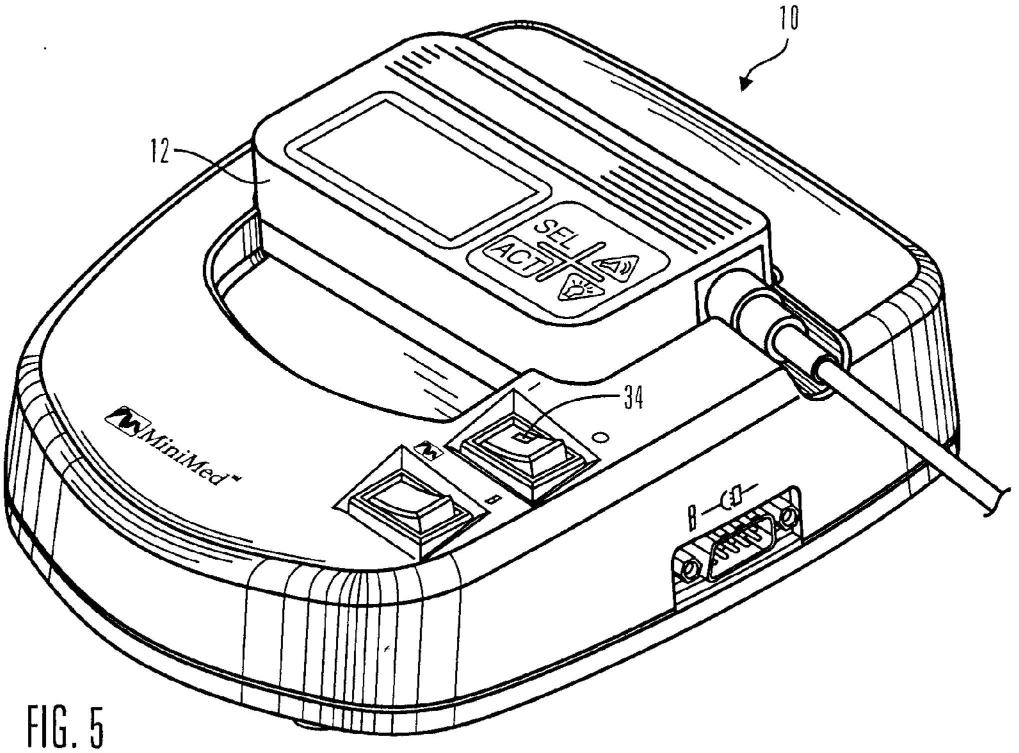
FIG. 5 is a perspective view of an infusion pump mounted in the cradle of the communication station shown in FIG. 1.

Press the Device Selector Switch 28 on the communication station 10 to indicate that a cradle 20 loadable device will be used. Place the infusion pump 12 face up (so that you are looking at the infusion pump display) into the communication station 10 cradle 20 (see FIG. 5). Make sure that the infusion pump 12 is lying flat and snugly in the cradle 20. This will line up the IR communication ports of the infusion pump 12 and the IR communication ports 22 of the communication station 10. If a glucose monitor 18 is to be used, the glucose monitor 18 is seated in the cradle 20 (see FIG. 6). The infusion pump (or glucose monitor 18) can now be accessed by the PC software on the PC 14.

Figure 4:
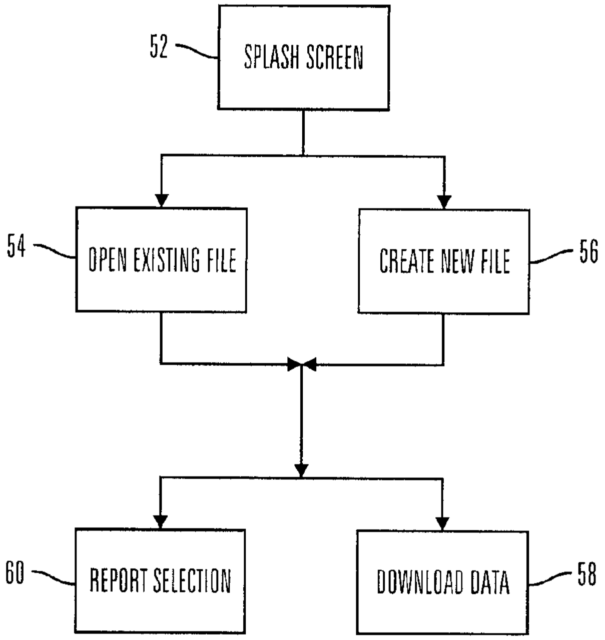
FIG. 4 is a simplified block diagram illustrating a basic software flow structure used by an embodiment of the present invention.

FIG. 4 illustrates the basic system flow for the PC software used to control the communication station 10. The software starts with a splash screen 52 to inform the user of the software title and version. Next the user selects either an existing patient data file 54 or creates a new patient data file 56. After selection of the appropriate data file, the user selects whether to download new information 58 or to generate reports 60 based on previously downloaded data. The following sections will discuss the various software functions, screens and reports.

As discussed above, the software on the PC 14 will display a Splash Screen 52 after opening the application. The Splash Screen 52 will include the following characteristics: logo, such as the MiniMed logo, or the like; title, such as “Communications and Data Analysis Software Version x.x”, or the like; subtitle, such as “For Use with MiniMed 507, 507C, and 508 Insulin Pumps, MiniMed Glucose Monitor 7101 and 7102, and Glucose Meters (Accuchek, OneTouch)”, or the like; additional subtitles such as “Copyright YYYY/MiniMed Inc./All Rights Reserved”, or the like; and a button such as “OK”, or the like, to indicate an understanding of the window. In alternative embodiments, more or less information and/or buttons may be added to the splash screen 52.

Figure 8:
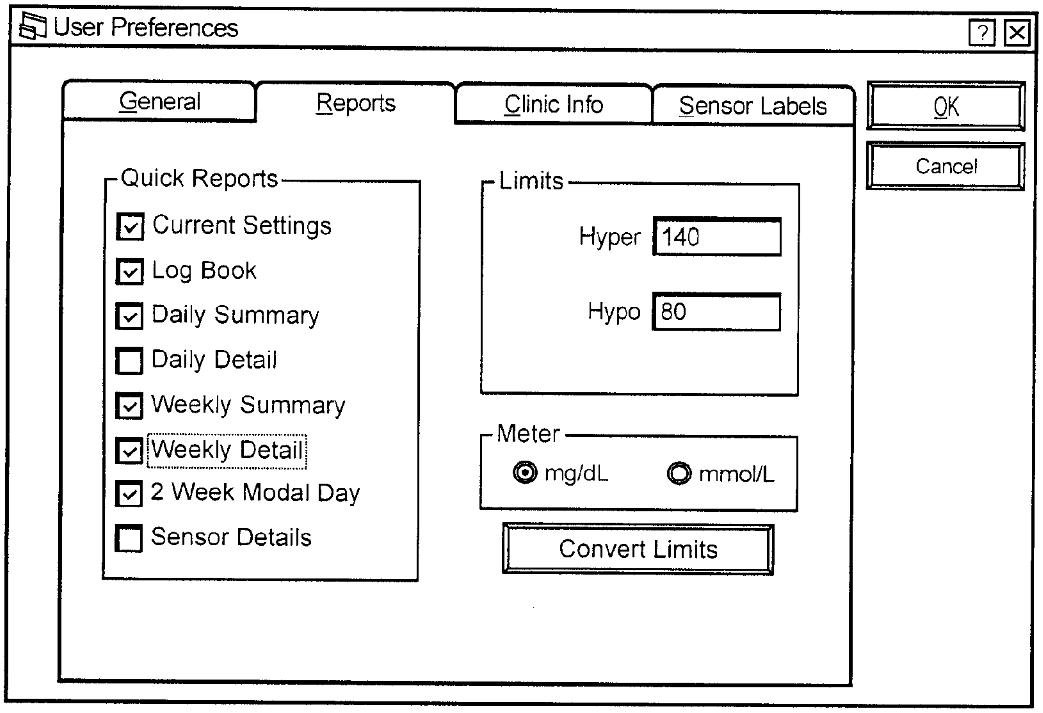
FIG. 8 is a view of a Report User Preferences display screen of used by software in accordance with an embodiment of the present invention.
Figure 9:
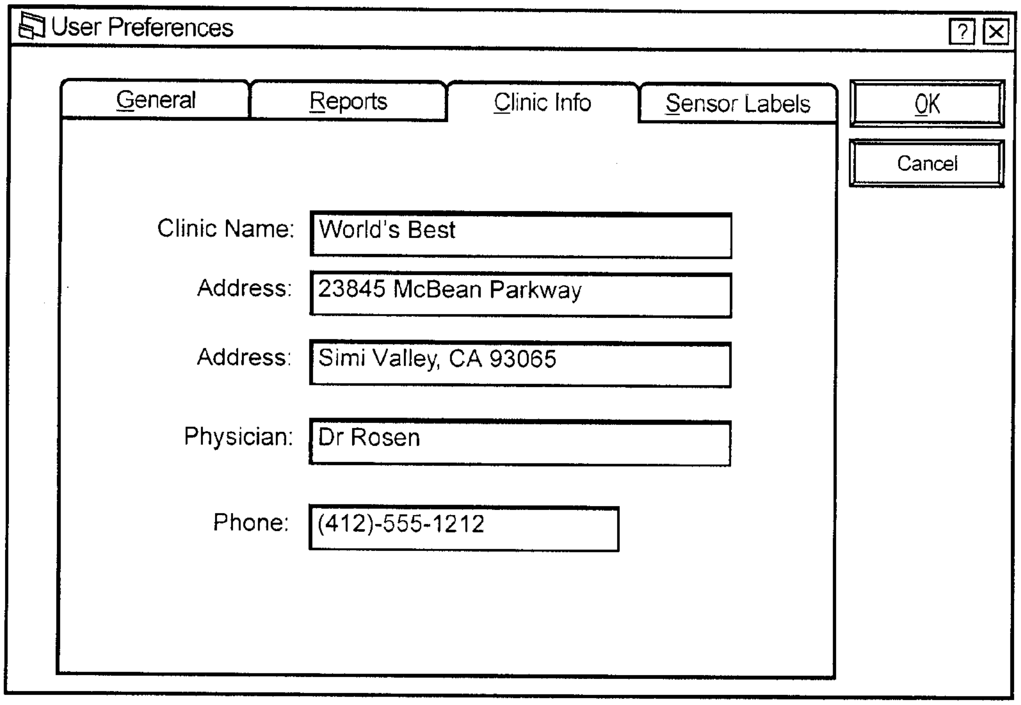
FIG. 9 is a view of a Clinic Info User Preferences display screen of used by software in accordance with an embodiment of the present invention.
Figure 10:
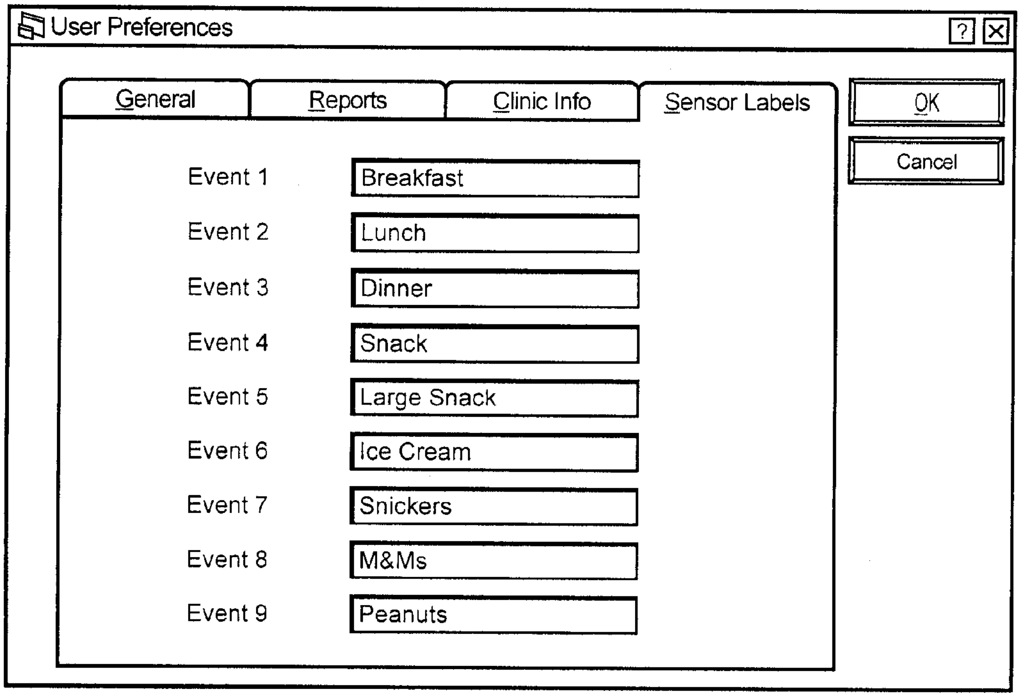
FIG. 10 is a view of a Sensor Labels User Preferences display screen of used by software in accordance with an embodiment of the present invention.
Figure 11A:
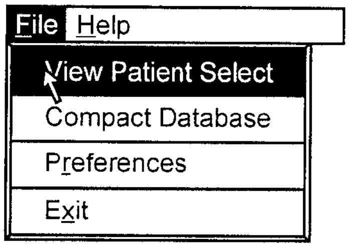
FIGS. 11(*a*)-11(*d*) show views of various menus used by software in accordance with an embodiment of the present invention.
Figure 11B:
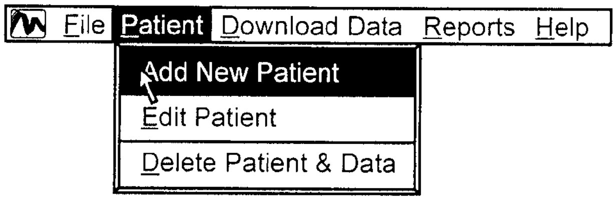
Figure 11C:
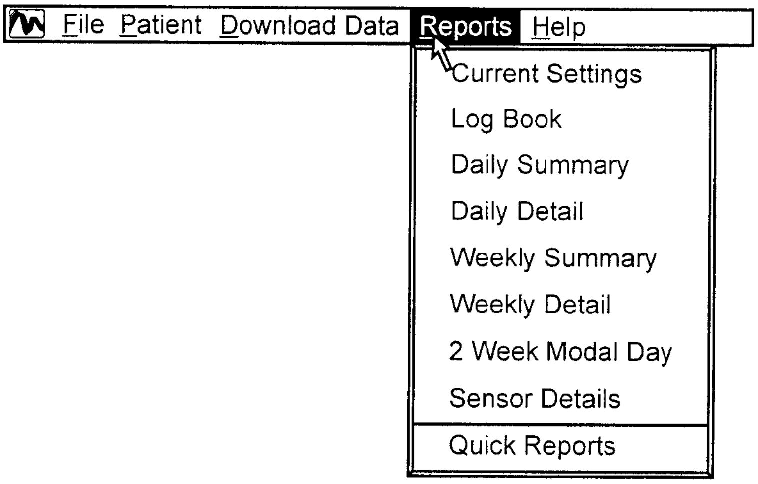
Figure 11D:
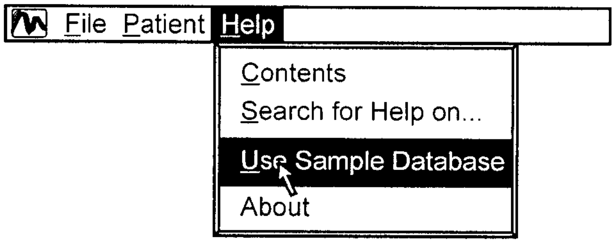
Figure 11E:
Figure 11F:
Figure 11G:
Figure 11H:
Figure 11I:
Figure 11J:
Figure 11K:
Figure 11L:
Figure 11M:
Figure 11N:
Figure 11O:
Figure 11P:
Figure 11Q:
Figure 11R:
Figure 11S:

When the user initiates the software for the first time, or needs to reconfigure the software to reflect changes in the medical device, patient information, or the like, the user accesses the User Preferences Screen, as shown in FIGS. 7-10, through a menu such as shown in FIG. 11(*a*). This User Preferences Screen allows the user to setup various parameters and data for the facility and parameters that are common to all patients. The User Preferences screen consists of four parts, or sub-screens: General (FIG. 7), Reports (FIG. 8), Clinic Info (FIG. 9), and Sensor Labels (FIG. 10). Additional preferences and screens may be used, with the selection being dependent on the software requirements, the user’s needs and the type of data analysis to be performed.

Figure 7:
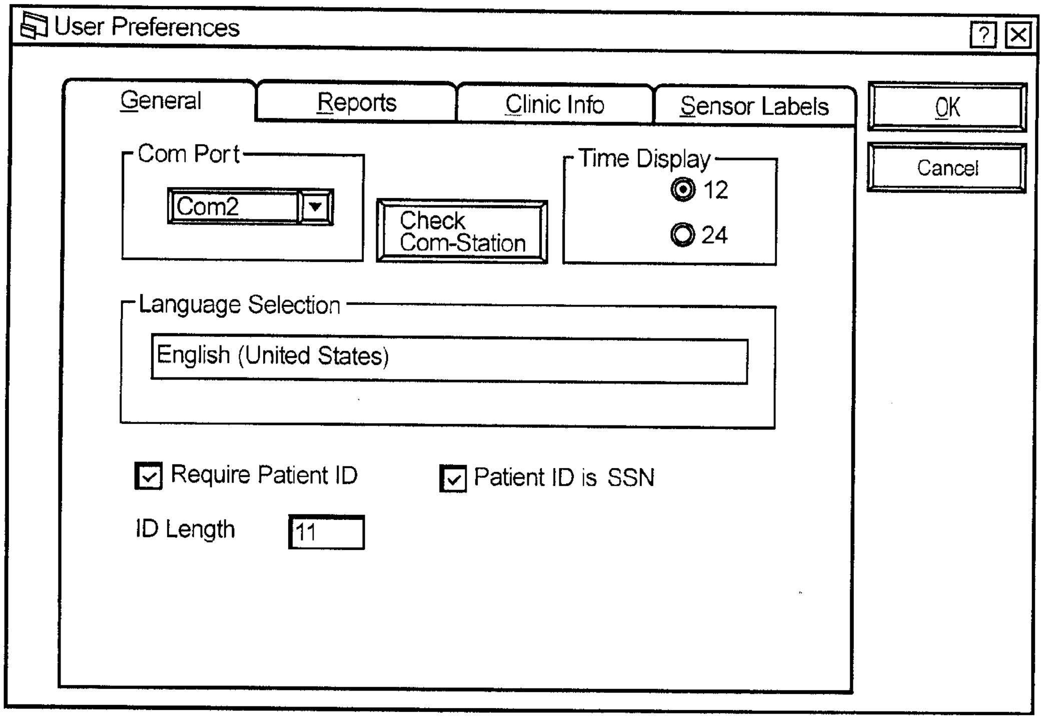
FIG. 7 is a view of a General User Preferences display screen used by software in accordance with an embodiment of the present invention.

As shown in FIG. 7, the General screen allows the input of: Com Port selection (i.e. Com1, 2, 3, or 4) to use with the communication station 10, Language Selection (American English, Int. English, Dutch, French, German, Italian, Spanish, and Swedish) to use for communicating with the user of the software, selection of ‘Mandatory Patient ID’ to identify each patient, selection of the Patient ID Length to use with the software, and specification of whether Patient ID is to be the patient’s SSN (i.e., social security number).

As shown in FIG. 8, the Reports screen allows the input of: enabling of specific Quick Reports (including Current Settings, Pump History, Daily Summary, Daily Detail, Weekly Summary, Weekly Detail, Modal Day, & Sensor Details), specification of Hyperglycemic and Hypoglycemic limits, and selection of the units to be used for the meter measurements.

As shown in FIG. 9, the Clinic Info screen allows the input of clinical information including: Clinic Name (or name of the medical office, hospital, or the like), the Address, the physician (or internist, endocrinologist, clinician, or the like), and the Phone Number.

As shown in FIG. 10, the Sensor Labels screen allow the specification of names of Sensor Labels associated with and representative of various glucose monitor events inputted by the user.

Figure 12:
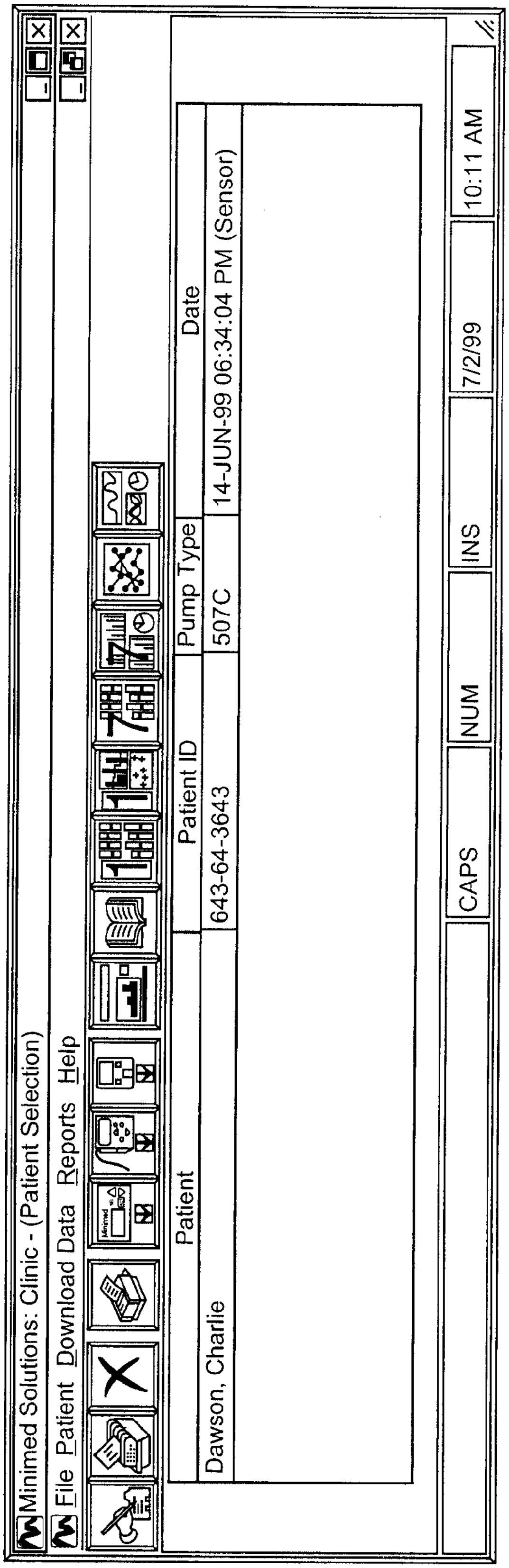
FIG. 12 is a view of a Patient Selection display screen used by software in accordance with an embodiment of the present invention.
Figure 13:
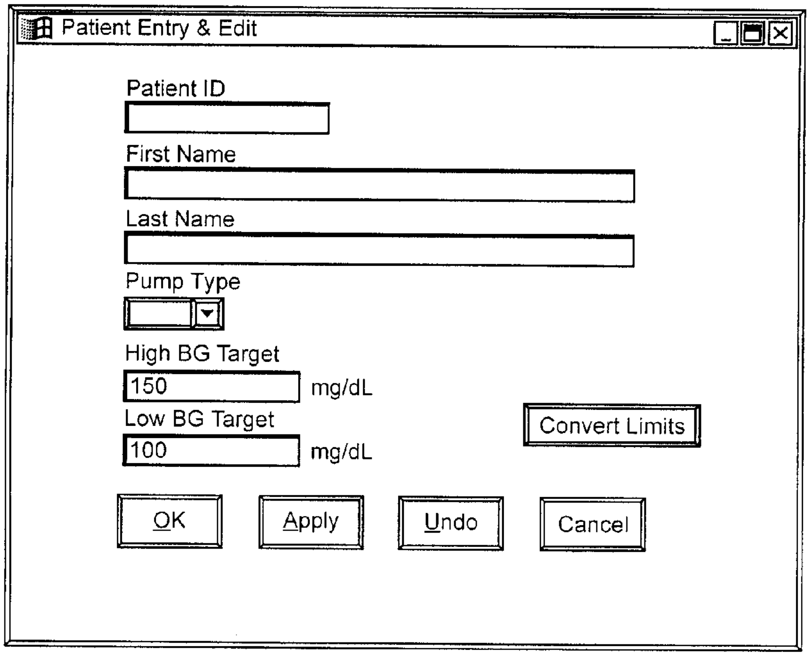
FIG. 13 is a view of a Patient Entry and Edit display screen of used by software in accordance with an embodiment of the present invention.

To use the communication PC software requires the selection of a patient under which to download data and/or analyze data. To select a patient, the user will click on the appropriate patient name that is listed in a Patient Selection window, such as shown in FIG. 12. If there is no patient, or if another patient record is required, the user will need to create a new patient record to associate downloaded data with that patient (or another patient selected before downloading). FIG. 11(*b*) shows an example of a menu that is used to access a Patient Entry and Edit screen. Alternatively, the user may click on the icon in FIG. 11(*e*) for a new patient or the icon of FIG. 11(*f*) for editing an existing patient. FIG. 13 shows the Patient Entry & Edit screen used to create a new patient record or edit existing information in a patient record. The Patient Entry & Edit screen allows entry and editing of patient name, patient ID (such as a unique number, social security number or the like) and infusion pump type (e.g., brand and model number). As shown in FIG. 13, the screen also allows entry and editing of individual patient hyperglycemic and hypoglycemic levels, and permits the user to select glucose levels to be displayed in either Mg/dL or mmol/L, without the necessity of the user going to the User Preferences window. In alternative embodiments, the Patient Entry & Edit screen may also be used for the input of additional information, such as glucose monitor information, glucose meter information, additional patient specific information, or the like. Some information is inputted by typing in the information, some by selecting from a list. In alternative embodiments, the information may be inputted by other methods, such as checking off selected parameters or by toggling a softkey on the screen. If a duplicate Patient ID is entered, the PC software will detect this and require the user to enter another ID. Alternatively, software may determine duplication on the patient’s name, or the like.

As shown in FIG. 11(*b*), the software shall also allow the user to delete individual patients and all data associated with those patients. This is accomplished by selecting the patient from the list shown in FIG. 12, and then selecting delete on the menu in FIG. 11(*b*). Preferably, the software shall require the user to confirm the deletion of the patient record and associated data. Following a successful delete data operation, the specified patient name (i.e. the patient selected on the Patient Selection screen) will no longer appear on the Patient Selection screen. In alternative embodiments, the information for that patient will be maintained for possible later recall, or sent to a long term data storage area. In that situation, to actually delete specific information may require the use of a special screen or additional program. In alternative embodiments, the use may select the icon 11(*g*) instead of the menu 11(*b*)

Once a patient record has been created, the Patient Selection screen, as shown in FIG. 12, is used to specify a patient for subsequent operations. Before a new device data can be downloaded or before any report can be viewed, the user must first select a patient. To select a patient from a list, the patient name portion of the selected patient is highlighted. In addition, subsequent edit patient, delete patient, download and report display operations shall be for this selected patient until another patient is selected. Preferred embodiments of the Patient Selection screen format include the following displayed information for each patient such as Patient name, Patient ID, Pump Type, and Date of most recent download. The list of patients on the Patient Selection screen is preferably sortable by any of the displayed information such as Patient name, Patient ID, Pump Type, or Date. In alternative embodiments, the Patient Selection screen may include other information such as glucose monitor type, glucose meter type, doctor, facility, or the like, and may be sortable by this additional information. If a patient uses more than one type of infusion pump, glucose monitor, glucose meter, or the like, so that a patient has a history of downloads from at least two different devices, such as both 507 and 507C infusion pumps, only the most recently device (e.g., a 507C infusion pump) downloaded shall be displayed on the screen.

The download operation consists of transferring data to the PC 14 (or other data storage and/or processing device) from the following medical devices such as infusion pumps 12, monitors 18, and meters 24. To download data from a medical device, the user can select the appropriate menu under the download heading shown in FIGS. 11(*a*)-(*d*), or use the infusion pump download icon (shown in FIG. 11(*i*)) to download the infusion pump 12, the glucose monitor download icon (shown in FIG. 11(*j*)) to download the glucose monitor 18, or the glucose meter download icon (shown in FIG. 11(*k*)) to download the glucose meter 24. The downloaded data will be saved in the currently selected patient's record in the data base. In alternative embodiments, the user may be able to direct the data to be saved to a different patient record or storage area. The user shall be notified of any download errors encountered. If possible, the download operation will provide an error recovery capability, which is particularly useful in conjunction with a lengthy download operation. Preferably, during the download operation, a download screen will be displayed with the patient name, device type and model number. In addition, a progress bar indicator will be displayed to indicate the status of the download. In alternative embodiments, more or less information may be displayed. Generally, following a successful download operation, the message "Download completed successfully. Save data?" shall be displayed. The user is then prompted Yes/No." The download screen will permit the user to cancel the download operation, either during the download operation or prior to the final saving of the data.

Downloading for infusion pumps includes the process of transferring appropriate data from the infusion pump 12 to the PC 14. Typical stored information, which is downloaded from an infusion pump 12 are current pump settings, daily totals and boluses, events, and alarms. The downloaded infusion pump data is integrated in the reports with glucose monitor 18 and glucose meter 24 data that has been previously or later downloaded (see discussion below). The infusion pump download operation will be initiated by either the Pump Download icon (see FIG. 11(*i*)) or via the menu bar (see FIGS. 11(*a*)-(*d*)). Preferably, the infusion pump download operation automatically determines the infusion pump model number (e.g. 507, 507C or 508, or the like) and uses the appropriate communication protocol for the particular infusion pump. Generally, the transfer time runs from several seconds to 20 minutes, with the time being dependent on the type of infusion pump, and the amount and the type of data stored in the infusion pump. In preferred embodiments, the user will be prompted to verify infusion pump settings following completion of the download. Specifically, the AutoOff duration should be reset and Suspend of the infusion pump should be canceled. In addition, after successfully completing the download operation, the downloaded infusion pump data will be integrated with any previously downloaded data for the specified patient. In alternative embodiments, the user may be given the option to replace or discard the previous data with the newly downloaded data, or the ability to only integrate portions of the data based on dates, times, type of data, or the like.

The communication station PC software checks for several differences during the download operation. For instance, the software checks for a Time/Date difference during the download operation by comparing the time and date in the infusion pump 12 with the time and date in the PC 14. If a difference of >5 minutes exists, the user will be notified with a message indicating the existence of the mismatch and the time and date for each device. The user then will be asked to select which time and date should be used and given the option to reset the time and date on the infusion pump. In alternative embodiments, different time differences may be used to prompt the user. The PC software also checks for an infusion pump serial number difference between the previous download, and then if noted, the software will alert the user and offer the options of either CANCEL or PROCEED. In addition, the software will check for a time overlap, such as by a clock change, and then if it is noted, the program shall offer the following options: CANCEL download, PROCEED (and discard older overlapping data), PROCEED (and discard newer overlapping data). Alternative embodiments may check for other differences or changes during the download operation.

Downloading for glucose monitors 18 includes the process of transferring appropriate data from the glucose monitor 18 to the PC 14. The glucose monitor download will be initiated from either the Menu bar (see FIGS. 11(*a*)-(*d*)) or via the glucose monitor download icon (see FIG. 11(*j*)). Typical stored information, which is downloaded from a glucose monitor 18, includes sensor readings, event markers, and manually entered glucose readings (e.g., for reference and calibration). In alternative embodiments, more or less data and information may be transferred. Generally, the transfer time runs from several seconds to 20 minutes, with the time being dependent on the type of glucose monitor 18, the amount and the type of data stored in the glucose monitor 18. The glucose monitor download operation will include an ERROR RECOVERY (the infusion pump operation may also include this feature) which allows the communication station software to retry the download operation if an error is detected. In addition, after successfully completing the download operation, the downloaded glucose monitor data will be integrated with any previously downloaded data for the specified patient. In alternative embodiments, the user may be given the option to replace and/or discard the previous data with the newly downloaded data, or the ability to only integrate portions of the data based on dates, times, type of data, or the like.

Downloading for glucose meters 24 includes the process of transferring appropriate data from the glucose meter 24 to the PC 14. The glucose meter download will be initiated from either the Menu bar (see FIGS. 11(*a*)-(*d*)) or via the glucose monitor download icon (see FIG. 11(*k*)). Typical stored information, which is downloaded from a glucose meter 24, includes time stamped glucose readings, current clock settings, event markers, or the like. Preferably, the glucose meter download operation automatically determines the glucose meter type and model (e.g. Roche Accuchek Vs Johnson & Johnson One Touch, or the like) and uses the appropriate communication protocol for the particular glucose meter. Generally, the transfer time runs from several seconds to 20 minutes, with the time being dependent on the type of glucose meter, the amount and the type of data stored in the glucose meter 24. In addition, after successfully completing the download operation, the downloaded glucose meter data will be integrated with any previously downloaded data for the specified patient. In alternative embodiments, the user may be given the option to replace and/or discard the previous data with the newly downloaded data, or the ability to only integrate portions of the data based on dates, times, type of data, or the like.

The communication station PC software provides several data display and print options for the user to better analyze and sort the data downloaded for each patient. For instance, the PC software provides user-selectable displays (e.g., reports, and the like) and printouts of infusion pump 12, glucose meter 24 and glucose monitor 18 (i.e., sensor) data in accordance with the display screens and reports shown in FIGS. 14-29. Preferably, the user shall be provided with the capability of selecting any display or printout for any period prior to the last download date/time. In particular embodiments, the selected report (display or printout) shall contain up to 91 days of data prior to and including the selected download date/time. Note that the report may also contain data from a different download date and time to fill the 91 day period. Alternatively, the report may only cover a specific period or fraction within the downloaded data or may include more or less than 91 days.

Figure 14:
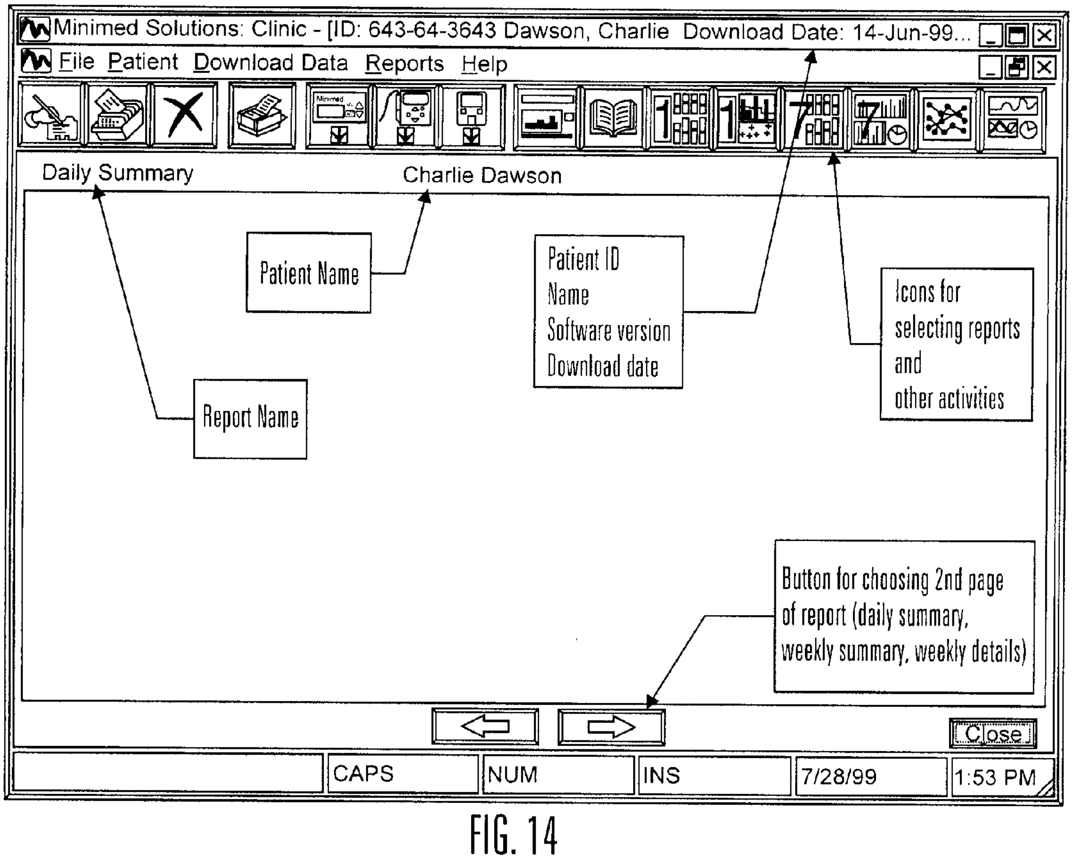
FIG. 14 is a view of a Report display screen used by software in accordance with an embodiment of the present invention.

FIG. 14 illustrates the general display structure used by the reports generated by the software. The report form will include a CLOSE Command Button that undisplays (removes) the individual report when the user is done with that report. The report form will display a Help menu to provide context-sensitive help for the selected report (see FIG. 11(*d*)). If the report includes more than one screen, arrow buttons (generally located at the bottom of the screen) will provide for moving back and forth between the multiple screens.

A report is selected for display via either the standard Windows menu (e.g. under reports—see FIG. 11(*c*)) or via the communication station 10 toolbar (using report icons—see FIGS. 11(*l*)-11(*s*)). The active-inactive state of a toolbar icon is context sensitive to the patient's specific infusion pump type, glucose monitor type, and glucose meter type. Accordingly, some Report Icons (and menu selection options) are inactive for some infusion pumps, glucose monitors and glucose meters. It should be noted that additional reports may be generated, with the following reports serving to illustrate various reporting abilities. During the report generation process, the following labels (see FIG. 23(*a*)) may be used to express various data status issues:='Inc'=incomplete data (there is some data but it is clear that some data is missing); 'N'=no data is present; 'T'=a time change has occurred w/o overlap; and 'O'=a time change has occurred with overlap. In addition, where appropriate, the x-axis shall be displayed in either a 12 or 24 hour format depending on the User Preference screen setting. FIG. 14 illustrates and describes various other aspects of the general report screen. Although not shown in these reports, the reports may also include facility information such as Physician Name, Address (facility), and Phone Number (facility).

Figure 15:
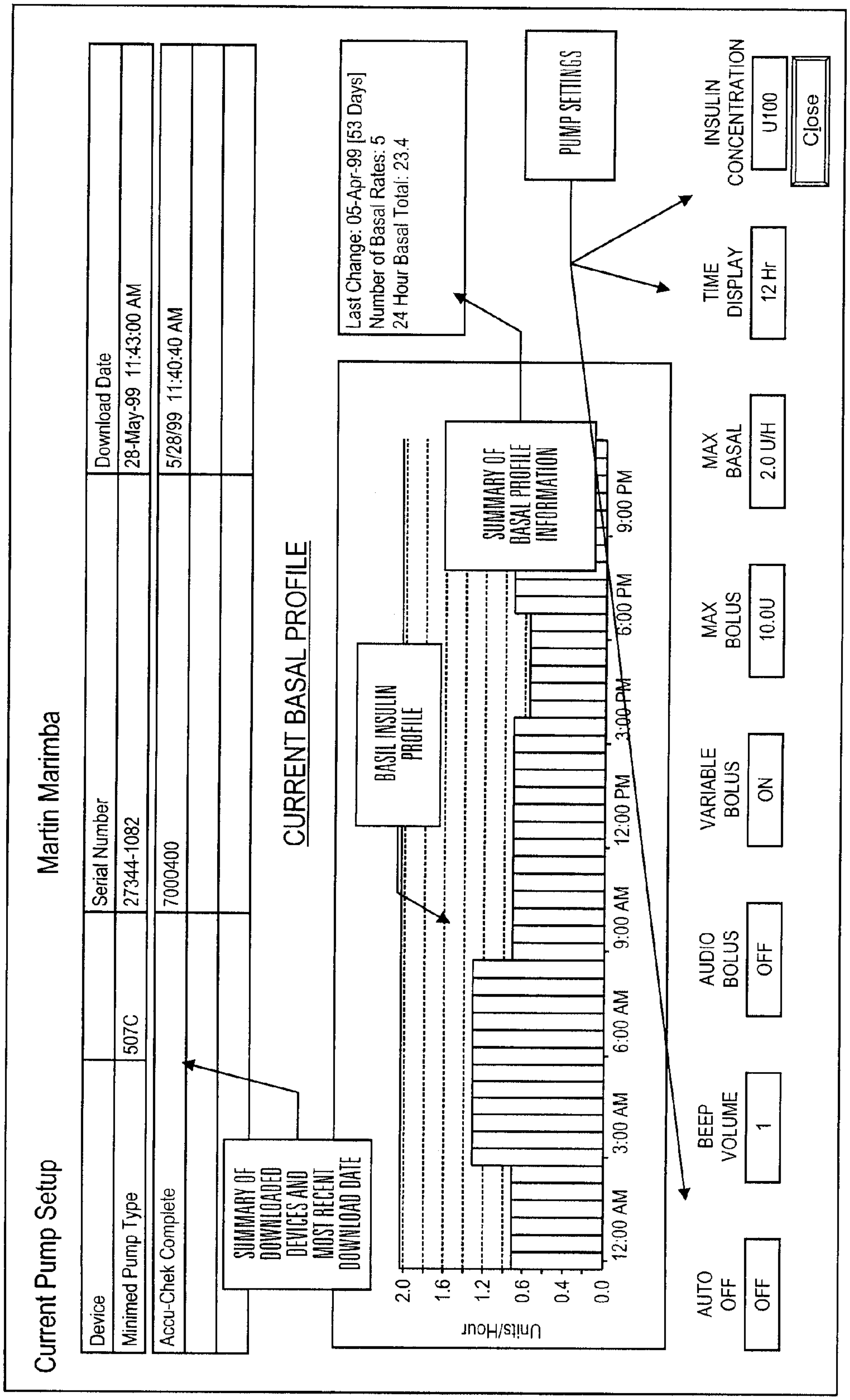
FIG. 15 is a view of a Current Pump Setup display screen used by software in accordance with an embodiment of the present invention.

FIG. 15 illustrates the Patient Information/Current Pump Settings Report, which is selectable by the icon shown in FIG. 11(*l*). This report will have the following components:

1) the Device Table section lists the devices that have been previously downloaded into the selected patient's file. The table includes for each previously downloaded device: the device name, serial number, and most recent download date. The devices listed in the Device Table shall be: infusion pump(s), monitor(s), and meter(s). For each device type (e.g. infusion pump), there may be either none, one, or multiple instances listed. Preferably, this section of the report shall be of variable length and shall be scrollable. If infusion pump data is present, the infusion pump settings listed in report shall be displayed at the bottom of the report. If multiple infusion pumps are listed, the settings of only the infusion pump most recently used shall be displayed.
2) the Current Basal Profile section, if infusion pump data is present, will show the current 24 hour Basal Profile as a continuous line and/or bar graph over 24 hours. Units/hour shall be depicted on the Y axis, with the values preferably automatically scaled with the highest value equal to the next highest whole unit above the highest basal rate setting. In addition, it is preferred that the time in hours will be depicted on the x axis with 12 am, 3 am, 6 am 9 am, 12 noon, 3 pm 6 pm, 9 pm and 12 am markers indicated. Also, faint horizontal lines will be present across the graph at 0.2 unit increments up to a maximum of 5.0 units/hour. If the total exceeds 5.0 units, the scale will switch to 0.5 unit increments. Other units, time values or axis labeling may be used.
3) statistics on the profile will also be provided and include the number of basal rates (rates/day), the total basal insulin (U/day), the date the basal rate was last changed (date), and the umber of days since the profile was changed.

The software shall have the ability to display Current Infusion Pump Setup information as shown in Table 1 below:

TABLE 1

Pump Setting Display Format

| Parameter | Units | Range |
|---|---|---|
| Auto Off | Hr—Hour | Off, Hour setting |
| Beep Volume | N/A | 1, 2, 3 |
| Audio Bolus | U—Units | Off, or 'increment step level' |
| Variable Bolus | N/A | On, Off |
| Max Bolus | U—Units | 0.0-25.0 Units |
| Max Basal | U/H—Units per hour | 0.0-35.0 Units per hour |
| Time Display | N/A | 12 Hr, 24 Hr |
| Insulin Concentration | N/A | U40, U50, U100 |

FIG. 16 illustrates the Log Book report, which is selectable by the icon shown in FIG. 11(*m*). This is a chronological report that integrates infusion pump 12, glucose monitor 18, and glucose meter 24 data. The report will provide a vertically scrolling table with 3 columns (Date-Time of data entry, Item explaining data, and Value of data) for a user specified period. Generally, this is for the most recent 91 days of data in descending order; however, longer or shorter periods may be used. The user may tailor the content using the check boxes listed on the side of the report, and which are segregated by Pump, Meter and Sensor (or Monitor). Check boxes shall be provided to allow the user to select any combination of the following items to display in the table: Pump Data includes bolus history, prime history, daily insulin totals, alarms, programming events, and basal profile changes; Glucose Meter data includes glucose measurements and excursions; and glucose monitor data includes sensor data, sensor summary (mean, minimum and maximum for each hour of sensor use), sensor excursions (all sensor values outside limits hourly sensor summary defined in the User Preferences screen), sensor data (every sensor reading, at 5 min intervals), sensor event markers (with labels as defined in specified patient User Preferences screen). In alternative embodiments, other parameters may be provided and selected.

Figure 17:
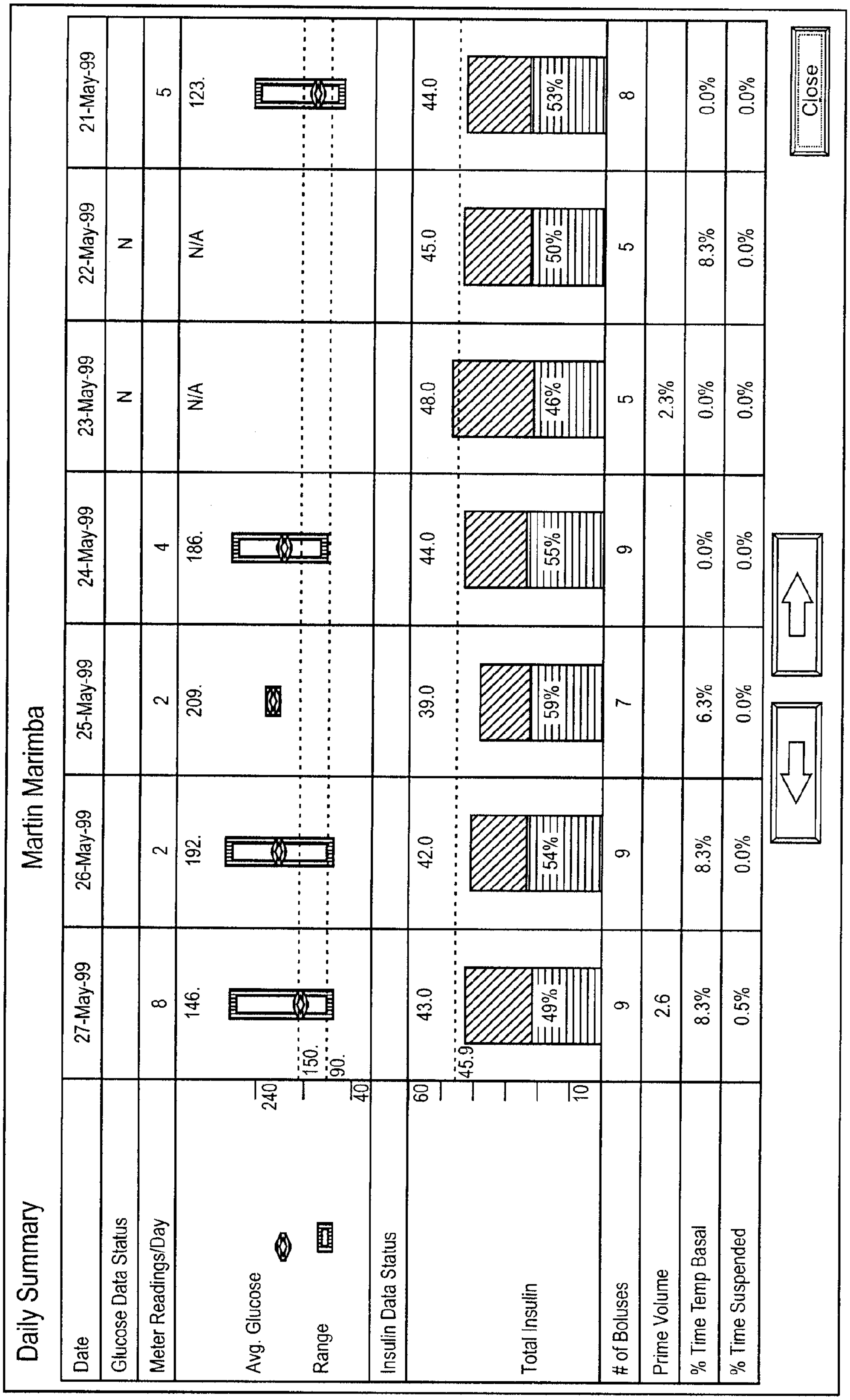
FIG. 17 is a view of a Daily Summary display screen used by software in accordance with an embodiment of the present invention.

FIG. 17 illustrates the Daily Summary report screen, which is selectable by the icon shown in FIG. 11(*n*). This report provides a summary of information relating to the glucose data status and insulin data status for a particular day. Alternatively, it may provide a report for several days in a summary format as shown. The glucose data status section shows the number of readings, the average glucose value and the range. The insulin data status section shows total amount of insulin taken, the number of boluses, the prime volume, the percent of the time that a temporary basal rate was used, and the percent of time that the infusion pump operation was suspended. This report is similar to the report shown in FIGS. 19(*a*)-(*d*) below, but summarizes on a daily basis rather than a weekly basis.

Figure 18A:
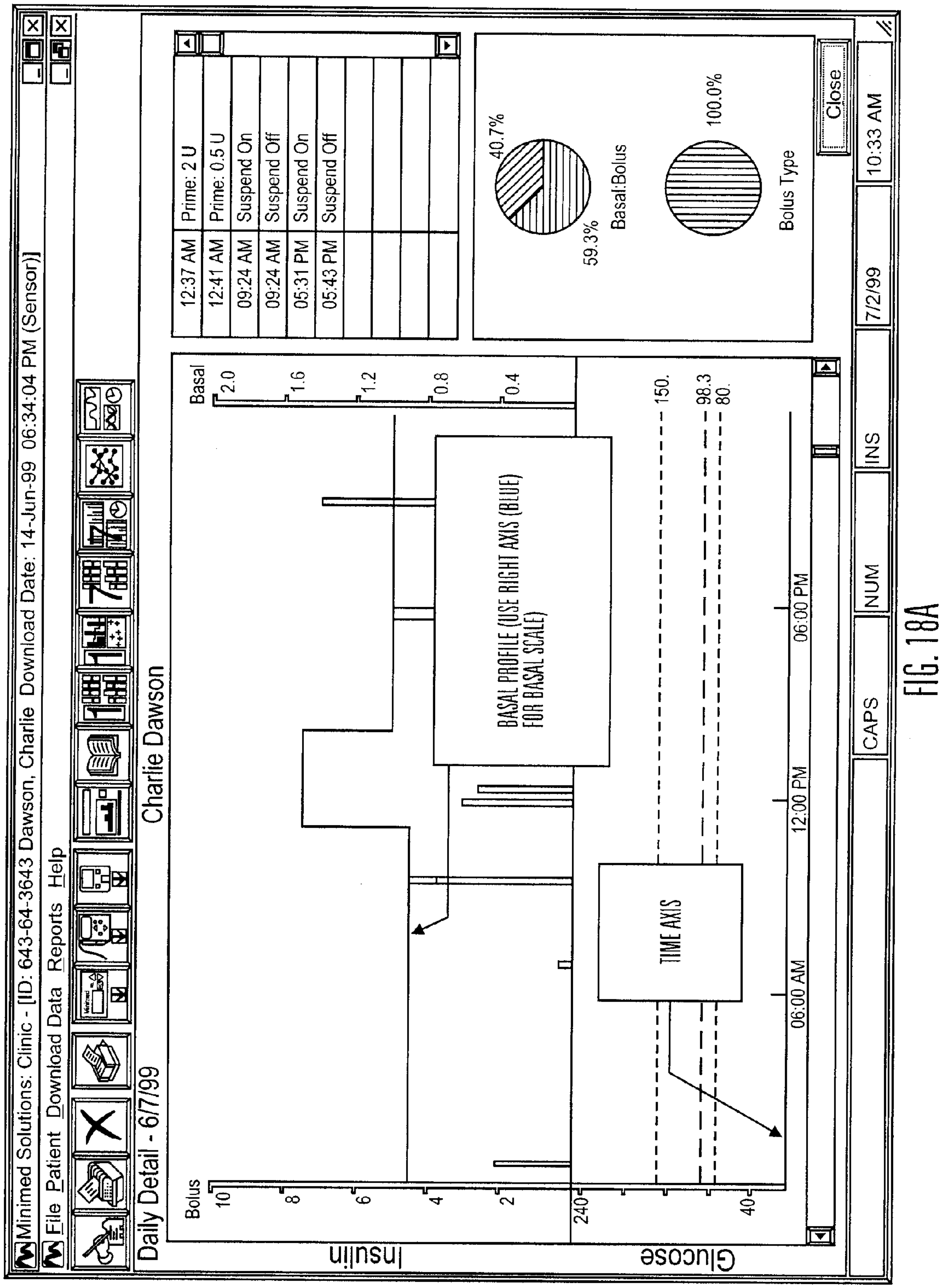
FIGS. 18(*a*)-(*c*) are views of a Daily Detail display screen used by software in accordance with an embodiment of the present invention.
Figure 18B:
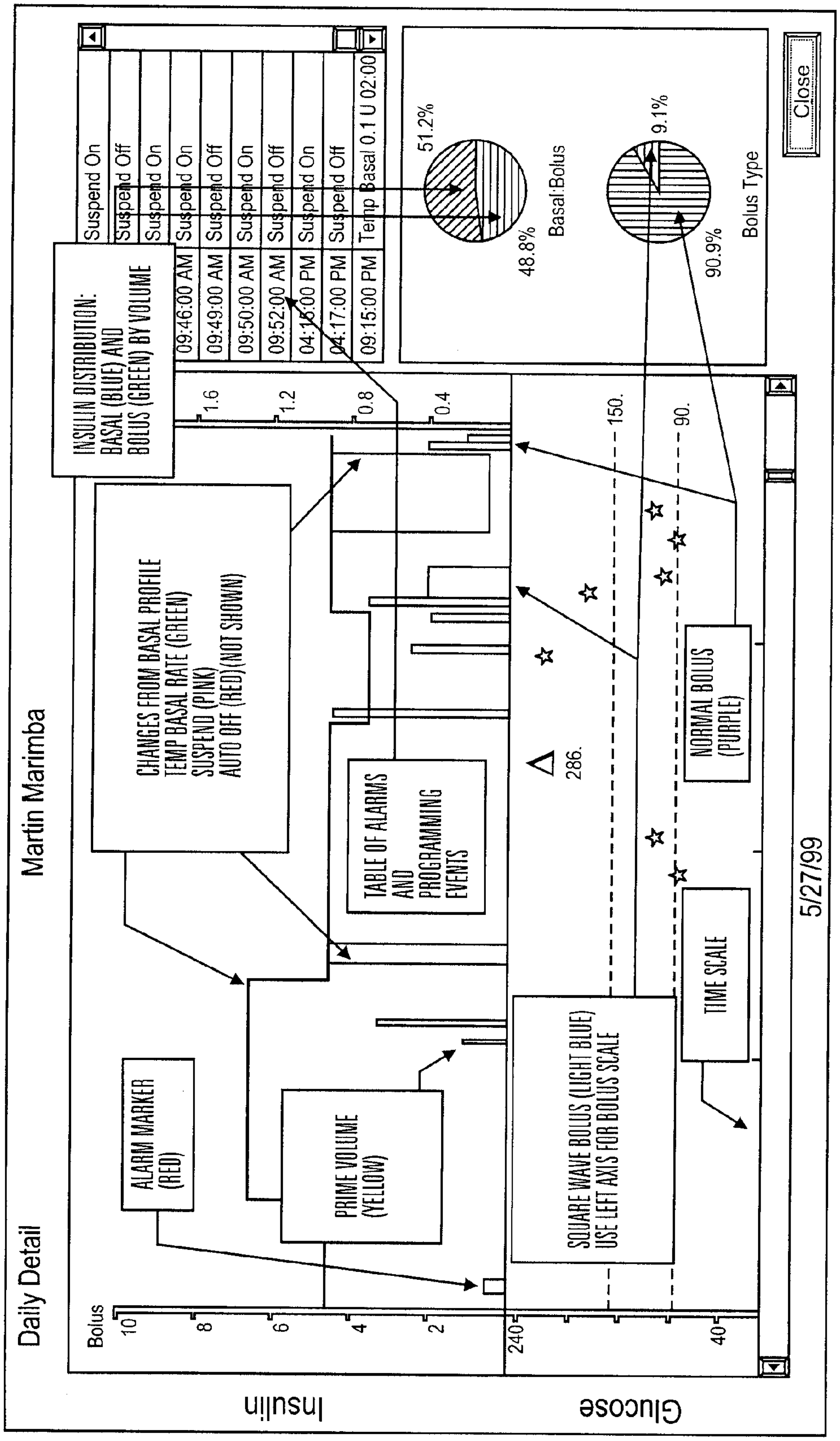
Figure 18C:
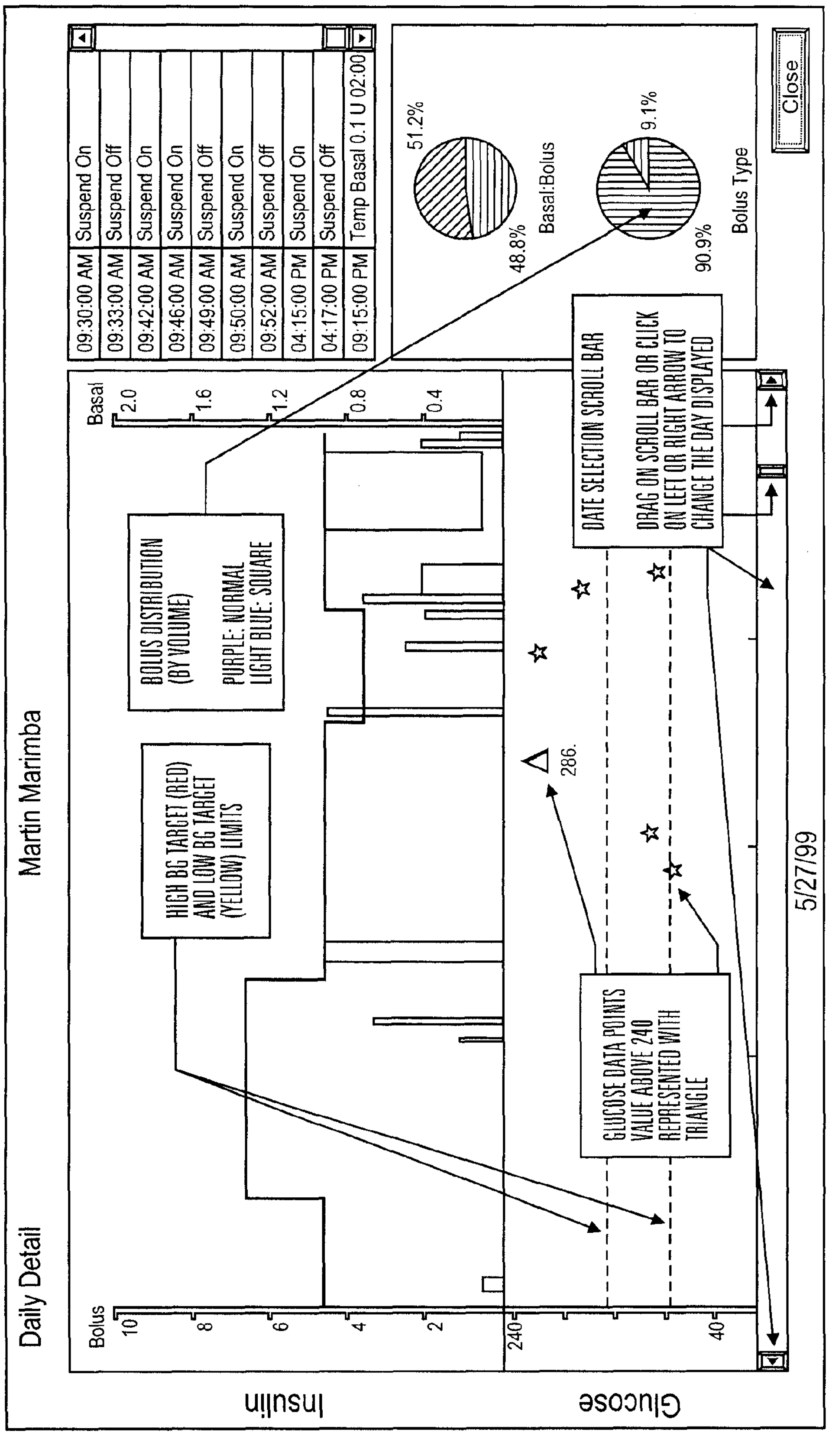
Figure 19A:
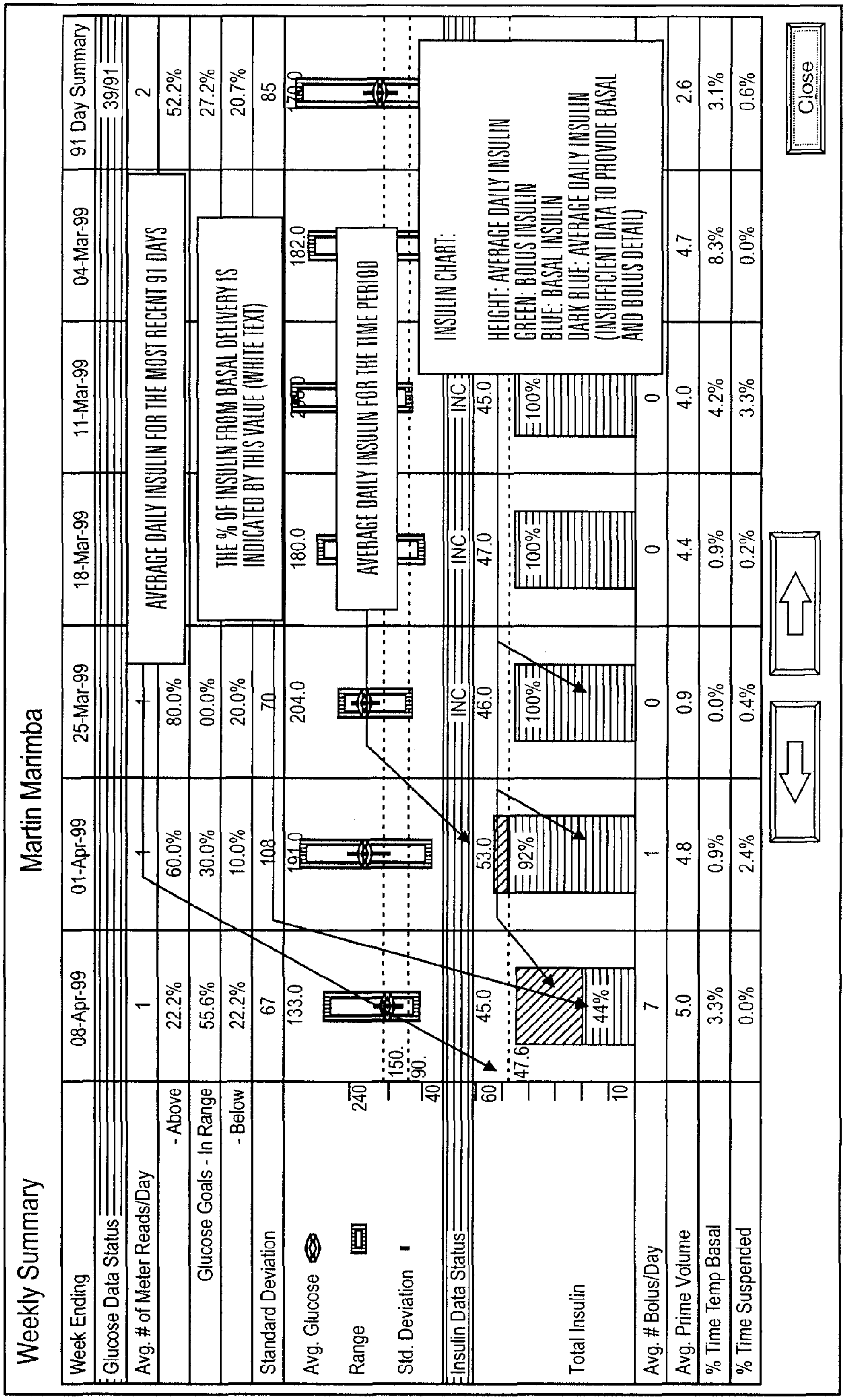
FIGS. 19(*a*)-(*d*) are views of a Weekly Summary display screen used by software in accordance with an embodiment of the present invention.
Figure 19B:
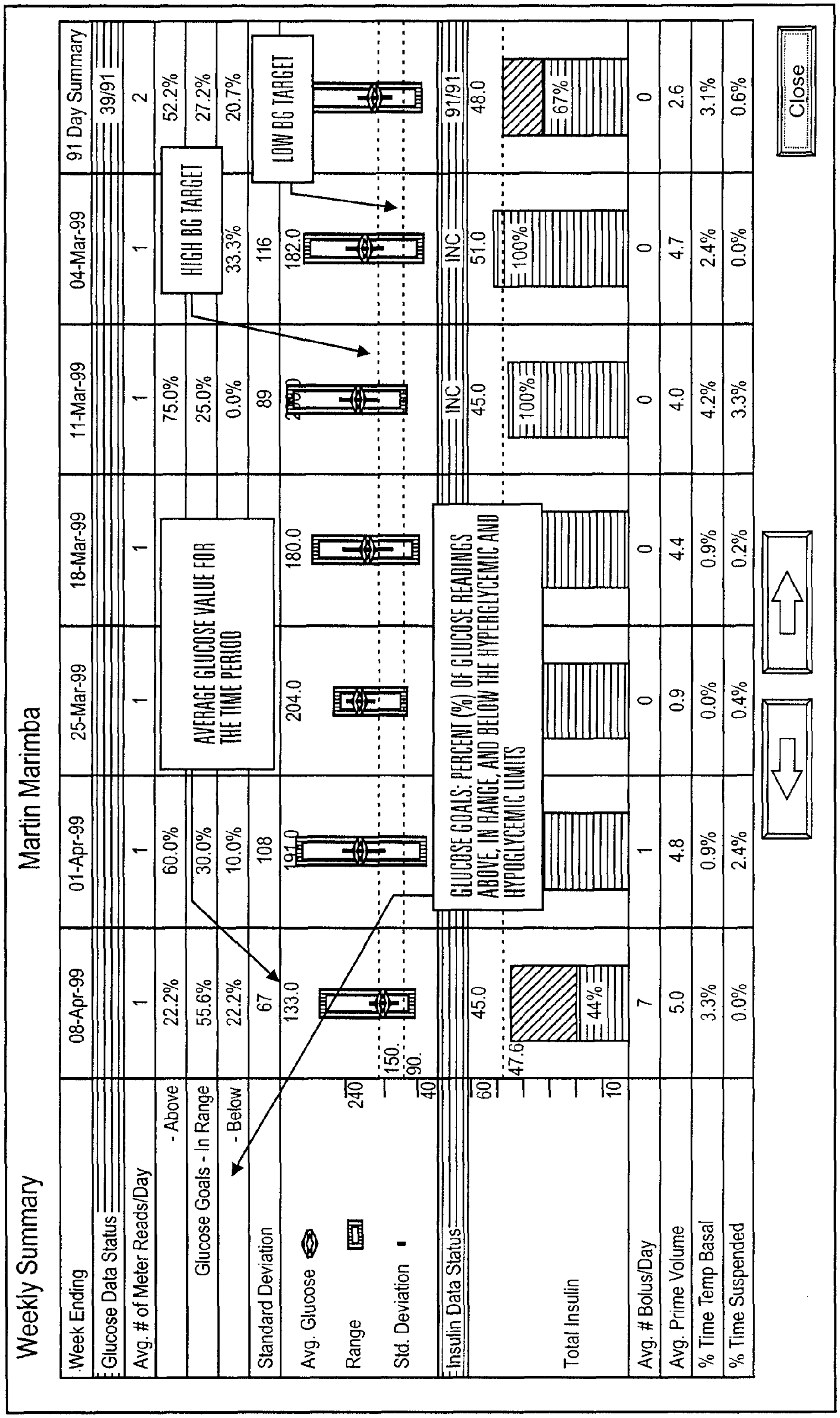
Figure 19C:
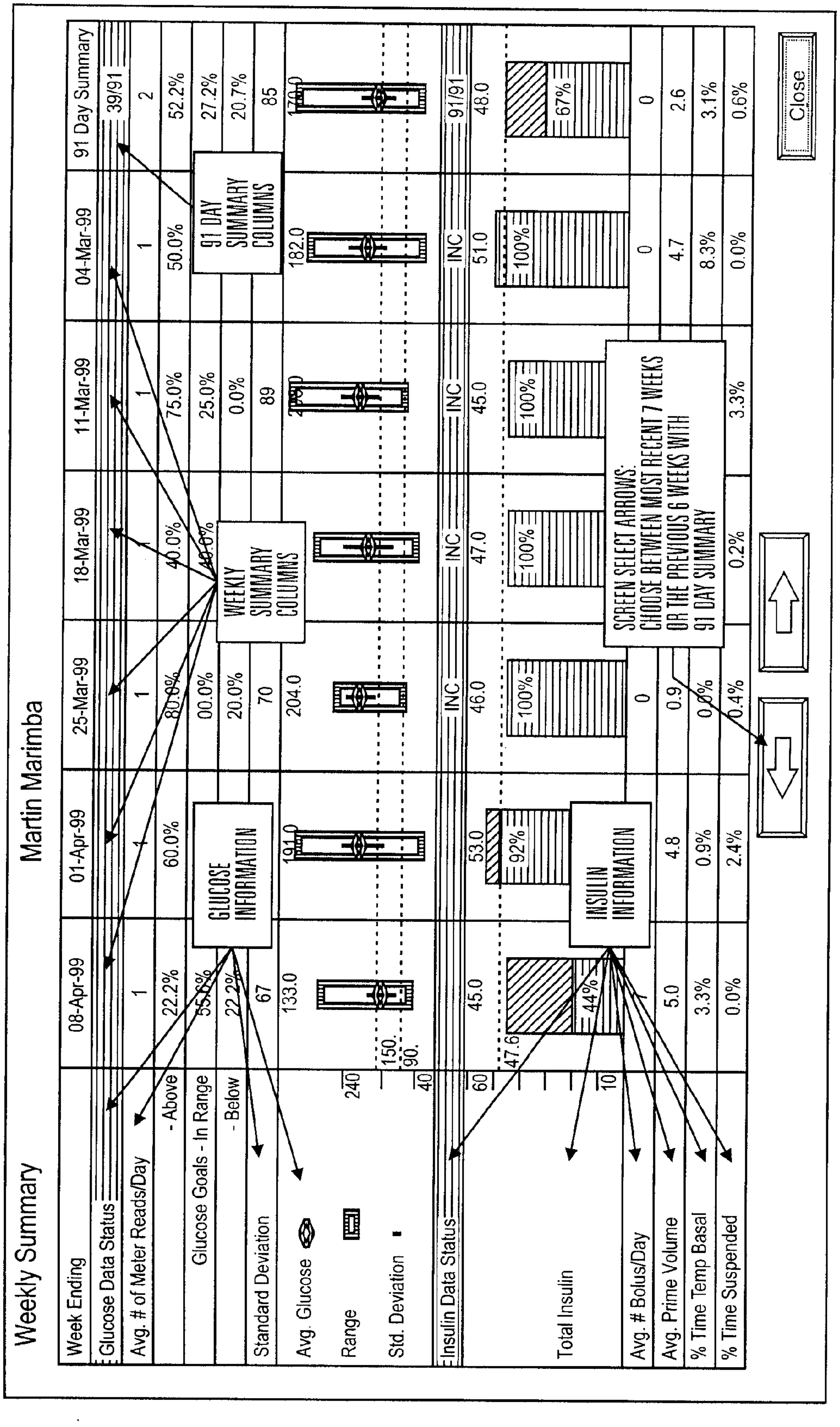
Figure 19D:
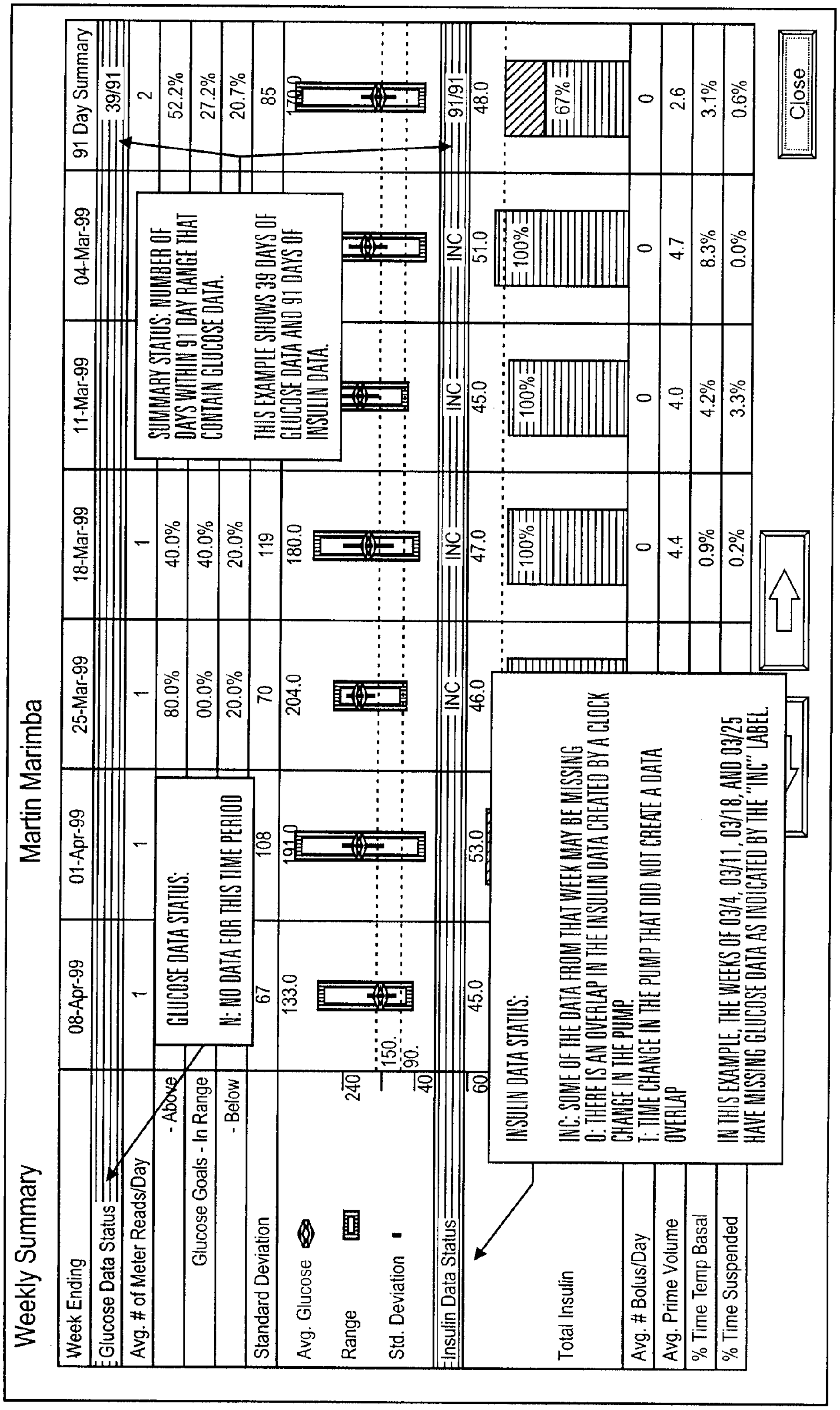

FIGS. 18(*a*)-(*c*) illustrate the Daily Details report screen, which is selectable by the icon shown in FIG. 11(*o*). This report provides a detailed daily view of each of up to 91 days of infusion pump, glucose meter, and sensor (e.g., monitor) data. Each screen represents a single day's data and consists of the following components: infusion pump data (i.e., insulin usage data), sensor and meter data (i.e., glucose data), alarm/event/marker table, and pie charts (basal:bolus ratio and bolus type).

The infusion pump data is shown in the upper section and graphically depicts basal rate, bolus, prime, and alarm history for the specified day. The basal rate is shown as a line indicating: normal basal rate, temporary basal rate, auto-off, and suspend (preferably, the programmed normal basal rate shall be shown as a dashed line during any of: suspend, temporary basal rate, or auto-off). Boluses will also be indicated. The alarm markers will be positioned to show the time of any alarm. In the illustrated report, two insulin scales are marked due to the relative scale of a bolus (large) compared to a basal rate (small). The bolus scale shall be on the left y-axis and the basal scale shall be on the right hand y-axis. In particular embodiments, any priming events will also be shown.

The sensor and meter data is shown in the lower section and graphically depicts meter readings and sensor data-vs.-time for the specified day. Preferably, any continuous glucose monitor (i.e., sensor) readings will be displayed as a continuous line graph. Meter readings will be marked as either a reference value or as calibration points. Any sensor event markers, such as small rectangular markers, or the like, at the bottom edge shall depict sensor event markers.

The alarm/event/marker table is shown in an upper side section and will be shown only if either infusion pump 12, glucose meter 24 or glucose monitor 18 (i.e., sensor) data is present. Alarms and events from the infusion pump 12, glucose meter 24 and glucose monitor 18 will be listed in order of time of the event/alarm. Textual definitions for events shall be listed if defined; otherwise a numeric value for the events shall be shown. This table shall display the following 'programming changes' for the current day: Time/Date change—displays new date (in mm-dd-yy format) and new time, where the time change is displayed in either 12 or 24 hr format depending on user's settings; Suspend On/Off—time the feature was turned on and was time turned off; Temporary basal rate—displays setting of a Temporary Basal Rate including amount in units per hour (e.g. 0.6 u/h) and duration displayed in same format as duration for bolus history; Basal Rate change—a note referring to a Basal Profile section for basal rate change history; battery removal/replacement—displays the removal and subsequent replacement of batteries with time of action; Maximum Basal Rate change—changes of the setting along with the time of action; Maximum Bolus change—displays the change of setting along with the time of action; Insulin Concentration change—displays the change of concentration; Auto Off Change—displays new feature setting along with the time of change displayed in hours; Alarm/Error Code—brief description of the alarm/error.

The pie chart data is shown in a lower side section and graphically depicts basal:bolus ratio and bolus type as pie charts.

FIGS. 19(*a*)-(*d*) illustrate the Weekly Summary report, which is selectable by the icon shown in FIG. 11(*p*). This report provides 13 weekly summaries of meter and pump data followed by a 91 day summary of the entire period. Each weekly column is composed of 2 vertical sections: Monitor and Meter Data (Glucose Data Status) and Infusion Pump Data (Insulin Data Status) using both tabular and graphical formats. As discussed above, this report is similar to the Daily Summary report shown in FIG. 16.

The Weekly Summary report is be split between two screens with 7 weeks on the first screen and 6 weeks on the second screen. In addition, a 91 day summary column will follow the 13th week on the second screen. Preferably, the report will arrange data and graphics into a table format with one row for each data category and one column for each week. The most recent week's data (i.e. 'column') shall be on the left with prior weeks to the right. In alternative embodiments, other data formats or orders of presentation may be used.

Each week's data (i.e. column) shall consist of:

1) tabular monitor and/or meter data including the average number of meter readings per day (numeric); glucose goals (numeric): percent that are above the hyperglycemic limit, percent that are in range, and percent that are below hypoglycemic limit (as set in the User Preferences screen); standard deviation of the week's meter readings (numeric); average glucose value (i.e. the average meter reading) (numeric); and a graphic component that shows the glucose reading range (e.g., a narrow vertical rectangle), average glucose value (e.g., a diamond within the rectangle), and the hyperglycemic and hypoglycemic limits (e.g., shown as 2 dotted horizontal lines). In alternative embodiments, other data formats or orders of presentation may be used.
2) Tabular infusion pump data including the average Daily total insulin (numeric); average number of boluses per day (numeric); average prime volume (numeric); the percent of the time that a Temporary Basal rate is used (numeric); the percent of the time that the infusion pump was in the Suspend mode (numeric); and a graphical component including total insulin, basal insulin, bolus insulin in a stacked column chart, with basal amount on the bottom including the percent of insulin delivered by basal rate (numeric), and the graphic also shows the average daily total insulin for the 13 week period as a horizontal dotted line with associated numeric value. In alternative embodiments, other data formats or orders of presentation may be used.

Figure 20A:
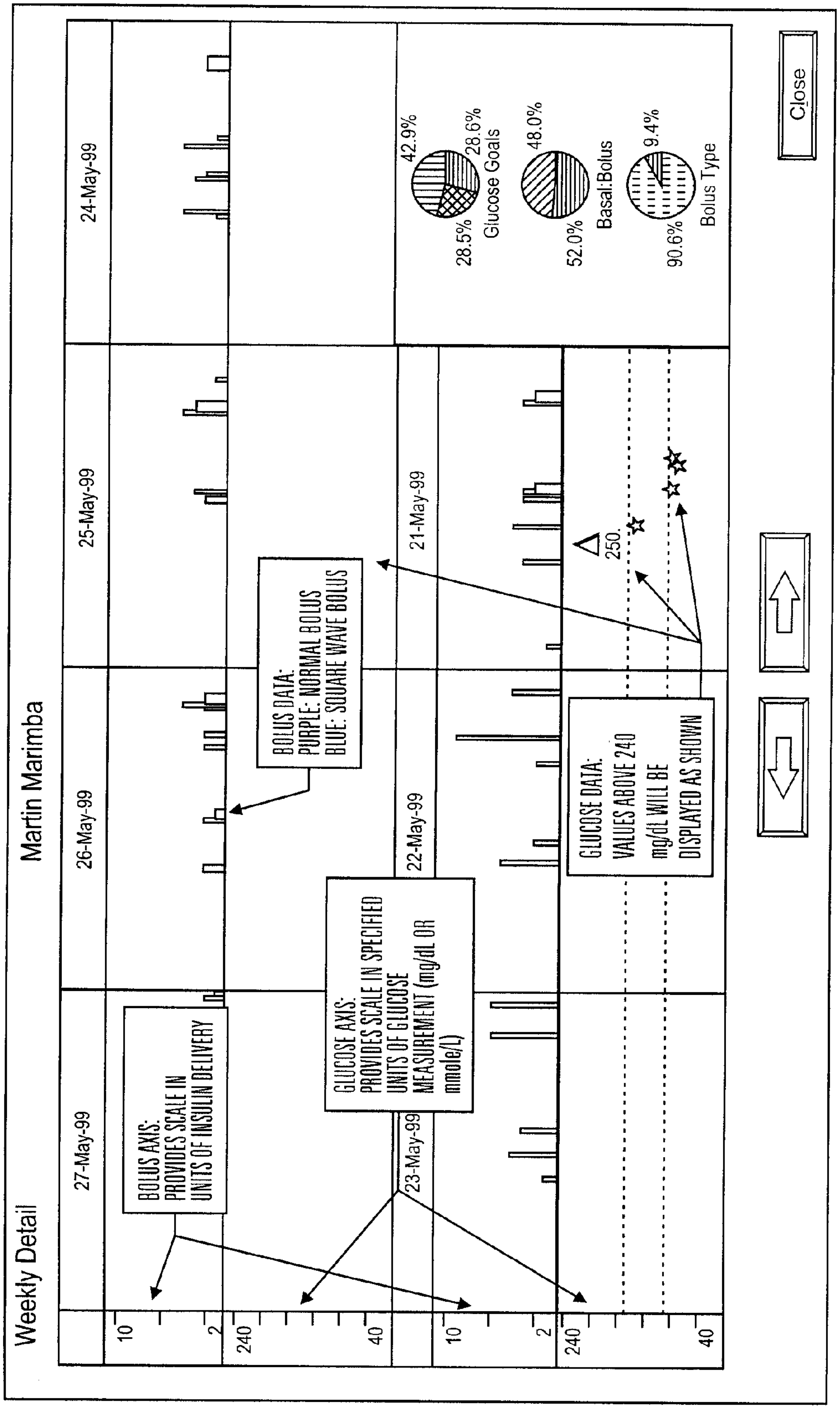
FIGS. 20(*a*)-(*b*) are views of a Weekly Detail display screen used by software in accordance with an embodiment of the present invention.
Figure 20B:
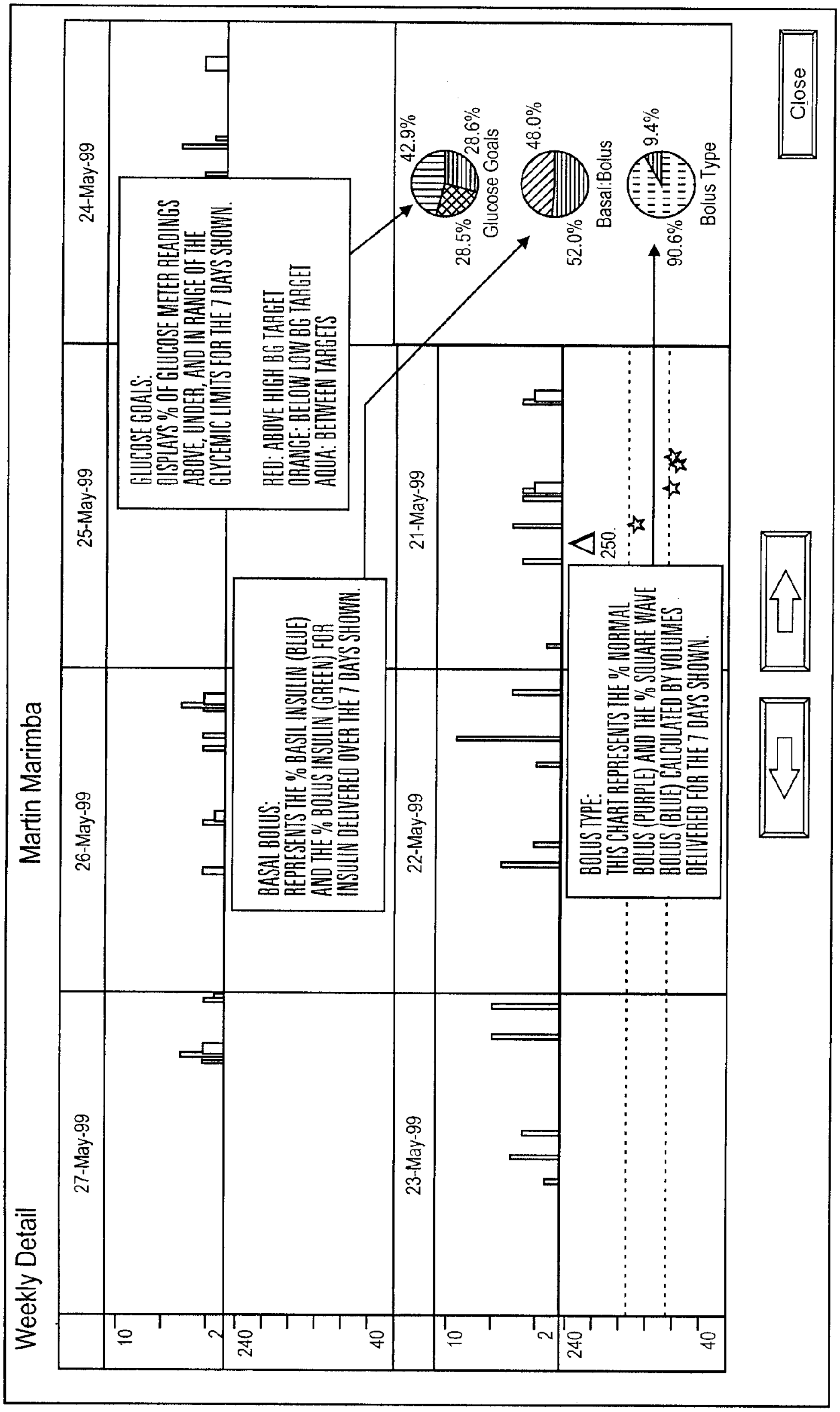

FIGS. 20(*a*)-(*b*) illustrate the Weekly Details report, which is selectable by the icon shown in FIG. 11(*q*). This report provides a 14 day graphical view of infusion pump data (bolus & primes) and glucose meter (but not sensor) readings. The screen is split evenly between 2 screens with 7 days on each screen, and each screen having a first row with 4 days and a second row with 3 days. Data and graphics are arranged in a table format with one row for each data category (e.g. infusion pump boluses and primes, or glucose meter data) and one column for each day. Additionally, pie charts of infusion pump and glucose meter data are displayed. In alternative embodiments, glucose monitor (sensor) data may be included, and/or a legend explaining the symbols used may be provided on the screen. Preferably, the most recent date (e.g., column) shall be on the left with prior dates to the right.

The infusion pump data includes the boluses and primes covering a 14 day period. Generally, the basal profile is not included since this is not changed frequently, but alternative embodiments could include it as part of the report. The data should include an insulin scale that is marked in units, and each bolus and prime should be indicated against this scale.

The glucose meter data is a plot of meter readings that covers the specified 14 day period. Preferably, the readings are plotted against a glucose scale of 20 to 240 (although other limits may be used). The hyperglycemic and hypoglycemic limits (set in the User Preferences screen) will be displayed as horizontal dotted lines. In particular embodiments, the numeric values of the limits shall be displayed adjacent to the lines. Any off the scale readings, such as those greater than 240 will be indicated at the upper edge of the Meter Data graph by a 'triangle' and a numeric value.

The pie charts will include 3 pie charts that each covers 7 days of infusion pump and glucose meter data. The Glucose Goals chart includes three sections that show the percentage of glucose meter readings that were above, within, and below range. The Basal/Bolus ratio chart includes two sections that shows the percentage of total basal insulin and total bolus insulin. The Bolus Type chart includes two sections that show the percentage of bolus volume that was delivered by a Normal Bolus and a Square Wave Bolus volume. In preferred embodiments, any dual boluses are split into the Normal Bolus and Square Wave Bolus components. However, in alternative embodiments, the dual boluses may be included as a separate section of the pie chart.

Figure 21A:
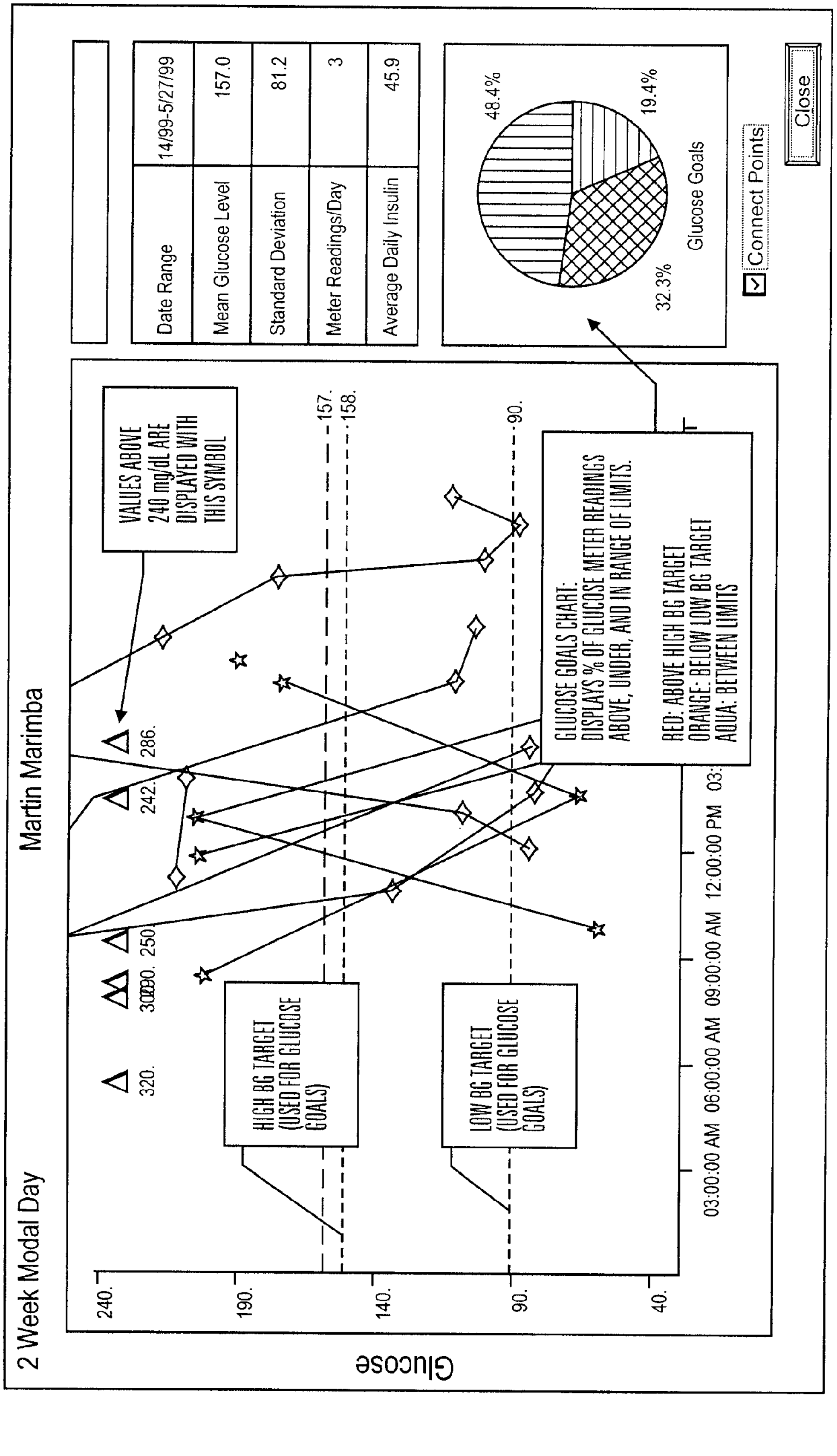
FIGS. 21(*a*)-(*b*) are views of a 2 Week Modal Day display screen used by software in accordance with an embodiment of the present invention.
Figure 21B:
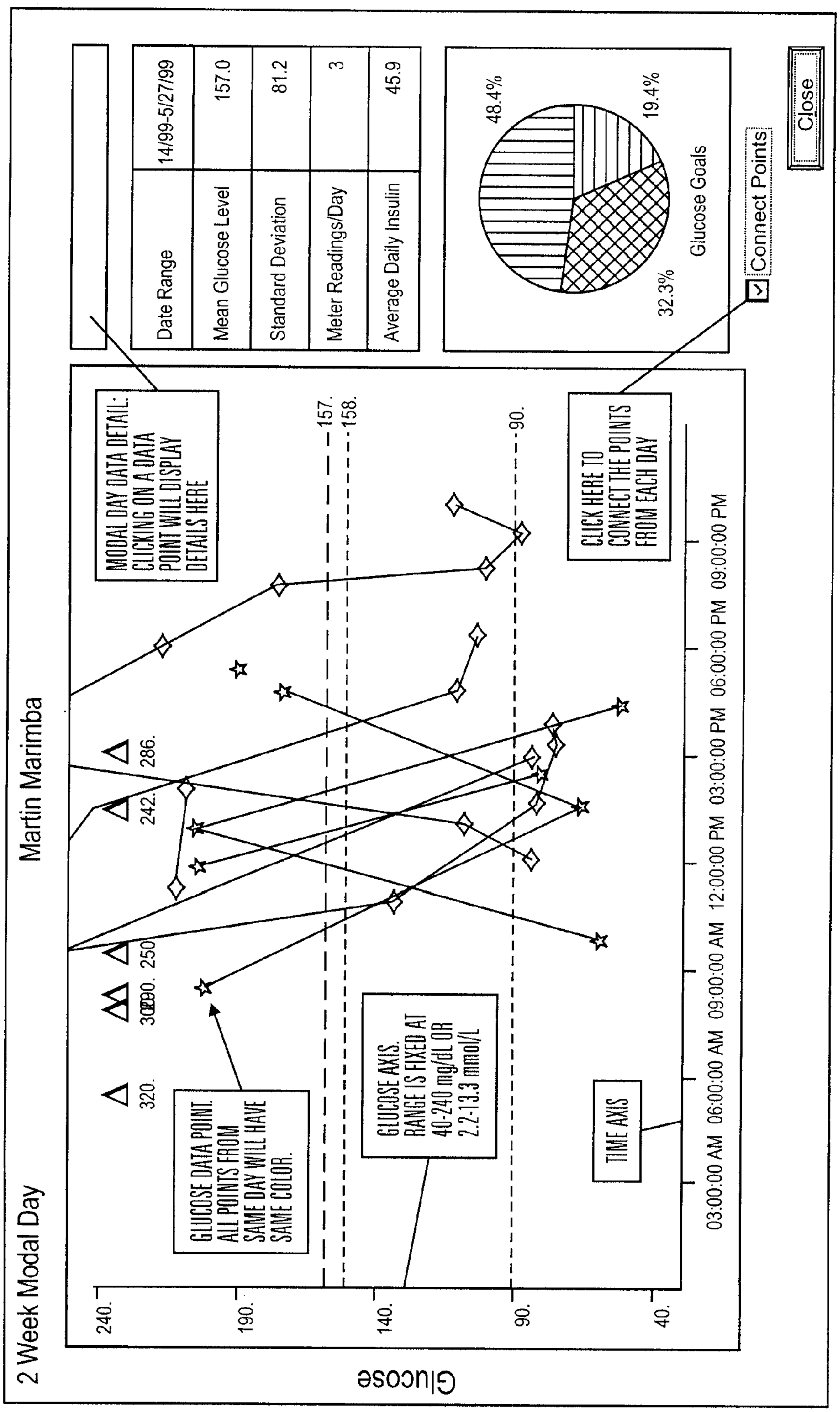

FIGS. 21(*a*)-(*b*) illustrate the 2 Week Modal Day report, which is selectable by the icon shown in FIG. 11(*r*), This report provides the glucose meter data from a specified 14 days so that it is plotted vs. time on a single day scale so that a user may visualize trends over 2 week period as it relates to specific times of day. The user also has the option of connecting all of the data from the same day using a connecting line. In addition, to aid in understanding the data, each day's data (i.e. multiple points) shall have a unique color, and any connecting lines (when present) shall also be color coded to match the colors of points. The hypoglycemic and hyperglycemic limits (set in the User Preferences screen) will be shown as horizontal dotted lines. Also, the 14 day mean value of meter readings shall be shown as a horizontal dotted line.

The 2 Week Modal Day report will also have a tabular Statistical Data section that will include the date range (e.g., the total span of dates displayed), number of days displayed, Mean Glucose Level for the selected period, Standard Deviation of the glucose meter readings, Average number of meter readings per day. The 2 Week Modal Day report will also include a Glucose Goals pie chart having three sections that show the percentage of glucose meter readings that were above, within, and below range for the selected period.

Figure 22A:
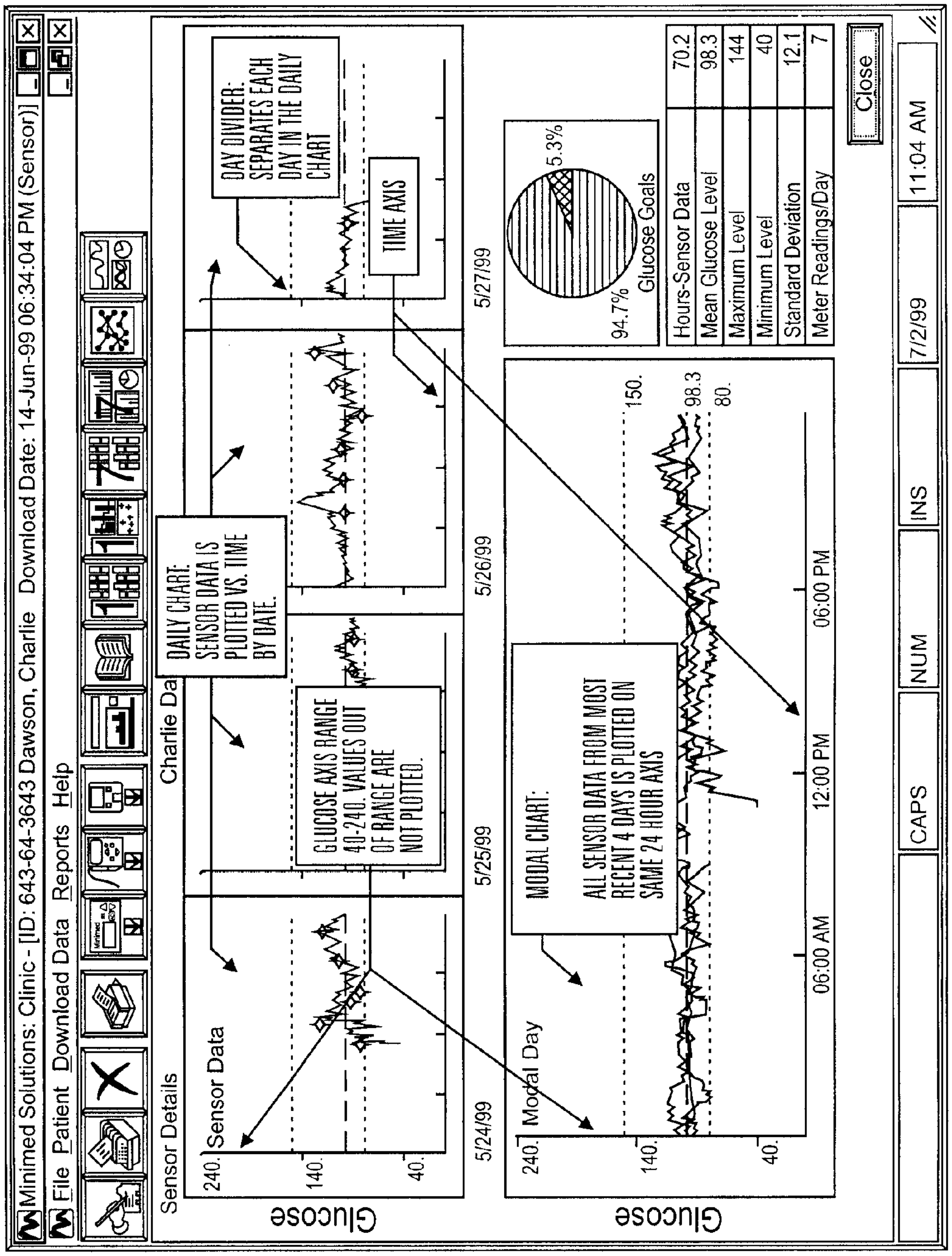
FIGS. 22(*a*)-(*b*) are views of a Sensor Details display screen used by software in accordance with an embodiment of the present invention.
Figure 22B:
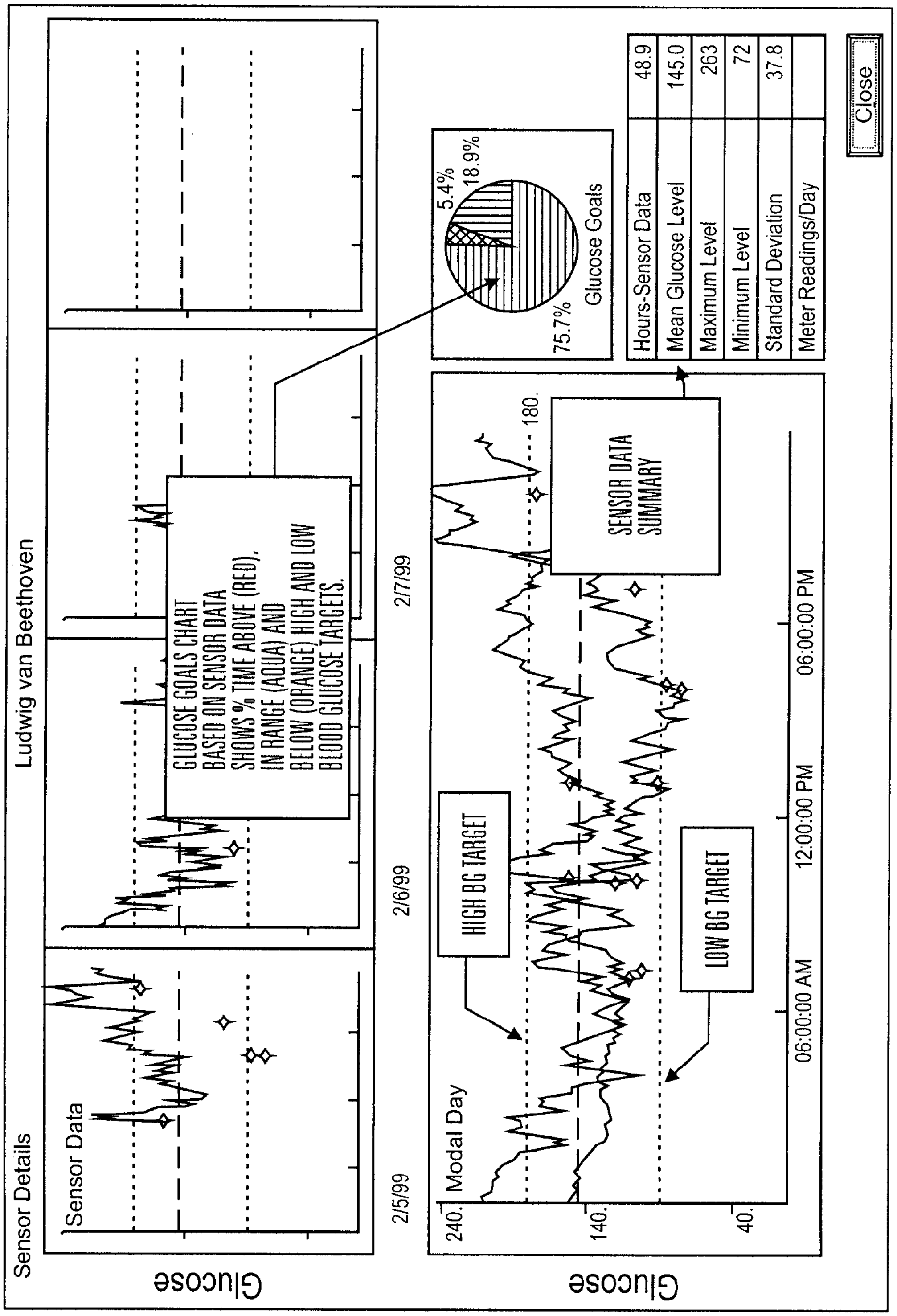

FIGS. 22(*a*)-(*b*) illustrate the Sensor Details report, which is selectable by the icon shown in FIG. 11(*s*). This report depicts Glucose Monitor data (including meter calibration & reference data) for the specified 4 day period. The report includes the following components: 1) Continuous Glucose Measurement data (preferably, displayed on a 4 day time scale.), Modal Day display of Glucose Monitor data displayed on a 24 hour scale. In preferred embodiments, the four days of data immediately prior to (and including) the specified download date will be displayed. However, in alternative embodiments, the user may specify other time periods. Preferably, calibration and reference data points will be integrated with the sensor data and will be differentiated by 'point style' (i.e. shape of the 'dot'). Also, each day's sensor data will be uniquely colored, and a specific day's color in the 'Sensor Data' section will match the corresponding day color in the 'Modal Day' graph section. In addition, the hypoglycemic and hyperglycemic glucose limits (set in the User Preferences screen) will be indicated as dashed lines.

The top portion of the report includes the Sensor Data section that displays a 4 day continuous graph of Glucose Monitor data integrated with meter calibration and reference points. The bottom portion of the report includes the Modal Day section that displays the Sensor data for the specified 4 day period so that it is plotted vs. time on a single day scale (i.e., 4 continuous line graphs of sensor data shall be overlaid on a single day time scale). The bottom side portion includes a Glucose Goals pie chart that has three sections that show the percentage of glucose meter readings that were above, within, and below range for the selected 4 day period. The bottom side portion also has a tabular statistical data section that will include the Hours of Sensor data displayed, the Mean Glucose Level for the selected period, the Maximum and Minimum Glucose level for the selected period, the Standard Deviation of the glucose Sensor data, and the average number of meter readings per day.

As shown in FIGS. 23(*a*)-(*f*) various legends, symbols and color codes may be utilized on the reports. In particular embodiments, the symbols and color codes may be displayed on the report as a legend to define the graphical elements used on the report screen. They are also provided here to further define and clarify the material shown in the reports described herein.

As described above, the reports are generated and displayed by the communication station PC software used by the PC 14 to interpret the data downloaded from a medical device through the communication station 10 to the PC 14. However, the displayed reports may also be printed out for hard copy records or analysis, such as by the use of a menu or by selecting the icon shown in FIG. 11(*h*). Preferably, either a single report or multiple reports may be printed. In some embodiments, the reports may be faxed or E-mailed to a different location for review by a patient, physician, insurance company, or the like. In preferred embodiments, when the 'Quick Reports' operation is initiated under the menu shown in FIG. 11(*c*), the reports previously specified in the User Preferences screen will be printed.

FIGS. 24-29 illustrate alternative report screens that can be accessed using other embodiments of the communication station PC software. Many of the reports provide information that is similar to that provided above, but it is presented in different style or format to illustrate some of the possible variations that are available in the report screens. The embodiment includes a Main Screen (not shown) that allows selection of the various reports. This embodiment includes the following reports: Summary—displays infusion pump summary data; Current Settings—displays the current infusion pump settings and basal profile; Daily Log—displays a daily log book of patient data; Event Log I—displays the bolus history, daily totals, and prime history logs; Event Log II—displays the programming events, alarm and basal rate change history logs; and Event Log III—displays the complete infusion pump history log. The Main Screen also includes a Print Screens button that prints the selected reports.

For these embodiments, each report will have three button options on the bottom of each screen: Main Screen—a single click on this button will return the user to the main screen to select another report; Print Screen—a single click on this button will print the current report; and Help—a single click on this button will pull up the help files.

Figure 24:
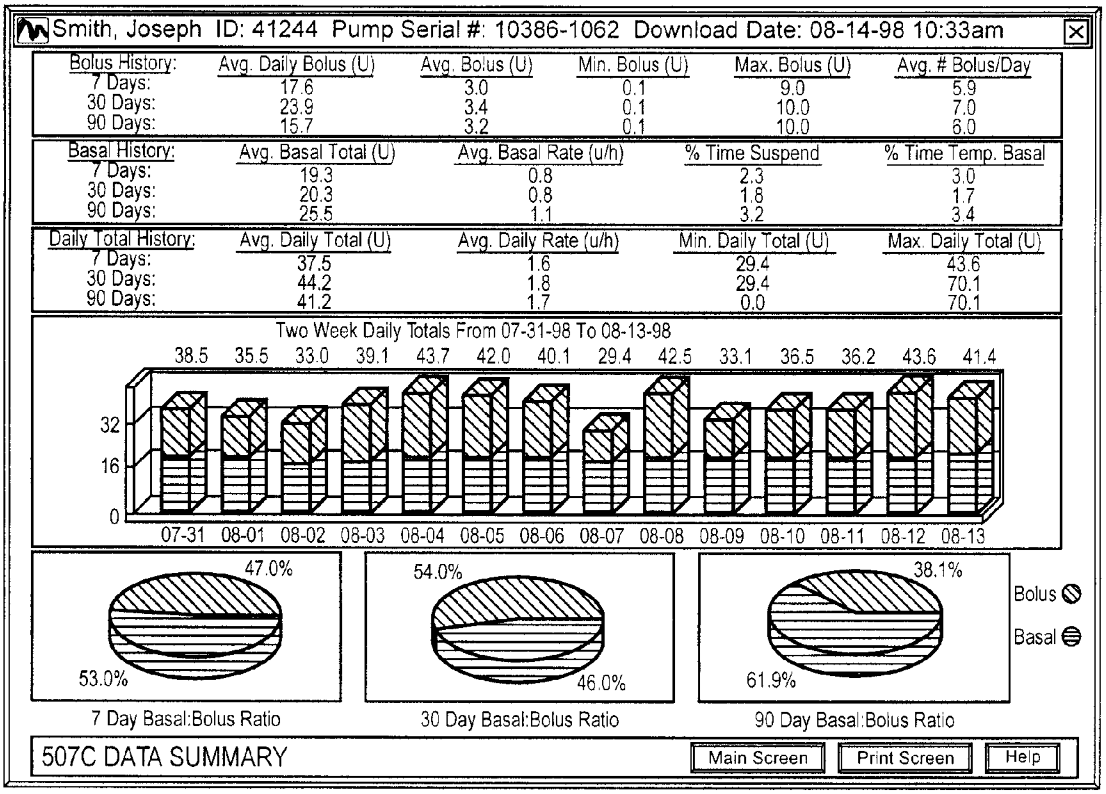
FIG. 24 is a view of a Data Summary display screen used by software in accordance with an embodiment of the present invention.

FIG. 24 illustrates the Data Summary report which has 5 main sections: the Bolus History section displays the average bolus, the minimum bolus, the maximum bolus and the average number of boluses given per day for three different time buckets (e.g., 7 days, 30 days and 90 days). The Basal Rate History section displays the average basal total (i.e., the total amount delivered over a 24 hour period), the average basal rate (i.e., the average basal rate delivered per hour), the percent of the time the infusion pump was suspended and the percent of the time spent in a temporary basal rate for the same three time buckets listed under the Bolus History. The Daily Total History section displays the average daily total of insulin delivered, the average daily rate for insulin delivered, the minimum daily total for insulin delivered, and the maximum daily total of insulin delivered for the three different time buckets listed under the Bolus History. The Daily Total Graph section is a bar graph which shows the total amount of insulin delivered over the past 14 days. The bars are "stacked" to show the amount of insulin delivered by basal rate delivery (e.g., bottom of bar) and the amount of insulin delivered by bolus delivery (top of bar). Underneath each bar the date is displayed, and the insulin scale is to the left of the graph in units (preferably, these values scale automatically to match the amount that the user has delivered). The Basal/Bolus Ratio Graphs are made up of three pie charts which show the percent ratio of Bolus delivery vs. Basal Rate delivery for three time periods. Graph one shows this ratio for the last seven (7) days, graph two for thirty (30) days, and graph three for ninety (90) days. The ratio appears in text adjacent to each of the sub-sets in the graph. When looking at reports that display averages for time buckets, if there is not enough data to complete a time bucket, for example if only 35 days worth of data is stored in the infusion pump, or the downloaded data, no data will be displayed for 90 days bucket. Alternative embodiments will allow the selection of different time periods to be analyzed.

Figure 25:
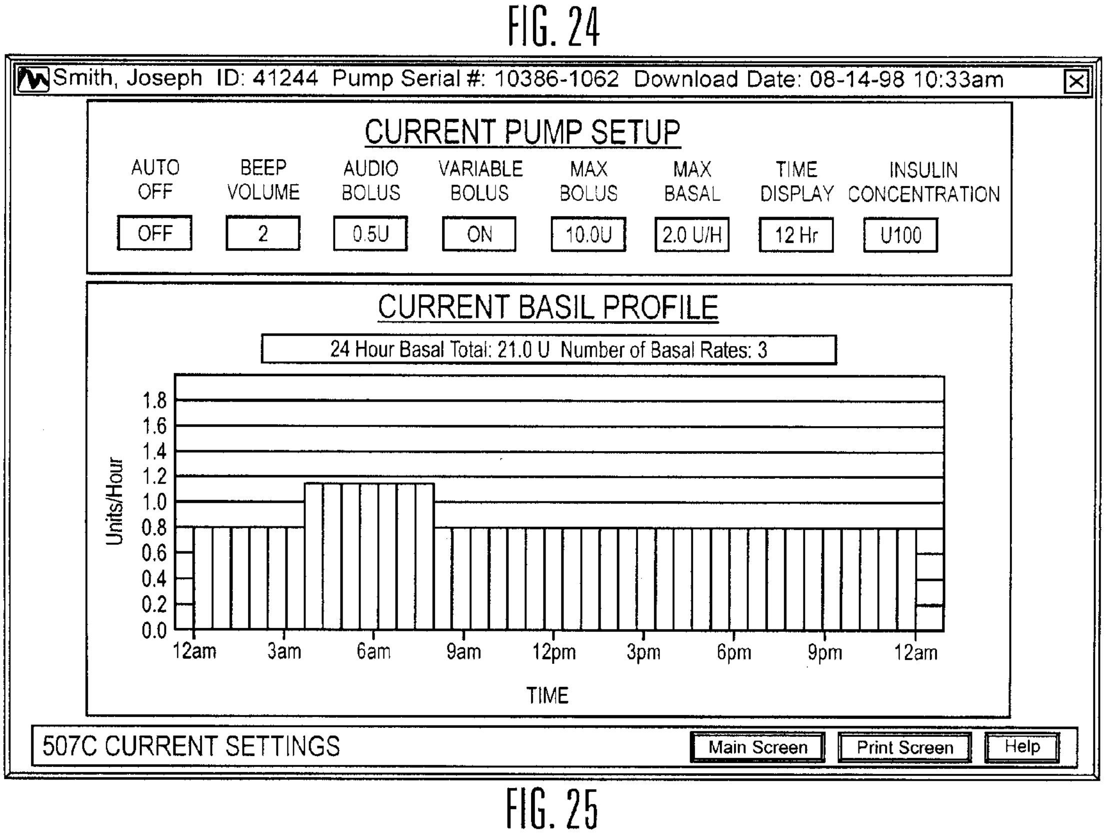
FIG. 25 is a view of a Current Settings display screen used by software in accordance with an embodiment of the present invention.

FIG. 25 illustrates the Current Setting report which has two main components: a listing of the current infusion pump settings and a graph of the current basal profile. The current infusion pump settings includes information on: Auto Off (OFF or the hour setting if on, e.g. 10 hr); Beep Volume (setting level 1, 2 or 3); Audio Bolus (OFF or increment step level either 0.5 or 1.0 units); Variable Bolus (OFF/ON); Maximum Bolus (0-25 unit setting in units); Maximum Basal rate (0-35 unit setting in units/hour); Time Display (12 or 24 hr); and Insulin Concentration (U100, U50, U40). The current basal profile graph is a continuous bar graph over a 24 hour period. Insulin amounts are shown to the left of the graph in units/hour (preferably, these values automatically scale to adjust to the individual's basal rate and the highest value is equal to the next highest whole unit above the user's highest basal rate setting). The time in hours is depicted across the bottom of the graph 12 am, 3 am, 6 am, 9 am, 12 noon, 3 pm, 6 pm, 9 pm and 12 am markers indicated (if the infusion pump is set in 24 hour format, the graph will show 24 hour markers). Faint horizontal lines are present across the graph at 0.2 unit increments up to a maximum of 5.0 units/hour. If the total exceeds 5.0 units the scale switches to 0.5 unit increments. The graph's header contains the title "Current Basal Profile" as well as the 24 hour basal total and the number of basal rates currently being used.

FIG. 27 illustrates the Daily Log Book report that allows the user to review the infusion pump's operation by date. The report displays the following information: Bolus History, Basal Profile, Programming Events, Alarms, Primes and the Daily Total for insulin.

Bolus History is table that displays the time, type, amount, and duration of the day's bolus deliveries in chronological order. The boluses are listed as N for Normal, S for Square, D/N for the Normal portion of a Dual Wave Bolus, and D/S for the Square Wave portion of a Dual Wave Bolus. Bolus amounts are recorded in units, e.g. 6.0 units. Duration times for Square and Dual Wave boluses are displayed using the following format: a one hour bolus would be shown as 1:00, a 2 and a ½ hour bolus is shown as 2:30.

Basal Profile is a table that displays the current basal rates set in the pump and the times which each rate starts for the current day.

Programming Events is a table that displays all the programming changes for the current day beginning at 12:00 am. The possible programming changes include: Time/Date Change—displays new date (in mm-dd-yy format) and new time and time of change (a Time change is displayed in both 12 and 24 hour format depending on the User Preferences). Suspend ON/OFF—displays the time when Suspend feature was first turned on and then turned off. Temporary basal rate—displays a setting of a temporary basal rate including amount in units per hour, e.g. 0.6 u/h, as well as time, and duration of the temporary basal rate. Basal rate change—displays a note referring to Log II to review basal rate changes. Battery removal/replacement—displays the removal and replacement of batteries with the time of action. Maximum basal rate change—displays the change of setting with the time of action. Maximum bolus change—displays the change of setting with the time of action. Insulin Concentration change—displays the change of concentration with the time of action. Auto Off Change—displays setting along with the time of change displayed in hours.

Alarms is a table that displays the time, alarm/error code and a brief description of any alarm received for the current 24 hour period. The following alarms are the most common alarms that the user may see: A-04—No Delivery; A-05—Depleted Batteries; A-06—Auto Off; A-35—Motion Sensor; and A-51—Watchdog. Alternative embodiments may display more or less alarms.

Prime History is a table that displays the time and prime amount in units for the current day. Daily Total is an area that displays the current day's total insulin delivered as a Basal and Bolus in units, e.g. 60.0 units as of the time of the download. To select a different date to review, the user clicks the "Select Date" softkey button and clicks on the desired date.

FIG. 26 illustrates the Event Log I report that includes three scrollable tables: Bolus History table that shows the date, time, type, amount and duration of all the boluses stored in the infusion pump (The average daily total for the boluses shall be displayed under the Bolus History table); Daily Total History table that displays the date and the total amount of insulin delivered as basal rate plus boluses for up to 90 days (the average daily total of insulin shall be displayed under the Daily Total table); and Prime History table that displays the date, amount and time for up to 50 primes.

FIG. 28 illustrates the Event Log II report, which includes three tables: the Programming Event history, the Alarm History, and the Basal Rate Change history. Programming Event History—displays the date, time and type of up to 200 programming events. Alarm History—displays the date, time and type up to 50 alarms and error codes. Basal Rate Change History—displays a listing of basal rate changes that have occurred including the complete basal profile with date, time and setting changes. If no basal changes have occurred, no data is displayed.

FIG. 29 illustrates the Event Log III report, which lists all of the infusion pump operations in reverse chronological order for the past 90 days. The last listing for each day is a daily insulin total.

Various modifications may be made to these reports, and they may be combined together in different ways to create custom reports that are suited to the user's needs. Although various color and graphical schemes have been presented, other schemes are possible without departing from the scope of the embodiments of the present invention. The reports have emphasized the use of a communication station 10 with an infusion pump 12 and augmenting the data with data from a glucose meter 24 and/or glucose monitor 18. However, the communication station 10 and PC software may be used with other medical devices, which then place particular emphasis on data from these devices. For instance, the communication station 10 may be used primarily with a glucose monitor 18 and provide expanded reports beyond those described above. The reports may report additional histories and events similar to those described above for the infusion pump 12 or in a manner that are particularly suited to the analysis requirements of the glucose monitor 18 and its data.

Figure 6:
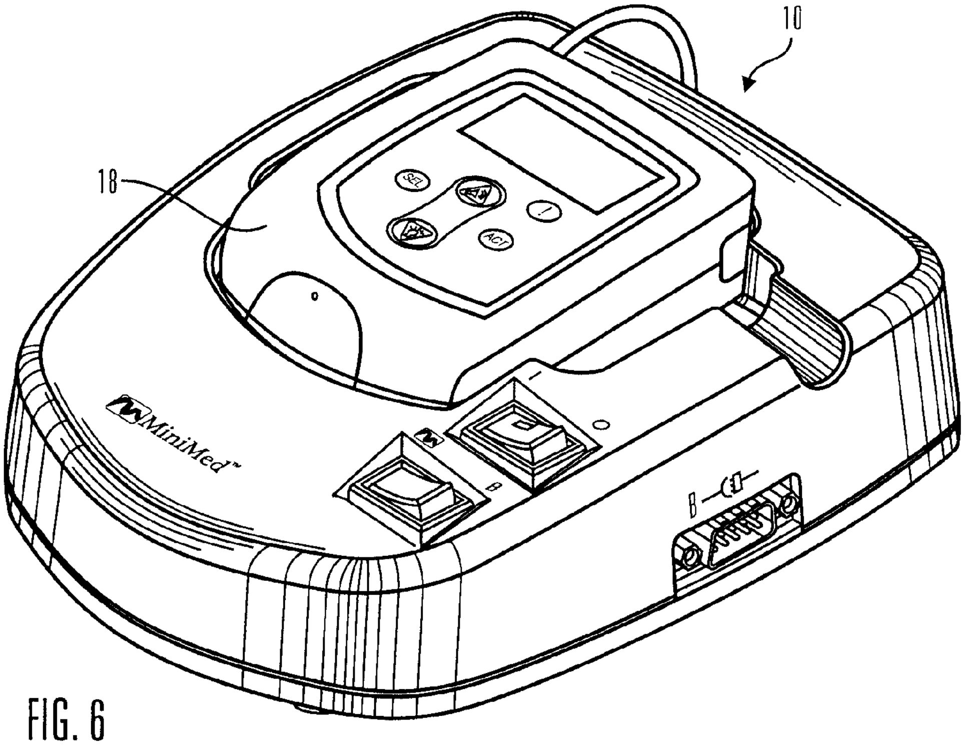
FIG. 6 is a perspective view of a glucose monitor mounted in the cradle of the communication station shown in FIG. 1.

In that view, as illustrated in FIG. 6, a communication station 10 may used with a glucose monitor 18 to transfer data and information to and from a personal computer (PC) 14. In preferred embodiments, the communication station 10 is connected to the PC 14 through a wired connection 16. However, in alternative embodiments, the PC 14 may be connected by a wireless connection, a computer network, by modem, or the like. In addition, the PC 14 may be a laptop computer, another medical device with processing capabilities, or the like. In preferred embodiments, the glucose monitor 18 is connected to the communication station 10 through a cradle holder 20 on the communication station 10 that maintains the position and orientation of the glucose monitor 18. This permits the glucose monitor 18 to interface with the communication station 10 using an optical communication connection having optical elements 22. In alternative embodiments, the glucose monitor 18 may be connected using other methods, such as wired connections, radio connection, contact connections, or the like.

The glucose monitor system 1001, in accordance with a preferred embodiments of the present invention include a sensor set 1010, and a glucose monitor 18. The sensor set 1010 utilizes an electrode-type sensor 1012, as described in more detail below. However, in alternative embodiments, the sensor may use other types of sensors, such as chemical based, optical based or the like. In further alternative embodiments, the sensors may be of a type that is used on the external surface of the skin or placed below the skin layer of the user. Preferred embodiments of a surface mounted glucose sensor would utilize interstitial fluid harvested from the skin. Preferably, the sensor 1012 monitors blood glucose levels, and may be used in conjunction with automated or semi-automated medication infusion pumps of the external or implantable type as described in U.S. Pat. Nos. 4,562,751; 4,678,408; 4,685,903 or 4,573,994, to deliver insulin to a diabetic patient. However, other embodiments may monitor other analytes to determine viral load, HIV activity, bacterial levels, cholesterol levels, medication levels, or the like.

The glucose monitor 18 generally includes the capability to record and store data as it is received from the glucose sensor 1010, and then includes either a data port or wireless transmitter for downloading the data to a PC 14, a data processor 200, laptop, communication station, or the like for later analysis and review. The PC 14, data processor 200, laptop, or the like, utilizes the recorded data from the glucose monitor to determine the blood glucose history. The purpose of the glucose monitor system 1001 is to provide for better data recording and testing for various patient conditions utilizing continuous or near continuous data recording.

Logged data can be analyzed further for detailed data analysis. In further embodiments, the glucose monitor system 1001 may be used in a hospital environment or the like. Still further embodiments of the present invention may include one or more buttons 1122, 1124, 1126 and 1128 on the glucose monitor 18 to program the monitor 18, to record data and events for later analysis, correlation, or the like. In addition, the glucose monitor may include an on/off button 1130 for compliance with safety standards and regulations to temporarily suspend transmissions or recording. The glucose monitor 18 may also be combined with other medical devices to combine other patient data through a common data network and telemetry system. In alternative embodiments, the glucose monitor 18 may be designed as a Holter-type system that includes a Holter-type recorder that interfaces with a glucose monitor, processor, computer of the like, such as disclosed in U.S. patent application Ser. No. 09/246,661 filed Feb. 5, 1999 and entitled "An Analyte Sensor and Holter-Type Monitor System and Method of Using the Same", which is herein incorporated by reference. Further embodiments may use wireless communication between the sensor set 1010 and the glucose monitor 18 utilizing a telemetered glucose monitor transmitter as shown and described in U.S. patent application Ser. No. 09/377,472, filed Aug. 19, 1999 and entitled "Telemetered Characteristic Monitor System and Method of Making the same", which is herein incorporated by reference.

Figure 30:
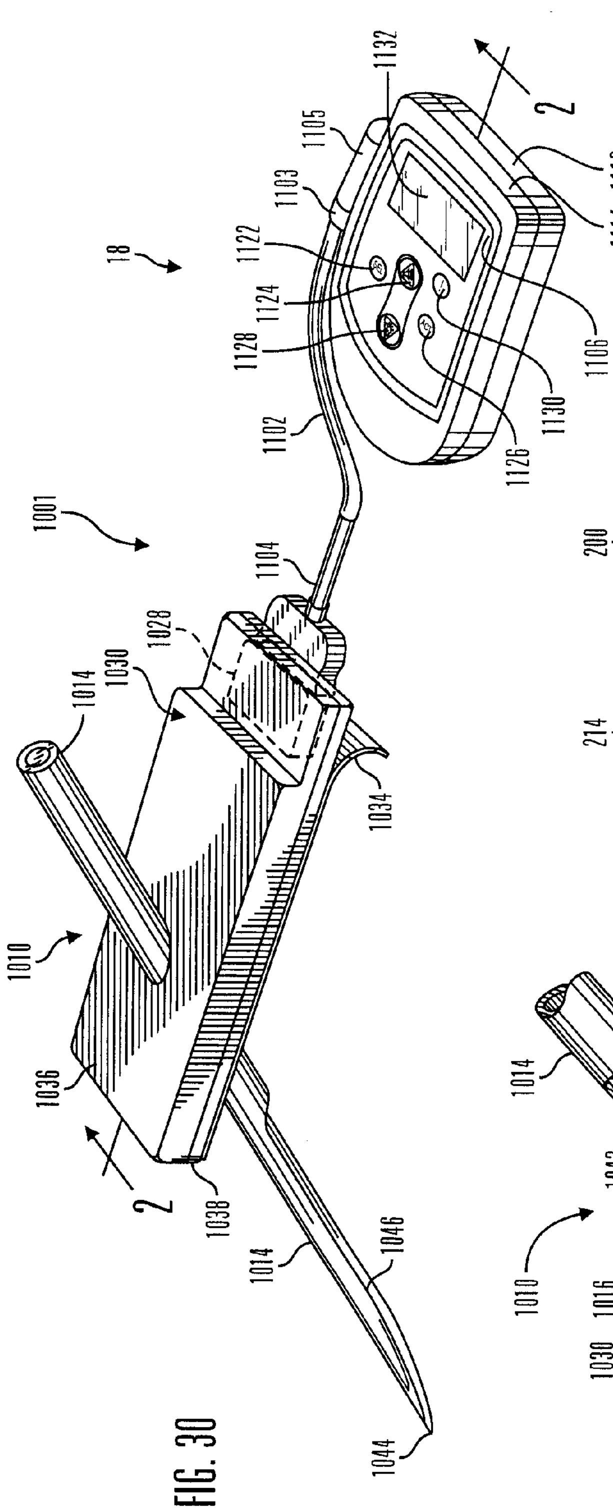
FIG. 30 is a is a perspective view illustrating a subcutaneous glucose sensor insertion set and glucose monitor device embodying the novel features of the invention.
Figure 31:
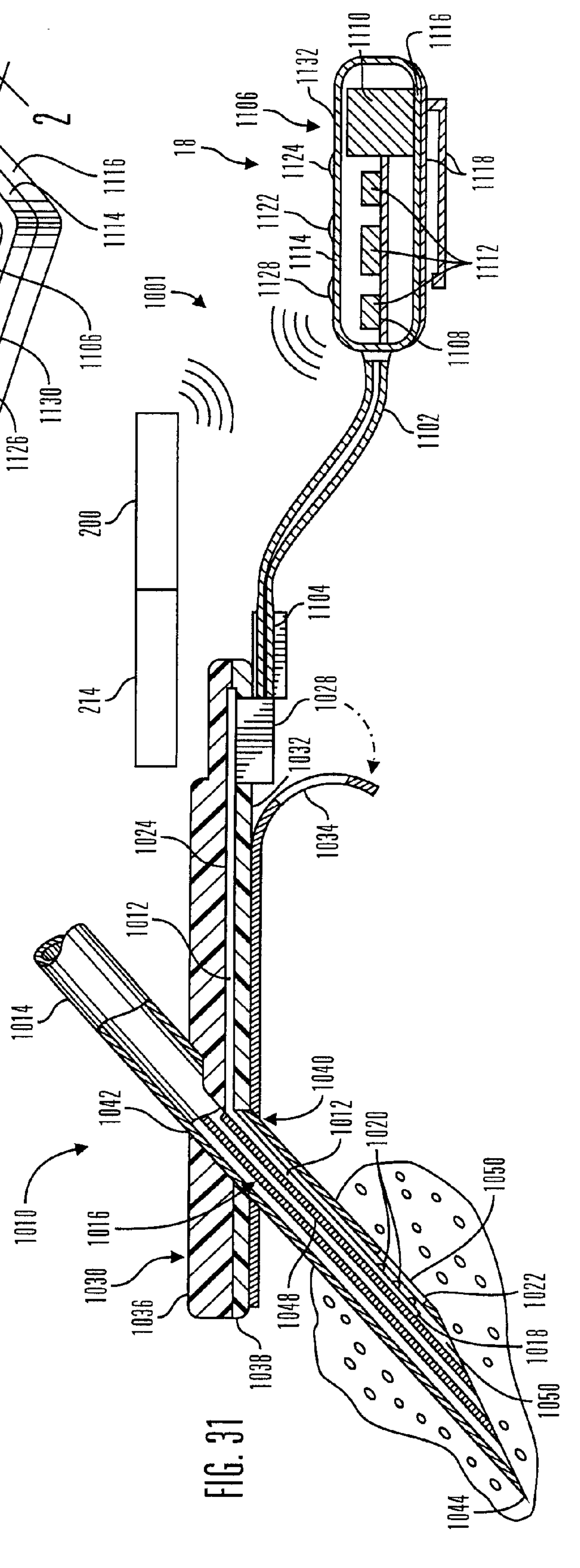
FIG. 31 is an enlarged longitudinal vertical section taken generally on the line 2-2 of FIG. 30.

As shown in FIGS. 30 and 31, a sensor set 1010 is provided for placement of a flexible sensor 1012 (see FIG. 31), or the like, at a selected site in the body of a user. The sensor set 1010 includes a hollow, slotted insertion needle 1014, and a cannula 1016. The needle 1014 is used to facilitate placement of the cannula 1016 at the insertion site. The cannula 1016 includes a sensing portion 1018 of the sensor 1012 to expose one or more sensor electrodes 1020 to the user's bodily fluids through a window 1022 formed in the cannula 1016. After insertion, the insertion needle 1014 is withdrawn to leave the cannula 1016 with the sensing portion 1018 and the sensor electrodes 1020 in place at the selected insertion site.

Further description of flexible thin film sensors of this general type are be found in U.S. Pat. No. 5,391,250, entitled METHOD OF FABRICATING THIN FILM SENSORS, which is herein incorporated by reference. The connection portion 1024 may be conveniently connected electrically to the sensor monitor (not shown), a glucose monitor 18, or a data processor 200, computer, communication station, or the like, by a connector block 1028 (or the like) as shown and described in U.S. Pat. No. 5,482,473, entitled FLEX CIRCUIT CONNECTOR, which is also herein incorporated by reference.

The sensor 1012 is mounted in a mounting base 1030 adapted for placement onto the skin of a user. As shown, the mounting base 1030 is a generally rectangular pad having an underside surface coated with a suitable pressure sensitive adhesive layer 1032, with a peel-off paper strip 1034 normally provided to cover and protect the adhesive layer 1032, until the sensor set 1010 is ready for use. As shown in FIG. 32, the mounting base 1030 includes upper and lower layers 1036 and 1038, with the connection portion 1024 of the flexible sensor 1012 being sandwiched between the layers 1036 and 1038. The connection portion 1024 has a forward section joined to the sensing portion 1018 of the sensor 1012, which is folded angularly to extend downwardly through a bore 1040 formed in the lower base layer 1038.

The insertion needle 1014 is adapted for slide-fit reception through a needle port 1042 formed in the upper base layer 1036 and further through the lower bore 1040 in the lower base layer 1038. As shown, the insertion needle 1014 has a sharpened tip 1044 and an open slot 1046 which extends longitudinally from the tip 1044 at the underside of the needle 1014 to a position at least within the bore 1040 in the lower base layer 1036. Above the mounting base 1030, the insertion needle 1014 may have a full round cross-sectional shape, and may be closed off at a rear end of the needle 1014. Further description of the needle 1014 and the sensor set 1010 are found in U.S. Pat. No. 5,586,553, entitled "TRANSCUTANEOUS SENSOR INSERTION SET" and co-pending U.S. patent application Ser. No. 09/346,835, entitled "DISPOSABLE SENSOR INSERTION ASSEMBLY," which are herein incorporated by reference.

The cannula 1016 is best shown in FIGS. 30 and 31, and includes a first portion 1048 having partly-circular cross-section to fit within the insertion needle 1014 that extends downwardly from the mounting base 1030. In alternative embodiments, the first portion 1048 may be formed with a solid core; rather than a hollow core. In preferred embodiments, the cannula 1016 is constructed from a suitable medical grade plastic or elastomer, such as polytetrafluoroethylene, silicone, or the like. The cannula 1016 also defines an open lumen 1050 in a second portion 1052 for receiving, protecting and guideably supporting the sensing portion 1018 of the sensor 1012.

As shown in FIGS. 30 and 31, the glucose monitor 18 is coupled to a sensor set 1010 by a cable 1102 through a connector 1104 that is electrically coupled to the connector block 1028 of the connector portion 1024 of the sensor set 1010. In preferred embodiments, the plug connector 1103 of the cable 1102 is connected to the glucose monitor 18 through a plug receptacle 1105. In alternative embodiments, the cable 1102 may be omitted, and the glucose monitor 100 may include an appropriate connector (not shown) for direct connection to the connector portion 1024 of the subcutaneous glucose sensor set 1010 or the subcutaneous glucose sensor set 1010 may be modified to have the connector portion 1024 positioned at a different location, such as for example, the top of the subcutaneous sensor set 1010 to facilitate placement of the glucose monitor 18 over the sensor set 1010.

The glucose monitor 18 includes a housing 1106 that supports a printed circuit board 1108, batteries 1110, memory storage 1112, the cable 1102 with the plug connector 1103, and the plug receptacle 1105. In preferred embodiments, the housing 1106 is formed from an upper case 1114 and a lower case 1116 that are sealed with an ultrasonic weld to form a waterproof (or resistant) seal to permit cleaning by immersion (or swabbing) with water, cleaners, alcohol or the like. As shown, the lower case 1116 may have an underside surface that includes a belt clip 1118 (or the like) to attach to a user's clothing.

As shown in FIG. 31, the PC 14, data processor 200, computer, communication station 10, or the like, may include a display 214 that is used to display the results of the measurement received from the sensor 1018 in the glucose sensor set 1010 received via a download from the glucose monitor 18. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 214 may also be used with buttons (not shown) on the PC 14, data processor 200, laptop, communication station 10, or the like, to program or update data in the data processor 200 or PC 14. In preferred embodiments, the glucose monitor 18 includes a display 1132 to assist the user in programming the glucose monitor 18, entering data, stabilizing, calibrating, downloading data, or the like.

After a sensor set 1010 has been used for a period of time, it is replaced. The user will disconnect the glucose sensor set 1010 from the cable 1102 and glucose monitor 18. In preferred embodiments, if an additional test is required and/or desired, the glucose monitor 18 is connected to a new sensor set 1010. A new sensor set 1010 and sensor 1012 are attached to the glucose monitor 18 and connected to the user's body. Recording then continues, as with the previous sensor 1012. Finally, the data stored in the memory 1112 of the glucose monitor 18 is downloaded (or transmitted) to the PC 14, data processor 200, laptop, communication station 10, or the like, for analysis and review.

Figure 33:
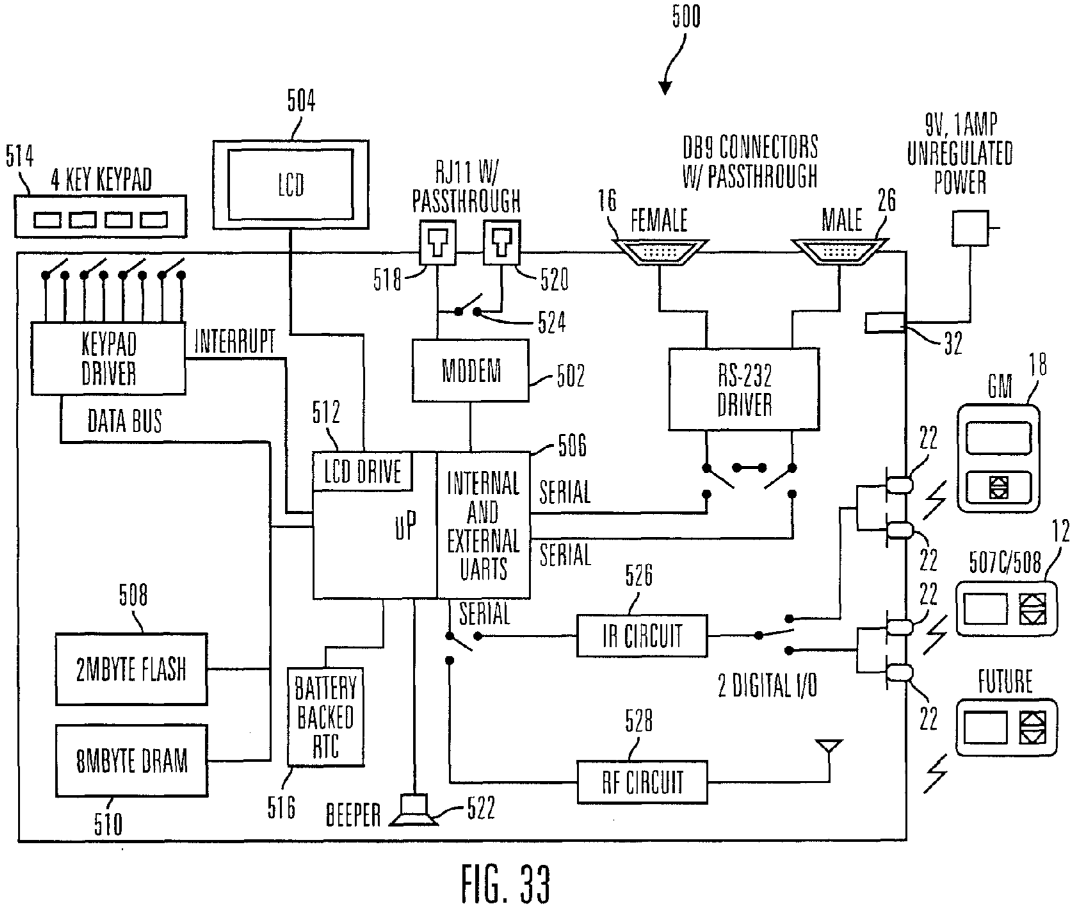
FIG. 33 is a simplified circuit schematic of a communication station in accordance with yet another embodiment of the present invention.

FIG. 32 shows a simplified block diagram of the communication station 10 shown in FIGS. 1-3 and described above. However, FIG. 33 shows a simplified circuit schematic of another embodiment of a communication station 500 that can be used with the medical devices described above. The communication station 500 shown FIG. 33 includes several improvements that increase the utility and capabilities of the communication station 500 to store and transmit data for later analysis by the software in the PC 14. The communication station 500, like the communication station 10 above, will communicate with infusion pumps 12, glucose monitors 18, and blood glucose meters 24 that have the capability of communicating over an RS-232 serial port 26. In addition to interfaces for the devices mentioned above, the communication station 500, like the communication station 10 above, will also incorporate a RS-232 serial port 16 for communication with a PC 14 or other local device. However, the communication station 500 will also include a modem 502 and a telephone interface for communication with a network-based information management service, such as is described in U.S. Patent Application Ser. No. 60/143,981 filed May 20, 1999 and entitled "Diabetes Integrated Management System", which is herein incorporated by reference. Reports similar to those described above may be generated by the network based information management service. Alternative embodiments may utilize other telecommunication architectures to connect with the network based information management service, such as DSL, Ethernet, LAN networks, TCIP, Tolken ring, Novel, IR, RF, and other wireless links, or the like.

The communication station PC software will have the capabilities listed below: an ability to store and process complete data sets from several devices in preparation for uploading the data to an application program or network service; an ability to display simple text instructions on an LCD display 504; an ability to enter data such as meter type, phone number, or the like, with the amount of data entry required to be minimized; an ability to update code in the field; an ability to store unique device serial number. In addition, the communication station 500 will have hardware support for RF communications with the infusion pump 12, glucose monitors 18, glucose meters 24, or the like, that support RF communications for program instructions and/or data transmission. Additional features may be incorporated into future releases of the software for the communication station following the product manufacturer date, and thus the communication stations in the field will have the capability to be updated to newer releases of software using the in-field code update capability of the software.

As shown in FIG. 33, the communication station will include the following hardware components: a DragonBall 68EZ328 CPU 506 running at 16 MHz; 2 MByte flash memory 508 that is writeable at least 50,000 times and 8 MByte DRAM 510 or 4 MB of RAM; an interface 512 to a Seiko G241D01R000 graphics LCD 504; four momentary switches for interface to an elastomeric keypad 514; a Real Time Clock 516, that is battery backed-up for 5 years; two RJ11 phone line connectors 518 and 520 with a passthrough relay; a modem 502; one female and one male DB9 RS232 ports 16 and 26, with the capability of multiplexing RX and TX to provide passthrough between the ports; a serial connection with signal multiplexing that allows redirection of the serial port to either the IR Circuit or the RF Circuit; an unregulated 9VDC, 1 Amp power input 32, with out the need of a power switch; a piezo beeper 522 capable of generating multiple tones.

As discussed, the communication station 500 includes a processor board that has two RJ11 phone line connectors 518 and 520. A passthrough relay 524 will allow the second RJ11 connector 520 to be disconnected from the first during modem communications. A status bit will be provided to indicate whether the line is in use. The processor board of the communication station 500 will also be compatible with the Conexant socket modem technology and will be useable with 14.4 Kbps, 33.6 Kbps, and 33.6 Kbps world class modems. In alternative embodiments, the RJ11 connectors 518 and 520 may be formed separate from the processor board, or replaced by a different connector format. In further alternative embodiments, the communication station may use higher or lower modem speeds and modems compatible with other communication standards, such as DSL, TCIP, ISDN, or the like. The processor board of the communication station will provide two RS232 ports 16 and 26 with one male and one female DB9 connectors. Signal multiplexing will provide a passthrough which connects the two serial ports to each other. The RS-232 Transceiver shall be ±15 kV ESD-Protected. EMI filtering of the RX and TX signals shall be provided. Only RX, TX, and GND signals need to be provided to the processor, however all standard RS232 signals shall be routed when the two ports 16 and 26 are connected in passthrough mode. In alternative embodiments, different connector specifications or formats may be used.

The processor board will have IR circuitry 526 for communication with the infusion pumps 12, and glucose monitors 18 having IR data transfer circuitry compatible with the circuitry of the communication station. The processor board will also have RF circuitry 528 for communication with the infusion pumps, glucose monitors and future devices that have RF data transfer or programming capabilities. The communication station 500 is also designed to communicate with several glucose meters such as the Medisense Precision QID, and will support for example the following Precision QID commands: Read Sensor and Erase Sensor. The One Touch glucose meter will be supported for the following commands: DM?—Send the Meter's software version and date; DM@—Send the Meter's serial number; DMF—Send date and time from the Meter's clock; DMI—dump the data log from the Meter's memory; and DMP—dump blood, control, and check strip records from the Meter's memory. In alternative embodiments, other meters and other commands may be supported.

The processor board shall be have a beeper 522 which can generate tones when driven by the Pulse Width Modulation capability of the Dragonball EZ processor 506. In alternative embodiments, other audio producing mechanisms, such as a speaker, sound card, or the like, may be used. The processor board is responsible for regulating the 9VDC, 1 Amp unregulated power that is provided. The power connector 32 will be a Kycon Part number KLD-0202-B. The input circuitry will provide Transient Surge protection, EMI filtering, and a Resettable Fuse.

The communication station 500 includes a improved user interface 512 to make the communication station 500 more versatile. The communication station 500 uses a Seiko Instruments G241D01R000 graphics LCD 504 that has 240×160 pixels. Assuming a minimal 8×6 pixel font, this display is capable of displaying up to 30×26 characters if oriented vertically or 20×40 characters if oriented horizontally. Preferably, the LCD 504 has a LED backlight. In alternative embodiments, other display devices, such as CRT, plasma, or the like may be used, different LCD types and sizes may be used, and the LCD may omit a backlight.

Figure 34:
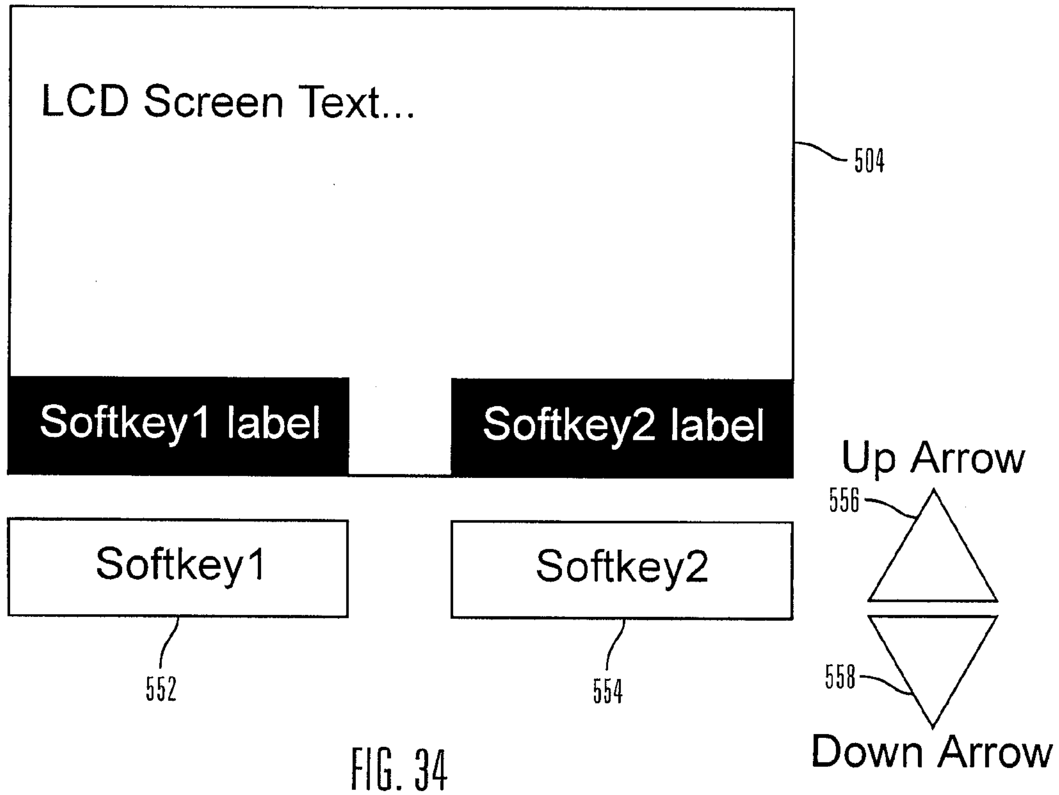
FIG. 34 is a generic view of an LCD for use with the embodiment of the communication station shown in FIG. 33.

The user interacts with the communication station 500 through the use of two soft keys 552 and 554 and two arrow keys 556 and 558 used with the display on the LCD 504. Feedback is received via the LCD and beeper. The user interface allows the user to navigate a variety of screens including: Menu Screens; Numeric Entry Screens; Softkey Screens; and Check Screens. An example of a typical LCD window is shown in FIG. 34.

Figure 35:
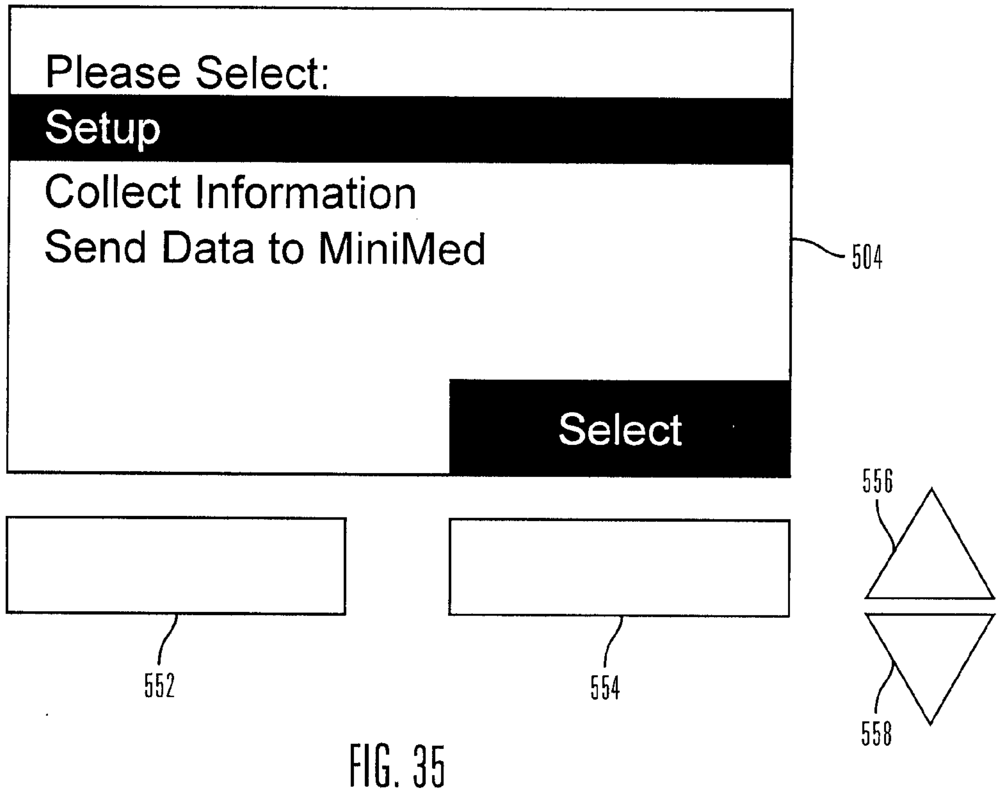
FIG. 35 is a menu screen view of an LCD for use with the embodiment of the communication station shown in FIG. 33.

FIG. 35 illustrates the main screen, which allows the user to move an inverted bar over each selection in a list using the arrow keys 556 and 558. When the desired item is highlighted the user presses the softkey 554 corresponding to the select option and that item is selected. After selection, the selected option or software function is executed.

Figure 36:
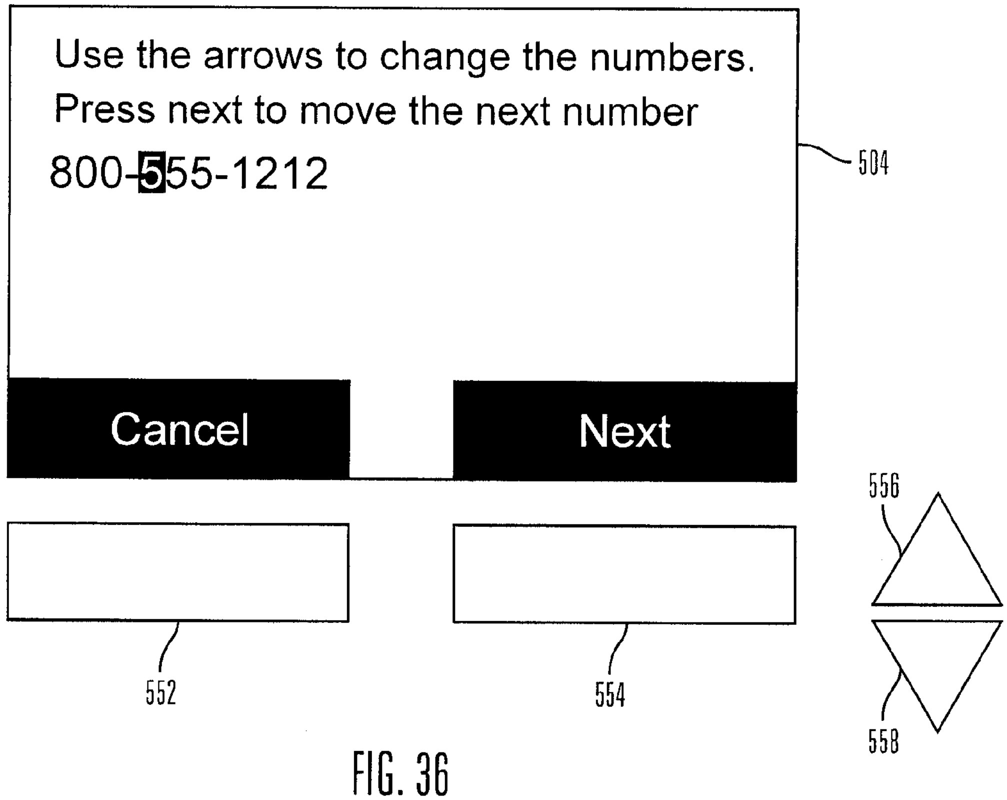
FIG. 36 is a alphanumeric screen view of an LCD for use with the embodiment of the communication station shown in FIG. 33.

FIG. 36 illustrates the alpha-numeric entry window, which allows the user to scroll through a list of alphanumeric options using the arrow keys 556 and 558. Once the desired entry is found the user accepts that entry by pressing the softkey 554 corresponding to the Next operation. The other softkey 552 can be used to either allow the user to back up a character or cancel entirely out of the screen. Once the user enters the last number, the screen is complete.

Figure 37:
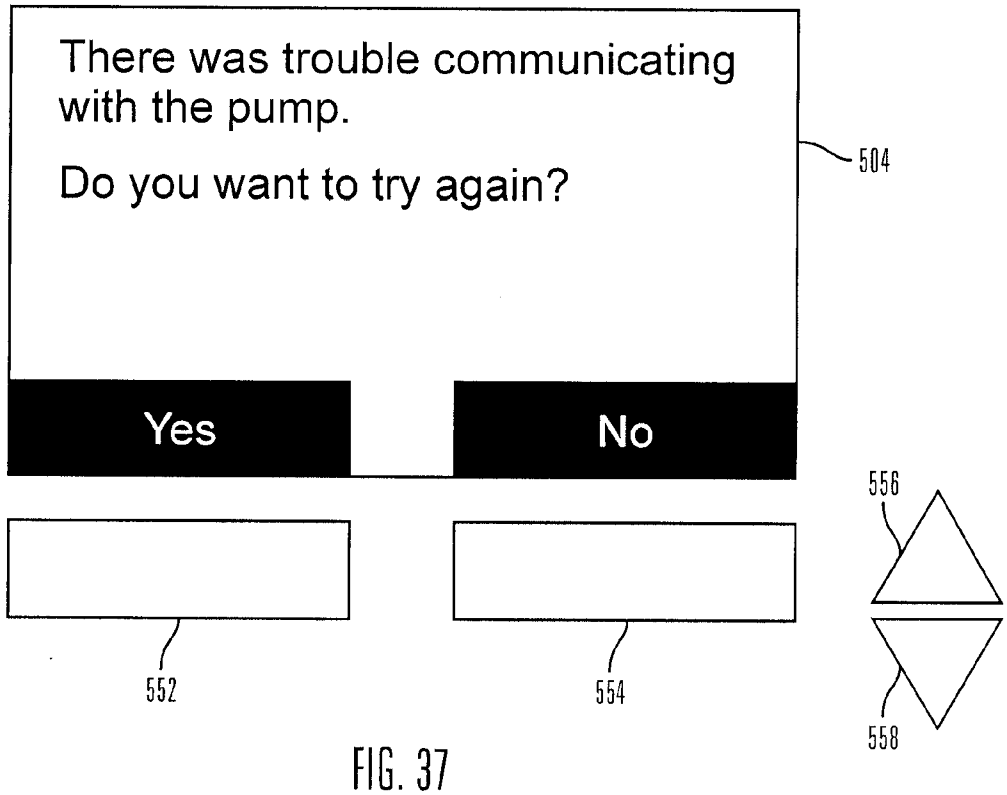
FIG. 37 is a softkey screen view of an LCD for use with the embodiment of the communication station shown in FIG. 33.

FIG. 37 illustrates the softkey screen, which allows the user to decide on simple options where the user only has two choices that can be presented on a softkey screen. A softkey screen simply presents each option as an individual softkey or as a Yes 552 or No 554.

Figure 38:
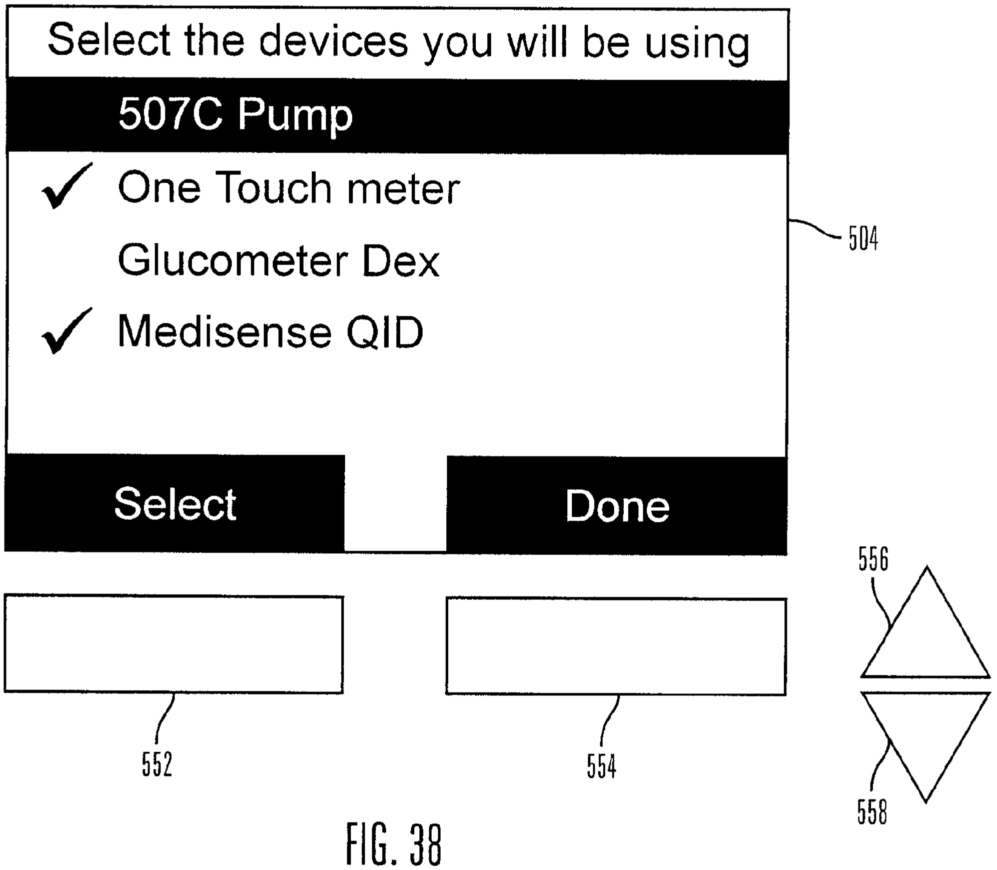
FIG. 38 is a check screen view of an LCD for use with the embodiment of the communication station shown in FIG. 33.

FIG. 38 illustrates the check screen which, like the menu screen, uses the arrow keys 556 and 558 to move an inverted bar up and down over a list of options. Unlike the menu screen, selecting the option simply places a check mark by the highlighted item. When the user is done with the screen they may press the softkey 554 labeled done.

Software in the communication station 500 will support the user scenarios listed below.

Scenario 1: Initial Setup

This scenario describes the first user interaction with the communication station 500. For instance, the communication station 500 is powered on by plugging in the device. An initial greeting is presented to the user such as "Welcome to the MiniMed Com Station. I'm going to ask you a few questions to set things up." A softkey label continue is presented. The user presses continue and is presented with the screen "Do you need to do anything special to get an outside line, such as dial 9?" The user is presented with softkeys labeled yes and no. If the user hits yes, they are presented with a numeric entry screen which allows them to enter the number required for and outside line. The next question the user is presented with is "Do you have call waiting?". The user is presented with softkeys labeled yes and no. If the user hits yes, they are presented with a numeric entry screen which allows them to enter the number required to disable call waiting. The user is presented with a screen saying "Congratulations! Setup is complete. If you ever want to change your setup you can do so from the main menu" A softkey label continue is presented. The user is then presented with the main screen. The main screen is a menu screen with three options: Setup, Collection information, Send information to a remote source (see FIG. 35).

Scenario 2: Typical Data Collection and Upload

This scenario describes the typical user interaction with the communication station 500. For instance, the user places his infusion pump 12 or glucose monitor 18 in the cradle 20 or connects a glucose meter 24 to the serial port 26. The user selects collect information from the LCD screen 504. The user is presented with a list of devices. The user selects the infusion pump 12, glucose monitor 18, and/or glucose meter 24 that is to be download from. The user receives a message such as "Communicating with <name of device>. Please wait . . . " Once communication is complete a message such as "Communication complete. Do you want to send the collected information to a remote location?" If the user chooses to send the data to the remote location, they are presented with a screen that says "Contacting Remote Network Services, please wait."During the data transfer, the LCD 504 will display a screen that says "Data being sent to Remote Network Services, please wait . . . " A progress bar indicates the time remaining. Once the data has been sent, a message such as "Finished sending data to Remote Network Services." The user presses continue and is returned to the main menu.

Scenario 3: Typical PC Use

This scenario describes the typical user interaction with the device. For instance, following the directions on the PC screen, the user connects a serial cable from their PC 14 to the communication station 500. When the user clicks a button on the PC screen, the communication station 500 screen displays the message "The communication station is in PC controlled mode." The user follows the instructions on the PC screen. Once the session is terminated, the communication station 500 returns to the main menu.

As discussed above, the communication station 500 can communicate with a network-based data management service that will gather device and patient data in a central location and produce reports for use by care providers, managed care organizations, and patients, such as disclosed in U.S. Patent Application Ser. No. 60/143,981 filed May 20, 1999 and entitled "Diabetes Integrated Management System", which is incorporated by reference herein. The initial goal of a data management service will be to gather device data with minimal user interaction and fax a report to the care provider's office in advance of a patient appointment. This service will rely on communications devices and software in either the patient's homes or the care provider's offices to gather device data and transmit it to the data management service via modem. A communication station 500 will be used as a communication device to gather data from current medical devices and to interact with the network-based data management service. Future phases of the data management service will support direct patient interaction with the service for the purpose of conducting medical and marketing surveys, presenting medical instructions, conducting tutorials, and electronic ordering of supplies.

The following describes a typical interaction between the communication station 500 and the network service: For instance, the communication station 500 calls network server and establishes initial connection. The server responds with a successful login in message and server time. The communication station 500 records this time. In preferred embodiments, the network server never calls the communication station 500; however, in alternative embodiments, the network server may call the communication station 500 at periodic intervals or to check on the status of a patient that is overdue to transmit data. Next, the communication station 500 downloads an instr.bat file. This file tells the communication station that it needs to update its code using newcode.bin and update its screens using newscreens.xml. The communication station 500 looks and sees if there are any special instructions just for it on the network server. To do this it looks for an instruction file with it's serial number (i.e. SN1234_instr.bat). This file might tell it that it has a couple of messages waiting specifically for it (i.e. SN1234_msg1.xml and SN1234_msg2.xml). The communication station 500 then sends a SN1234_hist.dat file. This file contains a log of errors encountered and other communication station 500 status information. Next, the communication station 500 sends all the download data files in its memory using the instr.bat file or the SN1234_instr.bat if such a file exists. After the transfer is complete, a success message is sent, and either the network server or the communication station 500 will terminate the connection.

The data downloaded from the devices shall be stored in the exact format they are received. Data shall be transferred using Xmodem-1K. On manufacture the Real Time Clock 516 is set in such a way that it is effectively a counter counting minutes and seconds since the date of manufacture. This counter is battery backed and never reset. It provides an absolute reference against which all other times are measured. When devices are downloaded, the time of the device is recorded along with the manufacture counter time. This will enable the conversion of the data from device time to manufacture counter time. In this way, no matter what the variety of device times, all data can be normalized to manufacture counter time. When the communication station 500 connects with the network, the network responds with its time. Upon reception of the network time, the network time is recorded along with the corresponding manufacture counter time. This will enable the conversion of the manufacture counter normalized timestamps to network time.

The communication station 500 will have the ability to communicate with a PC 14 via an RS232 link to a DB9 com port 16. There is a PC Controlled Mode, where upon reception of a command to put the communication station 500 in PC Controlled Mode, the communication station 500 locks out all normal functions and places the message "The communication station is under the control of your PC, press Cancel to end control". The communication station remains in PC Controlled Mode until released by the PC 14, the cancel softkey is pressed on the communication station 500, or the communication station 500 times out. In PC Controlled Mode the following commands are available: program the communication station 500; program the PIC Microcontroller in the RF section of the communication station 500; put a message on the LCD display 504 of the communication station 500; put the communication station 500 serial ports 26 and 520 in pass through mode; directly communicate serially with the IR transmitters and receivers 22; directly communicate serially with the RF transceiver 526; determine what files are stored in the communication station memory 508 and 510 and download them; instruct the communication station 500 to download data from specific devices (such as an infusion pump 12) to the file system. This differs from direct IR or RF communications in that the PC 14 relies on the communication station to handle the protocol for communicating with these devices; and download the communication station 500 history and status information. There is also a communication station 500 Debug Mode, which is similar to PC Controlled mode in that it involves serial communication with a PC. However, unlike PC controlled mode, the Debug Mode does not lock out normal communication station 500 functioning. In Debug Mode the following commands are available: program the communication station 500; program the PIC Microcontroller in the RF section of the communication station 500; determine what files are stored in the communication station memory 508 and 510 and download them; download the communication station 500 history and status information; simulate a keypress; adjust the LCD contrast 504; batch program the communication station 500 and the PIC microcontroller (this allows multiple devices to be programmed simultaneously); and failure simulation.

As discussed above, the communication station 500 will have the ability to perform several levels of in field code update, including: PIC Microcontroller update; screens update; normal code update; and Boot Block update. The PIC Microcontroller update is responsible for updating certain aspects of the RF protocol used in communicating with the RF data transmitting and programmable devices. The Screens update changes the screen wording to access new functions and features. The Normal Code Update updates everything except for a small amount of boot code. If a normal code update fails, the boot block provides the code for recovery and retry. The Boot Block Update remotely updates the boot block. However, if the update of this portion of code fails, the device will have to be returned for reprogramming.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A communication system for monitoring a medical condition for a patient, comprising:

a plurality of medical devices including a continuous glucose monitor for obtaining continuous glucose level measurement data for the patient over a plurality of days and a glucose meter for obtaining discrete glucose level calibration and reference data over the plurality of days that is used by the continuous glucose monitor to calibrate the continuous glucose level measurement data for the patient over the plurality of days;

a processing device including:

a processing device display, and at least one embedded computer program; and a communication device for providing a communication link between the plurality of medical devices and the processing device such that data may be transferred from the plurality of medical devices to the processing device, wherein the at least one embedded computer program causes the processing device to perform:

generating a patient data file, downloading the continuous glucose level measurement data for the patient obtained by the continuous glucose monitor over the plurality of days and the discrete glucose level calibration and reference data obtained by the glucose meter over the plurality of days, recording the downloaded data in the patient data file, integrating the downloaded data from the continuous glucose monitor and the glucose meter to present contemporaneous information showing the relationship between the continuous glucose monitor and the glucose meter, presenting the integrated data in a modal day report format including a modal day graph having a single 24-hour day time scale on a first axis and a glucose level scale on a second axis, and displaying on the processing device display the continuous glucose level measurement data obtained over a first day of the plurality of days and the discrete glucose level calibration and reference data obtained over the first day of the plurality of days that is used to calibrate the continuous glucose level measurement data during the first day in an overlaid fashion relative to the continuous glucose level measurement data obtained over a second day of the plurality of days and the discrete glucose level calibration and reference data obtained over the second day of the plurality of days that is used to calibrate the continuous glucose level measurement data during the second day on the same, single 24-hour day time scale within the modal day graph.

2. The communication system of claim 1, wherein the continuous glucose level measurement data obtained over the first day is displayed in the modal day graph in a first color, and the continuous glucose level measurement data obtained over the second day is displayed in the modal day graph in a second color different from the first color.

3. The communication system of claim 2, wherein the discrete glucose level calibration and reference data obtained during the first day is displayed in the modal day graph in the first color, and the discrete glucose level calibration and reference data obtained over the second day is displayed in the modal day graph in the second color.

4. The communication system of claim 1, wherein the continuous glucose level measurement data obtained over the first day is displayed as a first continuous line graphical representation of blood glucose levels on the modal day graph, and the continuous glucose level measurement data obtained over the second day is displayed as a second continuous line graphical representation of blood glucose levels on the modal day graph.

5. The communication system of claim 1, wherein the discrete glucose level calibration and reference data obtained over the first day and the discrete glucose level calibration and reference data obtained over the second day is displayed as one or more discrete point graphical representations on the modal day graph, each discrete point graphical representation corresponding to a discrete blood glucose level measurement included in the discrete glucose level calibration and reference data obtained during the first and second days that is used to calibrate the continuous glucose level measurement data obtained over the first and second days.

6. The communication system of claim 1, wherein the discrete glucose level calibration and reference obtained during the first and second days include at least one of discrete time stamped glucose level measurements, current clock settings, and event markers.

7. The communication system of claim 1, wherein the continuous glucose level measurement data obtained during the first and second days include at least one of sensor glucose level measurements, current clock settings, event markers, and manually entered glucose level calibration and reference measurements.

8. The communication system of claim 1, wherein the modal day report format further includes a tabular chart, and the at least one embedded computer program further causes the processing device to perform:

calculating an average glucose level based on the continuous glucose level measurement data obtained by the continuous glucose monitor over the plurality of days, displaying on the processing device display the average glucose level as a straight line along the second axis within the modal day graph, and displaying on the processing device display the average glucose level in the tabular chart.

9. The communication system of claim 1, wherein the modal day report format further includes a tabular chart, and the at least one embedded computer program further causes the processing device to perform:

calculating a standard deviation based on the continuous glucose level measurement data obtained by the continuous glucose monitor over the plurality of days, and displaying on the processing device display the calculated standard deviation in the tabular chart.

10. The communication system of claim 1, wherein the modal day report format further includes a tabular or pie chart, and the at least one embedded computer program further causes the processing device to perform:

calculating a percentage of the continuous glucose level measurement data obtained by the continuous glucose monitor over the plurality of days that is equal to or above a hyperglycemic limit for the patient, calculating a percentage of the continuous glucose level measurement data obtained by the continuous glucose monitor over the plurality of days that is equal to or below a hypoglycemic limit for the patient, calculating a percentage of the continuous glucose level measurement data obtained by the continuous glucose monitor over the plurality of days that is below the hyperglycemic limit and above the hypoglycemic limit for the patient, and displaying on the processing device display the calculated percentages in the tabular or pie chart.

11. The communication system of claim 1, wherein the modal day report format further includes a tabular chart, and the at least one embedded computer program further causes the processing device to perform:

determining a maximum glucose level measurement and a minimum glucose level measurement included in the continuous glucose level measurement data obtained by the continuous glucose monitor over the plurality of days, and displaying on the processing device display the maximum and minimum glucose level measurements in the tabular chart.

* * * * *